United States Patent
Fontanarava et al.

(10) Patent No.: US 11,678,831 B2
(45) Date of Patent: Jun. 20, 2023

(54) ELECTROCARDIOGRAM PROCESSING SYSTEM FOR DETECTING AND/OR PREDICTING CARDIAC EVENTS

(71) Applicant: Cardiologs Technologies SAS, Paris (FR)

(72) Inventors: Julien Fontanarava, Paris (FR); Gregoire De Masse, Paris (FR); Jia Li, Paris (FR); Chiara Scabellone, Paris (FR)

(73) Assignee: CARDIOLOGS TECHNOLOGIES SAS, Paris (FR)

( * ) Notice: Subject to any disclaimer, the term of this patent is extended or adjusted under 35 U.S.C. 154(b) by 0 days.

(21) Appl. No.: 17/397,782

(22) Filed: Aug. 9, 2021

(65) Prior Publication Data
US 2022/0039729 A1    Feb. 10, 2022

Related U.S. Application Data

(60) Provisional application No. 63/063,899, filed on Aug. 10, 2020.

(30) Foreign Application Priority Data

Dec. 15, 2020  (EP) .................................... 20306566

(51) Int. Cl.
*A61B 5/361*   (2021.01)
*G16H 50/30*   (2018.01)
(Continued)

(52) U.S. Cl.
CPC .............. *A61B 5/361* (2021.01); *A61B 5/339* (2021.01); *A61B 5/366* (2021.01); *G06N 3/04* (2013.01); *G16H 50/20* (2018.01); *G16H 50/30* (2018.01)

(58) Field of Classification Search
CPC ......... A61B 5/361; A61B 5/339; A61B 5/366; G16H 50/30; G16H 50/20; G06N 3/04
See application file for complete search history.

(56) References Cited

U.S. PATENT DOCUMENTS 5,024,225 A   6/1991  Fang
5,239,494 A   8/1993  Golbeck
(Continued)

FOREIGN PATENT DOCUMENTS

CA    2466848 A1    6/2003
CN    101268938 A    9/2008
(Continued)

OTHER PUBLICATIONS

Alfonso, et al., ECG Beat Detection Using Filter Banks, IEEE Transactions on Biomedical Engineering, 46(2):192-202 (Feb. 1999).
(Continued)

*Primary Examiner* — Lynsey C Eiseman
*Assistant Examiner* — Jessandra F Hough

(57) ABSTRACT

Systems and methods are provided for analyzing electrocardiogram (ECG) data of a patient using a substantial amount of ECG data. The systems receive ECG data from a sensing device positioned on a patient such as one or more ECG leads/electrodes that may be integrated in a smart device. The system may include an application that communicates with an ECG platform running on a server(s) that processes and analyzes the ECG data, e.g., using neural networks, to detect and/or predict various abnormalities, conditions and/or descriptors. The system may also determine a confidence score corresponding to the abnormalities, conditions and/or descriptors. The processed ECG data is used to generate a graphic user interface that is communicated from the server(s) to a computer for display in a user-friendly and interactive manner with enhanced accuracy.

27 Claims, 36 Drawing Sheets

(51) Int. Cl.
  *G16H 50/20* (2018.01)
  *A61B 5/339* (2021.01)
  *A61B 5/366* (2021.01)
  *G06N 3/04* (2023.01)

(56) References Cited

U.S. PATENT DOCUMENTS

| | | | |
|---|---|---|---|
| 5,619,991 A | 4/1997 | Sloane | |
| 5,623,935 A | 4/1997 | Faisandier | |
| 5,819,007 A | 10/1998 | Elghazzawi | |
| 5,907,291 A | 5/1999 | Chen et al. | |
| 5,966,692 A | 10/1999 | Langer et al. | |
| 6,024,699 A | 2/2000 | Surwit et al. | |
| 6,157,850 A | 12/2000 | Diab et al. | |
| 6,507,753 B1 | 1/2003 | Xue et al. | |
| 6,612,985 B2 | 9/2003 | Eiffert et al. | |
| 6,656,125 B2 | 12/2003 | Misczynski et al. | |
| 6,694,177 B2 | 2/2004 | Eggers et al. | |
| 7,142,907 B2 | 11/2006 | Xue et al. | |
| 7,289,844 B2 | 10/2007 | Misczynski et al. | |
| 7,941,207 B2 | 5/2011 | Korzinov | |
| RE43,767 E | 10/2012 | Eggers et al. | |
| 8,332,017 B2 | 12/2012 | Tarassenko et al. | |
| 8,668,644 B2 | 3/2014 | Ong et al. | |
| 8,684,900 B2 | 4/2014 | Tran | |
| 8,818,496 B2 | 8/2014 | Dziubinski et al. | |
| D717,955 S | 11/2014 | Bishay et al. | |
| 8,903,479 B2 | 12/2014 | Zoicas | |
| 8,932,220 B2 | 1/2015 | Ong et al. | |
| 8,951,193 B2 | 2/2015 | Ong et al. | |
| D744,659 S | 12/2015 | Bishay et al. | |
| 9,241,650 B2 | 1/2016 | Amirim | |
| 9,254,095 B2 | 2/2016 | Galloway et al. | |
| 9,295,429 B2 | 3/2016 | Ong et al. | |
| 9,339,202 B2 | 5/2016 | Brockway et al. | |
| 9,345,414 B1 | 5/2016 | Bardy et al. | |
| 9,351,652 B2 | 5/2016 | Dziubinski et al. | |
| 9,364,155 B2 | 6/2016 | Bardy et al. | |
| 9,408,545 B2 | 8/2016 | Felix et al. | |
| 9,408,551 B2 | 8/2016 | Bardy et al. | |
| 9,420,957 B2 | 8/2016 | Ong et al. | |
| D766,447 S | 9/2016 | Bishay et al. | |
| 9,433,367 B2 | 9/2016 | Felix et al. | |
| 9,433,380 B1 | 9/2016 | Bishay et al. | |
| 9,468,386 B2 | 10/2016 | Braojos Lopez et al. | |
| 9,504,423 B1 | 11/2016 | Bardy et al. | |
| 9,545,204 B2 | 1/2017 | Bishay et al. | |
| 9,545,228 B2 | 1/2017 | Bardy et al. | |
| 9,554,715 B2 | 1/2017 | Bardy et al. | |
| 9,615,763 B2 | 4/2017 | Felix et al. | |
| 9,619,660 B1 | 4/2017 | Felix et al. | |
| 9,642,537 B2 | 5/2017 | Felix et al. | |
| 9,655,537 B2 | 5/2017 | Bardy et al. | |
| 9,655,538 B2 | 5/2017 | Felix et al. | |
| 9,700,227 B2 | 7/2017 | Bishay et al. | |
| D793,566 S | 8/2017 | Bishay et al. | |
| 9,717,432 B2 | 8/2017 | Felix et al. | |
| 9,717,433 B2 | 8/2017 | Felix et al. | |
| 9,730,593 B2 | 8/2017 | Felix et al. | |
| 9,730,641 B2 | 8/2017 | Felix et al. | |
| 9,737,211 B2 | 8/2017 | Bardy et al. | |
| 9,737,224 B2 | 8/2017 | Bardy et al. | |
| D801,528 S | 10/2017 | Bardy et al. | |
| 9,775,536 B2 | 10/2017 | Felix et al. | |
| 9,788,722 B2 | 10/2017 | Bardy et al. | |
| 9,808,206 B1 | 11/2017 | Zhao et al. | |
| 9,820,665 B2 | 11/2017 | Felix et al. | |
| 9,901,274 B2 | 2/2018 | Bishay et al. | |
| 9,936,875 B2 | 4/2018 | Bardy et al. | |
| 9,955,885 B2 | 5/2018 | Felix et al. | |
| 9,955,888 B2 | 5/2018 | Felix et al. | |
| 9,955,911 B2 | 5/2018 | Bardy et al. | |
| 10,004,415 B2 | 6/2018 | Bishay et al. | |
| 10,045,709 B2 | 8/2018 | Bardy et al. | |
| 10,052,022 B2 | 8/2018 | Bardy et al. | |
| D831,833 S | 10/2018 | Bishay et al. | |
| 10,111,601 B2 | 10/2018 | Bishay et al. | |
| 10,123,703 B2 | 11/2018 | Bardy et al. | |
| 10,154,793 B2 | 12/2018 | Felix et al. | |
| D838,370 S | 1/2019 | Bardy et al. | |
| 10,165,946 B2 | 1/2019 | Bardy et al. | |
| 10,172,534 B2 | 1/2019 | Felix et al. | |
| 10,251,575 B2 | 4/2019 | Bardy et al. | |
| 10,251,576 B2 | 4/2019 | Bardy et al. | |
| 10,264,992 B2 | 4/2019 | Felix et al. | |
| 10,265,015 B2 | 4/2019 | Bardy et al. | |
| 10,271,755 B2 | 4/2019 | Felix et al. | |
| 10,271,756 B2 | 4/2019 | Felix et al. | |
| 10,278,603 B2 | 5/2019 | Felix et al. | |
| 10,278,606 B2 | 5/2019 | Bishay et al. | |
| 10,426,364 B2 | 10/2019 | Rapin et al. | |
| 10,492,730 B1 | 12/2019 | Mehta | |
| 10,568,570 B1 | 2/2020 | Sherpa | |
| 10,758,139 B2 | 9/2020 | Rapin et al. | |
| 10,779,744 B2 | 9/2020 | Rapin et al. | |
| 10,827,938 B2 | 11/2020 | Fontanarava et al. | |
| 10,959,660 B2 | 3/2021 | Li et al. | |
| 11,134,880 B2 | 10/2021 | Rapin et al. | |
| 11,147,500 B2 | 10/2021 | Li et al. | |
| 2001/0029338 A1 | 10/2001 | Krishnamachari | |
| 2003/0176795 A1 | 9/2003 | Harris et al. | |
| 2004/0147840 A1 | 7/2004 | Duggirala et al. | |
| 2004/0230105 A1 | 11/2004 | Geva et al. | |
| 2004/0260192 A1 | 12/2004 | Yamamoto | |
| 2005/0101873 A1 | 5/2005 | Misczynski et al. | |
| 2005/0113706 A1 | 5/2005 | Prystowsky et al. | |
| 2005/0171448 A1 | 8/2005 | Korzinov et al. | |
| 2005/0182334 A1 | 8/2005 | Korzinov et al. | |
| 2005/0222508 A1 | 10/2005 | Moreno et al. | |
| 2006/0020219 A1 | 1/2006 | Zinser, Jr. et al. | |
| 2006/0173369 A1 | 8/2006 | Kaski | |
| 2007/0129642 A1 | 6/2007 | Korzinov | |
| 2007/0191723 A1 | 8/2007 | Prystowsky et al. | |
| 2007/0244402 A1* | 10/2007 | Brockway | G16H 50/30 600/509 |
| 2008/0004904 A1 | 1/2008 | Tran | |
| 2008/0082016 A1 | 4/2008 | Kohls et al. | |
| 2008/0103403 A1 | 5/2008 | Cohen | |
| 2008/0132799 A1 | 6/2008 | Xue | |
| 2008/0167567 A1* | 7/2008 | Bashour | A61B 5/361 600/518 |
| 2009/0112110 A1 | 4/2009 | Zhang | |
| 2009/0192394 A1 | 7/2009 | Guttag et al. | |
| 2010/0030302 A1 | 2/2010 | Blowers et al. | |
| 2010/0076331 A1 | 3/2010 | Chan et al. | |
| 2010/0217144 A1 | 8/2010 | Brian | |
| 2010/0268103 A1 | 10/2010 | McNamara et al. | |
| 2011/0184297 A1 | 7/2011 | Vitali et al. | |
| 2011/0224565 A1 | 9/2011 | Ong et al. | |
| 2011/0257548 A1 | 10/2011 | Dong et al. | |
| 2011/0282225 A1 | 11/2011 | Anderson et al. | |
| 2011/0301435 A1 | 12/2011 | Albert et al. | |
| 2012/0110226 A1 | 5/2012 | Vlach et al. | |
| 2012/0203491 A1 | 8/2012 | Sun et al. | |
| 2012/0278099 A1 | 11/2012 | Kelly et al. | |
| 2013/0116585 A1 | 5/2013 | Bouguerra | |
| 2013/0184599 A1 | 7/2013 | Friedman et al. | |
| 2013/0237776 A1 | 9/2013 | Ong et al. | |
| 2014/0005988 A1 | 1/2014 | Brockway | |
| 2014/0107493 A1 | 4/2014 | Yuen et al. | |
| 2014/0128758 A1 | 5/2014 | Galloway et al. | |
| 2014/0148714 A1 | 5/2014 | Mamaghanian et al. | |
| 2014/0187988 A1 | 7/2014 | Ong et al. | |
| 2014/0188770 A1 | 7/2014 | Agrafioti et al. | |
| 2014/0228665 A1 | 8/2014 | Albert | |
| 2014/0275840 A1 | 9/2014 | Osorio | |
| 2015/0008802 A1 | 1/2015 | Fukuda | |
| 2015/0018702 A1 | 1/2015 | Galloway et al. | |
| 2015/0051505 A1 | 2/2015 | Rossi | |
| 2015/0088020 A1 | 3/2015 | Dreisbach et al. | |
| 2015/0088024 A1 | 3/2015 | Sackellares et al. | |
| 2015/0105640 A1 | 4/2015 | Friedman et al. | |
| 2015/0119725 A1 | 4/2015 | Martin et al. | |
| 2015/0164349 A1 | 6/2015 | Gopalakrishnan et al. | |

(56) References Cited

U.S. PATENT DOCUMENTS

| | | |
|---|---|---|
| 2015/0190067 A1 | 7/2015 | Prystowsky et al. |
| 2015/0223759 A1 | 8/2015 | Ong et al. |
| 2015/0248534 A1 | 9/2015 | Krzywicki et al. |
| 2015/0257668 A1 | 9/2015 | Braojos Lopez et al. |
| 2015/0282726 A1 | 10/2015 | Grube et al. |
| 2015/0289112 A1 | 10/2015 | Gilbert et al. |
| 2016/0051157 A1 | 2/2016 | Waydo |
| 2016/0058318 A1* | 3/2016 | Borjigin ............... G16H 50/20 600/516 |
| 2016/0085927 A1 | 3/2016 | Dettinger et al. |
| 2016/0085937 A1 | 3/2016 | Dettinger et al. |
| 2016/0086297 A1 | 3/2016 | Dettinger et al. |
| 2016/0098536 A1 | 4/2016 | Dettinger et al. |
| 2016/0098537 A1 | 4/2016 | Dettinger et al. |
| 2016/0098538 A1 | 4/2016 | Dettinger et al. |
| 2016/0135706 A1* | 5/2016 | Sullivan ............. A61B 5/14552 600/301 |
| 2016/0150989 A1 | 6/2016 | Felix et al. |
| 2016/0183827 A1 | 6/2016 | Xue et al. |
| 2016/0183829 A1 | 6/2016 | Friedman et al. |
| 2016/0192853 A1 | 7/2016 | Bardy et al. |
| 2016/0235319 A1 | 8/2016 | Albert |
| 2016/0242665 A1 | 8/2016 | Galloway et al. |
| 2016/0249823 A1 | 9/2016 | Galloway et al. |
| 2016/0262646 A1 | 9/2016 | Bardy et al. |
| 2016/0321430 A1 | 11/2016 | Eckman et al. |
| 2016/0345854 A1 | 12/2016 | Bardy et al. |
| 2016/0345909 A1 | 12/2016 | Felix et al. |
| 2017/0095153 A1 | 4/2017 | Bardy et al. |
| 2017/0098047 A1 | 4/2017 | Young |
| 2017/0105683 A1 | 4/2017 | Xue |
| 2017/0112401 A1* | 4/2017 | Rapin .................. A61B 5/7267 |
| 2017/0135579 A1 | 5/2017 | Bardy et al. |
| 2017/0177811 A1 | 6/2017 | McFarland et al. |
| 2017/0188872 A1 | 7/2017 | Hughes et al. |
| 2017/0238833 A1 | 8/2017 | Felix et al. |
| 2017/0251948 A1 | 9/2017 | Felix et al. |
| 2017/0258358 A1 | 9/2017 | Bishay et al. |
| 2017/0340206 A1 | 11/2017 | Bardy et al. |
| 2017/0340290 A1 | 11/2017 | Felix et al. |
| 2017/0357764 A1 | 12/2017 | Fauss et al. |
| 2017/0367609 A1 | 12/2017 | Bardy et al. |
| 2018/0020939 A1 | 1/2018 | Albert |
| 2018/0028144 A1 | 2/2018 | Chen et al. |
| 2018/0060522 A1 | 3/2018 | Petterson et al. |
| 2018/0146875 A1 | 5/2018 | Friedman et al. |
| 2018/0177423 A1 | 6/2018 | Bishay et al. |
| 2018/0206752 A1 | 7/2018 | Bardy et al. |
| 2018/0242876 A1 | 8/2018 | Hughes et al. |
| 2018/0279956 A1 | 10/2018 | Waydo et al. |
| 2018/0289274 A1 | 10/2018 | Bahney et al. |
| 2018/0296118 A1 | 10/2018 | Bishay et al. |
| 2018/0310892 A1 | 11/2018 | Perschbacher et al. |
| 2018/0344189 A1 | 12/2018 | Dusan |
| 2018/0344191 A1 | 12/2018 | Bardy et al. |
| 2018/0353071 A1 | 12/2018 | Bardy et al. |
| 2018/0368715 A1 | 12/2018 | Xue et al. |
| 2018/0374576 A1 | 12/2018 | Dettinger et al. |
| 2019/0034050 A1 | 1/2019 | Williams et al. |
| 2019/0038149 A1 | 2/2019 | Gopalakrishnan et al. |
| 2019/0059763 A1 | 2/2019 | Shakur et al. |
| 2019/0069794 A1 | 3/2019 | Bardy et al. |
| 2019/0069798 A1 | 3/2019 | Bardy |
| 2019/0069800 A1 | 3/2019 | Bardy et al. |
| 2019/0076023 A1 | 3/2019 | Bardy et al. |
| 2019/0090769 A1 | 3/2019 | Boleyn et al. |
| 2019/0099105 A1 | 4/2019 | Felix et al. |
| 2019/0104951 A1 | 4/2019 | Valys et al. |
| 2019/0104961 A1 | 4/2019 | Felix et al. |
| 2019/0117068 A1 | 4/2019 | Thomson et al. |
| 2019/0117099 A1 | 4/2019 | Bardy et al. |
| 2019/0117107 A1 | 4/2019 | Felix et al. |
| 2019/0133444 A1 | 5/2019 | Bardy et al. |
| 2019/0133483 A1 | 5/2019 | Xue et al. |
| 2019/0133486 A1 | 5/2019 | Felix et al. |
| 2019/0167141 A1 | 6/2019 | Duckert et al. |
| 2019/0167143 A1 | 6/2019 | Li et al. |
| 2019/0223739 A1 | 7/2019 | Rapin et al. |
| 2019/0259496 A1 | 8/2019 | Pemberton et al. |
| 2019/0267139 A1 | 8/2019 | Hutchins et al. |
| 2019/0272920 A1 | 9/2019 | Teplitzky |
| 2019/0274563 A1 | 9/2019 | Soli et al. |
| 2019/0274574 A1 | 9/2019 | Hughes et al. |
| 2019/0282118 A1 | 9/2019 | Kaski |
| 2019/0298204 A1 | 10/2019 | Fontanarava et al. |
| 2019/0357794 A1 | 11/2019 | Bardy et al. |
| 2020/0013507 A1 | 1/2020 | Braun et al. |
| 2020/0015694 A1 | 1/2020 | Rapin et al. |
| 2020/0022591 A1 | 1/2020 | Drakulic et al. |
| 2020/0022604 A1 | 1/2020 | Scabellone et al. |
| 2020/0029911 A1 | 1/2020 | Chakravarthy et al. |
| 2020/0060563 A1 | 2/2020 | Boleyn et al. |
| 2020/0118673 A1 | 4/2020 | Dettinger et al. |
| 2020/0155025 A1 | 5/2020 | Smith et al. |
| 2020/0178825 A1 | 6/2020 | Lu et al. |
| 2020/0205745 A1 | 7/2020 | Khosousi et al. |
| 2020/0237317 A1 | 7/2020 | Newberry et al. |
| 2020/0273567 A1 | 8/2020 | Petterson et al. |
| 2020/0289014 A1 | 9/2020 | Park et al. |
| 2020/0289033 A1 | 9/2020 | Sivertsen et al. |
| 2020/0289063 A1 | 9/2020 | Mehta |
| 2020/0401684 A1 | 12/2020 | Vath et al. |
| 2021/0000344 A1 | 1/2021 | Dreisbach et al. |
| 2021/0000365 A1 | 1/2021 | Rapin et al. |
| 2021/0150693 A1* | 5/2021 | Fornwalt ................ G16H 20/40 |
| 2021/0204859 A1* | 7/2021 | Moll ........................ A61N 1/365 |
| 2021/0271847 A1* | 9/2021 | Courtiol ................ G06K 9/6261 |

FOREIGN PATENT DOCUMENTS

| | | |
|---|---|---|
| CN | 101766484 A | 7/2010 |
| CN | 102188240 A | 9/2011 |
| CN | 102379694 A | 3/2012 |
| CN | 102779234 A | 11/2012 |
| CN | 103038772 A | 4/2013 |
| CN | 103110417 A | 5/2013 |
| CN | 103284702 A | 9/2013 |
| CN | 103417209 A | 12/2013 |
| CN | 104463326 A | 3/2015 |
| CN | 104970789 A | 10/2015 |
| CN | 106778685 A | 5/2017 |
| DE | 60127354 T2 | 12/2007 |
| EP | 0465241 A2 | 1/1992 |
| EP | 0465241 B1 | 11/1998 |
| EP | 1179319 A1 | 2/2002 |
| EP | 1503664 A2 | 2/2005 |
| EP | 2030565 A1 | 3/2009 |
| EP | 2534597 A2 | 12/2012 |
| EP | 3144851 A1 | 3/2017 |
| EP | 2534597 B1 | 10/2018 |
| JP | 2002172096 A | 6/2002 |
| JP | 2013524865 A | 6/2013 |
| KR | 20150020955 A | 2/2015 |
| WO | WO-9738626 A1 | 10/1997 |
| WO | WO-03045224 A2 | 6/2003 |
| WO | WO-03045224 A3 | 11/2004 |
| WO | WO-2006048881 A2 | 5/2006 |
| WO | WO-2011115576 A2 | 9/2011 |
| WO | WO-2012140559 A1 | 10/2012 |
| WO | WO-2016110804 A1 | 7/2016 |
| WO | WO-2016145392 A1 | 9/2016 |
| WO | WO-2017072250 A1 | 5/2017 |
| WO | WO-2019038435 A1 | 2/2019 |
| WO | WO-2019089830 A1 | 5/2019 |
| WO | WO-2019147180 A1 | 8/2019 |
| WO | WO-2020086865 A1 | 4/2020 |
| WO | WO-2020161605 A1 | 8/2020 |

OTHER PUBLICATIONS

Almeida, et al., Multilead ECG Delineation Using Spatially Projected Leads From Wavelet Transform Loops, IEEE Transactions on Biomedical Engineering, 56(8):1996-2005 (Aug. 2009).

(56) References Cited

OTHER PUBLICATIONS

Attia, et al., An artificial intelligence-enabled ECG algorithm for the identification of patients with atrial fibrillation during sinus rhythm: a retrospective analysis of outcome prediction, The Lancet, 394(10201):861-867 (Sep. 2019).
Badilini, et al., ECGScan: A Method for Conversion of Paper Electrocardiographic Printouts to Digital Electrocardiographic Files, Journal of Electrocardiology, 38:310-318 (Oct. 2005).
Bishop, Pattern Recognition and Machine Learning, Springer, Information Science and Statistics, 2006, ISBN-10: 0-387-31073-8, New York, NY, USA.
Boichat, et al., Wavelet-Based ECG Delineation on a Wearable Embedded Sensor Platform, Proceedings of Wearable and Implantable Body Sensor Networks,*2009 Sixth International Workshop on Wearable and Implantable Body Sensor Networks*, IEEE (pp. 256-261) (Jun. 2009).
Chazal, et al., A Patient-Adapting Heartbeat Classifier Using ECG Morphology and Heartbeat Interval Features, IEEE Transactions on Biomedical Engineering, 53(12):2535-2543 (Dec. 2006).
Chazal, et al., Automatic Classification of Heartbeats Using ECG Morphology and Heartbeat Interval Features, IEEE Transactions on Biomedical Engineering, 51(7):1196-1206 (Jul. 2004).
Chebil, et al., A Novel Method for Digitizing Standard ECG Papers, Proceedings of the International Conference on Computer and Communication Engineering 2008, May 13-15, 2008, Kuala Lumpur, Malaysia (pp. 1308-1312).
Choi, et al., Development of ECG Beat Segmentation Method by Combining Lowpass Filter and Irregular R-R Interval Checkup Strategy, Expert Systems with Applications, 37:5208-5218 (Jul. 2010).
Christopoulos, et al., Artificial Intelligence-Electrocardiography to Predict Incident Atrial Fibrillation—A Population-Based Study, Circulation: Arrhythmia and Electrophysiology, 13(12):e009355 (Dec. 2020).
Coast, et al., An Approach to Cardiac Arrhythmia Analysis Using Hidden Markov Models, IEEE transactions on biomedical engineering, 37(9):826-836 (Sep. 1990).
Cybenko, Approximation by Superpositions of a Sigmoidal Function, *Mathematics of Control, Signals and Systems*, 2(4):303-314 (Dec. 1989).
Donahue et al., Long-term Recurrent Convolutional Networks for Visual Recognition and Description, arXiv:1411.4389v3, (pp. 1-13) (Feb. 2015).
Dubois, et al., Automatic ECG Wave Extraction in Long-Term Recordings using Gaussian Mesa Function Models and Nonlinear Probability Estimators, *Computer Methods and Programs in Biomedicine*, 88:217-233 (Mar. 2007).
European Search Report dated Apr. 13, 2016 in EP Patent Appl. Serial No. 15191769.7 (0230).
Extended EP Search Report dated Apr. 12, 2021 in EP Patent Application Serial No. 20211449.2 (0431).
Extended European Search Report dated Jul. 20, 2021 in EP Patent Appl. Serial No. 21167613.5 (0331).
Extended European Search Report dated Oct. 15, 2018 in EP Patent Appl. Serial No. 18305376.8 (0530).
Fiorina, AI-Based Strategy Enables Faster Holter ECG Analysis With Equivalent Clinical Accuracy Compared to a Classical Strategy, EP Europace, vol. 22, Issue Supplement 1, Abstract 222 (Jun. 2020).
Fiorina, et al., Artificial Intelligence Based Platform Enables Faster Ambulatory Electrocardiogram Analysis With Equivalent Clinical Accuracy Compared to Traditional Solution, Circulation, vol. 140, Issue Suppl. 1, Abstract 9825 (Nov. 2019).
Fukushima., Neocognitron: A Self-organizing Neural Network Model for a Mechanism of Pattern Recognition Unaffected by Shift in Position, *Biological Cybernetics*, 36:193-202 (1980).
Hughes, et al., Markov Models for Automated ECG Interval Analysis, Proceedings of Neural Information Processing Systems, 2004, Oxford, UK, (pp. 611-618).
Ieva, et al., Multivariate Functional Clustering for the Morphological Analysis of Electrocardiograph Curves, Journal of the Royal Statistical Society: Series C (Applied Statistics), 62(3):401-418 (May 2013).
International Search Report & Written Opinion dated Aug. 1, 2019 in Int'l PCT Patent Appl. No. PCT/IB2019/052517 (0510).
International Search Report & Written Opinion dated Nov. 21, 2018 in Int'l PCT Patent Appl. Serial No. PCT/EP2018/072912 (0410).
International Search Report & Written Opinion dated Jun. 4, 2020 in PCT Patent Appl. Serial No. PCT/IB2020/050850 (0710).
International Search Report & Written Opinion dated Jan. 24, 2017 in Int'l PCT Patent Appl. Serial No. PCT/EP2016/075972 (0310).
Jin, et al., Deep Learning Research on Clinical Electrocardiogram Analysis, Science China Press, 45(3):398-416 (2015), English abstract provided.
Johnson, et al., R-Peak Estimation using Multimodal Lead Switching, *Computing in Cardiology 2014*, IEEE, pp. 281-284 (Sep. 2014).
Kaur et al., Comparison of Different Approaches for Removal of Baseline Wander From ECG Signal, *Proceedings of the International Conference & Workshop on Emerging Trends in Technology*, (pp. 30-36) (Feb. 2011).
Kiranyaz, et al., Convolutional Neural Networks for Patient-Specific ECG Classification,*2015 37th Annual International Conference of the IEEE Engineering in Medicine and Biology Society (EMBC)*, IEEE (pp. 2608-2611) (Aug. 2015).
Kiranyaz, et al., Real-Time Patient-Specific ECG Classification by 1-D Convolutional Neural Networks, *IEEE transactions on Biomedical Engineering*, 63(3):664-675 (Aug. 2015).
Krizhevsky, et al., ImageNet Classification with Deep Convolutional Neural Networks, Advances in neural information processing systems, 25:1097-1105 (2012).
Laguna, et al., A Database for Evaluation of Algorithms for Measurement of QT and Other Waveform Intervals in the ECG, *Computers in Cardiology 1997*, 24:673-676.
Lecun, et al., Backpropagation Applied to Handwritten Zip Code Recognition, *Neural Computation*, 1(4):541-551 (Dec. 1989).
Li, et al., Deep neural networks Improve Atrial Fibrillation Detection in Holter: first results, European Journal of Preventive Cardiology, Abstract, 23 (2S) (Oct. 2016).
Li, et al., Detection of ECG Characteristic Points Using Wavelet Transforms, *IEEE Transactions on Biomedical Engineering*, 42(1):21-28 (Jan. 1995).
Lin et al., Beat-to-beat P and T Wave Delineation in ECG Signals using a Marginalized Particle Filter, *2012 Proceedings of the 20th European Signal Processing Conference (EUSIPCO)*, (pp. 479-483) (Aug. 2012).
Lin, et al., P and Twave Delineation and Waveform Estimation in ECG Signals Using a Block Gibbs Sampler,*2011 IEEE International Conference on Acoustics, Speech and Signal Processing (ICASSP)*, (pp. 479-483) (May 2011).
Lin et al., P- and T-Wave Delineation in ECG Signals Using a Bayesian Approach and a Partially Collapsed Gibbs Sampler, *IEEE Transactions on Biomedical Engineering*, 57(12):2840-2849 (Sep. 2010).
Long, et al., Fully Convolutional Networks for Semantic Segmentation, Proceedings of the IEEE Conference on Computer Vision and Pattern Recognition, (pp. 3431-3440) (2015).
Maille, et al., Smartwatch Electrocardiogram and Artificial Intelligence for Assessing Cardiac-Rhythm Safety of Drug Therapy in the COVID-19 Pandemic. The QT-logs study, International Journal of Cardiology, 331:333-339 (May 2021).
Martinez et al., A Wavelet-Based ECG Delineator: Evaluation on Standard Databases, IEEE Transactions on Biomedical Engineering, 51(4): 570-581 (Mar. 2004).
Matan, et al., Multi-Digit Recognition Using a Space Displacement Neural Network, *Neural Information Processing Systems*, 2:488-495) (Jan. 1991).
Meghriche, et al., On the Analysis of a Compound Neural Network for Detecting Atrio Ventricular Heart Block (AVB) in an ECG Signal, *International Journal of Biological and Medical Sciences*, 1(1):1-11 (Mar. 2008).
Megriche, et al., On the Analysis of a Compound Neural Network for Detecting Atrio Ventricular Heart Block (AVB) in a ECG Signal,

(56) References Cited

OTHER PUBLICATIONS

International Journal of Medical, Health, Biomedical, Bioengineering and Pharmaceutical Engineering, 2(3):68-78 (2008).
Mittal, et al., AI Filter Improves Positive Predictive Value of Atrial Fibrillation Detection by an Implantable Loop Recorder, JACC: Clinical Electrophysiology, available online Feb. 10, 2021, https://doi.org/10.1016/j.jacep.2020.12.006.
Mittal, et al., An Artificial Intelligence-based Solution to Reduce False Positive Detections of Atrial Fibrillation by an Implantable Loop Recorder, available at https://cslide-us.ctimeetingtech.com/hrs20/attendee/eposter/file/195#1 (retrieved Jul. 23, 2021).
Mnih, et al., Recurrent Models of Visual Attention, arXiv:1406.6247v1:1406.6247 (Jun. 2014).
"Neural Nets and Noise Filtering", Dr. Dobb's Journal, pp. 32 (Jan. 1989).
Noda, et al., Audio-Visual Speech Recognition using Deep Learning, Applied Intelligence, 42(4):722-737, (Jun. 2015).
Nowlan, et al., A Convolutional Neural Network Hand Tracker, *Advances in Neural Information Processing Systems* 7, (pp. 901-908) (Jan. 1995).
Pan, et al., A Real-Time QRS Detection Algorithm, *IEEE Transactions on Biomedical Engineering*, 3:230-236 (Mar. 1985).
Pigoli, et al., Wavelets in Functional Data Analysis: Estimation of Multidimensional Curves and their Derivatives, Computational Statistics & Data Analysis, 56(6):1482-1498 (Jun. 2012).
Portet, F., P Wave Detector with PP Rhythm Tracking: Evaluation in Different Arrhythmia Contexts, *Physiological Measurement*, 29(1):141-155 (Jan. 2008).
Prineas et al., The Minnesota Code Manual of Electrocardiographic Findings, Springer, Second Edition, ISBN 978-1-84882-777-6, 2009, Minneapolis, Minnesota, US.
Raghunath, et al., Deep Neural Networks Can Predict New-Onset Atrial Fibrillation From the 12-Lead ECG and Help Identify Those at Risk of Atrial Fibrillation-Related Stroke, Circulation, 143(13):1287-98 (Mar. 2021).
Ravichandran, et al., Novel Tool for Complete Digitization of Paper Electrocardiography Data, *IEEE Journal of Translational Engineering in Health and Medicine, Medical Imaging and Diagnostic Radiology*, 1:1800107 (Jun. 2013).
Rodrigues, et al., A Neural Network Approach to ECG Denoising, arXIV preprint arXiv:1212-5217 (Dec. 2012).
Rosenblatt, The Perceptron: A Probabilistic Model for Information Storage and Organization in the Brain, Psychological Review, 65(6):386-408 (Nov. 1958).
Russakovsky, et al., "ImageNet Large Scale Visual Recognition Challenge," *International Journal of Computer Vision*, 115(3): 211 -252 (Dec. 2015).
Saini, et al., Automated ECG Delineation using Machine Learning Algorithms, International Congress on Electrocardiology, Jalandhar, India, 2014, (pp. 1-4).
Schluter, et al., Improved Musical Onset Detection With Convolutional Neural Networks, IEEE International Conference on Acoustics, Speech, and Signal Processing (ICASSP), (pp. 6979-6983) (May 2014).
Shen, et al., Multi-Lead ECG Classification Based on Independent Component Analysis and Support Vector Machine, 3rd International Conference on Biomedical Engineering and Informatics (BMEI), 3:960-964 (Oct. 2010).
Simonyan, et al., Very Deep Convolutional Networks for Large-Scale Image Recognition, arXivpreprint arXiv:1409.1556 (Sep. 2014).
Smith, et al., Improved Interpretation of Atrial Dysrhythmias by a New Neural Network Electrocardiogram Interpretation Algorithm, Academic Emergency Medicine, vol. 24, S1, Abstract 670 (May 2017).
Smith, et al., A deep neural network for 12-lead electrocardiogram interpretation outperforms a conventional algorithm, and its physician overread, in the diagnosis of atrial fibrillation, IJC Heart & Vasculature, 25:100423 (Dec. 1029).
Smith, et al., A deep neural network learning algorithm outperforms a conventional algorithm for emergency department electrocardiogram interpretation, Journal of Electrocardiology, 52:88-95 (Jan. 2019).
Statement of Validation and Accuracy for the Glasgow 12-Lead ECG Analysis Program, Physio Control, Mar. 2009, Redmond, WA USA.
Tun, et al., Analysis on conversion process from paper record ECG to computer based ECG, *MOJ Applied Bionics and Biomechanics*, 1(2):69-81 (2017).
Vaessen., An approach to ECG Delineation using Wavelet Analysis and Hidden Markov Models, Universiteit Maastricht Institute of Instrument Development Engineering & Evaluation Master Thesis, (Sep. 2006).
Zeiler, Matthew D., Adadelta: An Adaptive Learning Rate Method, arXivpreprint arXiv:1212.5701 (Dec. 2012).
Zhang et al., Improving Object Detection with Deep Convolutional Networks via Bayesian Optimization and Structured Prediction, *Proceedings of the IEEE Conference on Computer Vision and Pattern Recognition*, (pp. 249-258) (2015).
Zheng, et al., Time Series Classification Using Multi-Channels Deep Convolutional Neural Networks, *International Conference on Web-Age Information Management*, (pp. 298-310), (Jun. 2014).
U.S. Appl. No. 14/924,239 / U.S. Pat. No. 10,426,364, filed Oct. 27, 2015 / Apr. 27, 2017.
U.S. Appl. No. 15/771,807 / U.S. Pat. No. 10,779,744, filed Apr. 27, 2018 / Sep. 22, 2020.
U.S. Appl. No. 16/267,380 / U.S. Pat. No. 10,959,660, filed Feb. 4, 2019 / Mar. 30, 2021.
U.S. Appl. No. 16/328,701, filed Feb. 26, 2019.
U.S. Appl. No. 16/367,227 / U.S. Pat. No. 10,827,938, filed Mar. 27, 2019 / Nov. 10, 2020.
U.S. Appl. No. 16/522,648 / U.S. Pat. No. 10,758,139, filed Jul. 26, 2019 / Sep. 1, 2020.
U.S. Appl. No. 17/023,977, filed Sep. 17, 2020.
U.S. Appl. No. 17/209,129, filed Mar. 22, 2021.
U.S. Appl. No. 17/390,714, filed Jul. 30, 2021.
International Search Report & Written Opinion dated Jan. 14, 2022 in Int'l PCT Patent Appl. Serial No. PCT/IB2021/0058958 (0910).
International Search Report & Written Opinion dated Jan. 31, 2022 in Int'l PCT Patent Appl. Serial No. PCT/IB2021/057341 (0810).

* cited by examiner

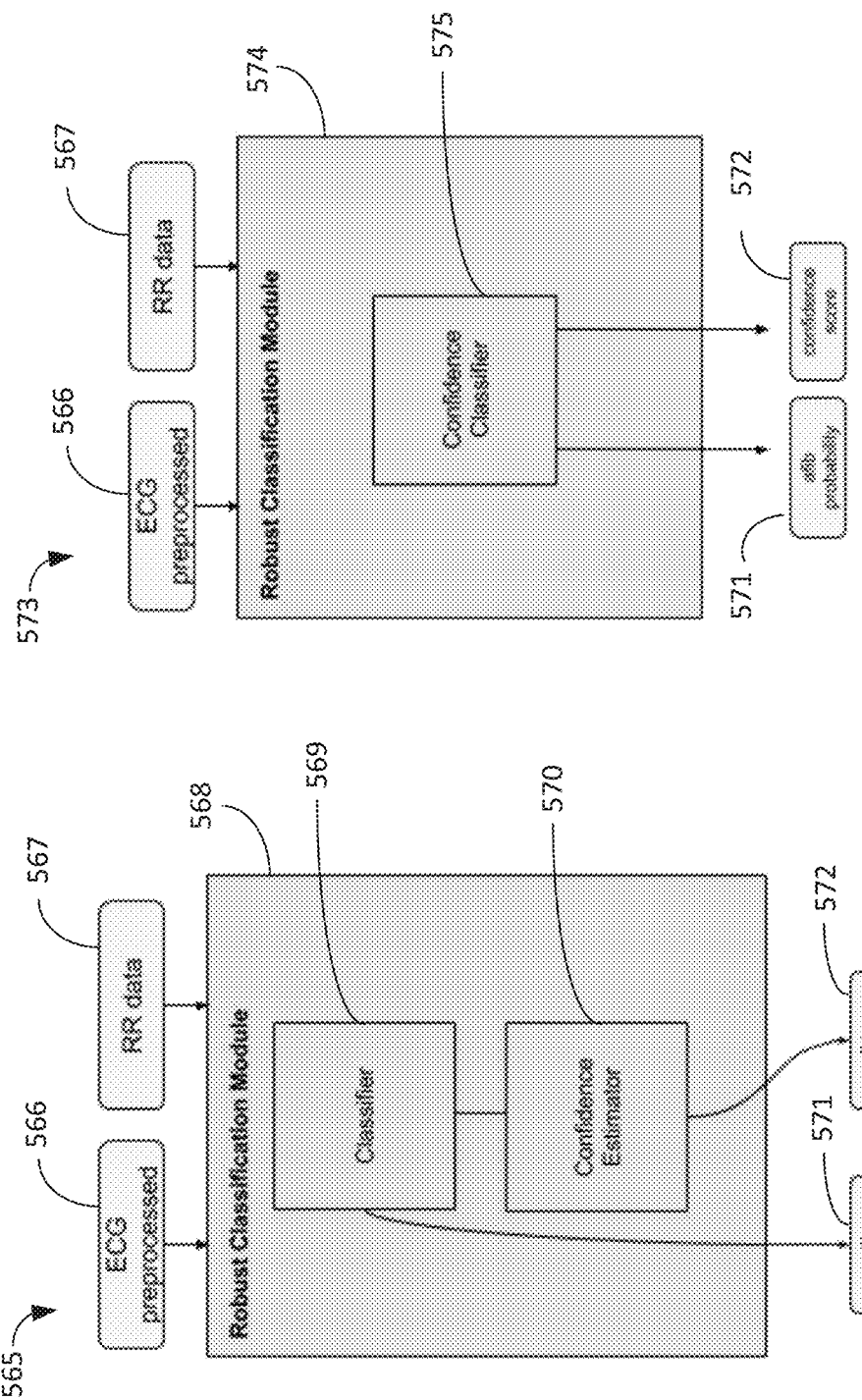

ELECTROCARDIOGRAM PROCESSING SYSTEM FOR DETECTING AND/OR PREDICTING CARDIAC EVENTS

CROSS-REFERENCE TO RELATED APPLICATIONS

This application claims priority to European Patent Application No. EP20306566.9, filed Dec. 15, 2020, and U.S. Provisional Patent Application Ser. No. 63/063,899, filed Aug. 10, 2020, the entire contents of each of which are incorporated herein by reference.

TECHNICAL FIELD

The present disclosure relates, in general, to an electrocardiogram (ECG) processing system, for example, an ECG system with artificial intelligence and machine learning functionality for detecting and/or predicting cardiac events such as arrhythmias and abnormalities.

BACKGROUND

An electrocardiogram (ECG) receives electrical cardiac signals from the heart that may be digitized and recorded by a computing device. An ECG typically is generated from cardiac signals sensed by a number of electrodes placed in specific areas on a patient. It is a simple, non-invasive tool, that may be used by most any healthcare professional.

A cardiac signal is composed of one or multiple synchronized temporal signals. FIG. 1A illustrates a recording of a standard 12-lead resting ECG. As is shown in FIG. 1A, each lead generates an electrical signal, resulting in 12 electrical signals. Though the ECG illustrated in FIG. 1A involves 12 leads resulting in 12 recordings, some ECGs may involve fewer leads resulting in fewer recordings. As is shown in FIG. 1A, a cardiac signal displays repeating patterns usually comprising a P-wave, a QRS complex, and a T-wave. As the name suggests, a QRS complex includes a Q-wave, an R-wave and an S-wave. An exemplary P-wave, QRS complex, and T-wave is illustrated in FIG. 1B, which focuses on a couple of beats in one lead signal, showing one R-R interval.

To make a diagnosis, a trained healthcare professional may analyze the ECG recording to identify any abnormalities and/or episodes. It is estimated that about 150 measurable abnormalities may be identified on an ECG recordings today. However, specific expertise and/or training is required to identify abnormalities from an ECG. ECG analysis is only available to those patients that can afford healthcare professions having the appropriate expertise and who otherwise have access to these professionals.

Telecardiology centers have been developed to provide ECG analysis to patients that may not otherwise have access to these trained healthcare professionals. Typically, an ECG recording is generated offsite by a non-specialist and is sent to the telecardiology center for analysis by a cardiologist or by a specialized ECG technician. While the results are generally high quality, the process may be slow and expensive.

Software systems have also been developed as an alternative to analysis by a trained professional. Current software systems provide a low quality interpretation that often results in false positives. Today, these interpretation systems may generate two types of information about a cardiac signal, (1) temporal location information for each wave, referred to as delineation, and (2) global information providing a classification of the cardiac signal or labeling its abnormalities, referred to as classification.

Concerning delineation, two main approaches are used for finding the waves of cardiac signals. The first approach is based on multiscale wavelet analysis. This approach looks for wavelet coefficients reaching predefined thresholds at specified scales. (See Martinez et al., A wavelet-based ECG delineator: evaluation on standard databases, IEEE transactions on biomedical engineering, Vol. 51, No. 4, April 2004, pp. 570-58; Almeida et al., IEEE transactions on biomedical engineering, Vol. 56, No. 8, August 2009, pp 1996-2005; Boichat et al., Proceedings of Wearable and Implantable Body Sensor Networks, 2009, pp. 256-261; U.S. Pat. No. 8,903,479 to Zoicas et al.). The usual process involves identifying QRS complexes, then P-waves, and finally T-waves. This approach is made unstable by the use of thresholds and fails to identify multiple P-waves and "hidden" P-waves.

The second delineation approach is based on Hidden Markov Models (HMM). This machine learning approach treats the current state of the signal as a hidden variable that one wants to recover (Coast et al., IEEE transactions on biomedical engineering, Vol. 37, No. 9, September 1990, pp 826-836; Hughes et al., Proceedings of Neural Information Processing Systems, 2004, pp 611-618; U.S. Pat. No. 8,332,017 to Trassenko et al.). While this approach is an improvement upon on the first delineation approach described above, a representation of the signal must be designed using handcrafted "features," and a mathematical model must be fitted for each wave, based on these features. Based on a sufficient number of examples, the algorithms may learn to recognize each wave. This process may however be cumbersome and inaccurate due to its dependence on handcrafted features. Specifically, features which have been handcrafted will always be suboptimal since they were not learnt and the process of handcrafting features may have ignored or eliminated crucial information. Further, the model, usually Gaussian, is not well adapted. Also, the current models fail to account for hidden P waves.

Regarding classification, in current systems analysis is only performed on the QRS complex. For example, analysis of a QRS complex may detect ventricular or paced beats. The training involves handcrafted sets of features and corresponding beat labels (Chazal et al., IEEE Transactions on Biomedical Engineering, 2004, vol. 51, pp. 1196-1206). As explained above, features that have been handcrafted will always be suboptimal since they were not learnt and the process of handcrafting features may have ignored or eliminated crucial information.

To solve the above issues, recent works (Kiranyaz et al., IEEE Transactions on Biomedical Engineering, 2016, Vol. 63, pp 664-675) have turned to novel architectures called neural networks which have been intensively studied and had great results in the field of imaging (Russakovsky et al., arXiv: 1409.0575v3, 30 Jan. 2015). Neural networks learn from raw or mildly preprocessed data and thus bypass the need of handcrafted features. While the application of neural networks is an improvement on the delineation and classification approaches described above, current systems have certain drawbacks. For example, the current neural networks were only developed for QRS characterization. Further, current neural networks processes information in a beat-by-beat manner which fails to capture contextual information from surrounding beats.

Concerning identifying abnormalities and/or cardiovascular disease detection, most algorithms use rules based on temporal and morphological indicators computed using the delineation (e.g., PR interval, RR interval, QT interval, QRS width, level of the ST segment, slope of the T-wave). Often times, the algorithms are designed by cardiologists. (Prineas et al., The Minnesota Code Manual of Electrocardiographic Findings, Springer, ISBN 978-1-84882-777-6, 2009). However, the current algorithms do not reflect the way the cardiologists analyze the ECGs and are crude simplifications. For example, the Glasgow University Algorithm does not reflect the way cardiologist analyze ECGs. (Statement of Validation and Accuracy for the Glasgow 12-Lead ECG Analysis Program, Physio Control, 2009.)

More advanced methods have also been developed that use learning algorithms. In Shen et al., Biomedical Engineering and Informatics (BMEI), 2010. vol. 3, pp. 960-964, for instance, the author used support vector machines to detect bundle branch blocks. However, in these methods, once again, it is necessary to represent the raw data in a manner that preserves the invariance and stability properties.

While more complex neural network architectures have been proposed, limitations arose when they were applied to ECGs. One team (Jin and Dong, Science China Press, Vol. 45, No 3, 2015, pp 398-416; CN104970789) proposed binary classification on a full ECG, hence providing one and only one classification for any analyzed ECG. The proposed architecture used convolutional layers which processes the leads independently before mixing them into fully connected layers. The authors also mention multi-class analysis, as opposed to binary analysis, aiming at recovering one class among several. However, they did not consider multi-label classification, wherein multiple labels (e.g., abnormalities) are assigned to a cardiac signal.

Other algorithms and neural network architectures have been proposed to detect the risk of atrial fibrillation. However, such algorithms and neural networks often require 12-leads and recordings over long periods of time. Also, typically such predications are long term predictions (e.g., one year). In Attia et al., "An artificial intelligence-enabled ECG algorithm for the identification of patients with atrial fibrillation during sinus rhythm: a retrospective analysis of outcome prediction," The Lancet, Volume 394, Issue 10201, P 861-867, Sep. 7, 2019, the entire contents of which are incorporated herein by reference, the author describes using artificial intelligence and convolutional neural networks to detect asymptomatic atrial fibrillation. In Christopoulos et al., "Artificial Intelligence-Electrocardiography to Predict Incident Atrial Fibrillation" Circ Arrhythm Electrophysiol, Volume 13, No. 12, December 2020, the entire contents of which are incorporated herein by reference, the author describes determining a probability of atrial fibrillation using artificial intelligence algorithms applied to electrocardiography during sinus rhythms. In Raghunath et. al., "Deep Neural Networks Can Predict New-Onset Atrial Fibrillation From the 12-Lead ECG and Help Identify Those at Risk of Atrial Fibrillation-Related Stroke," Circulation, Volume 143, No. 13, Mar. 30, 2021, the entire contents of which are incorporated herein by reference, the author describes determining a prediction of atrial fibrillation onset from a resting 12-lead ECG.

In view of the foregoing limitations of previously-known systems and methods, it would be desirable to accurately and efficiently process ECG data and to present this information in a way that is easily comprehendible. For example, it would be desirable to use enhanced computing technology to analyze ECG data sampled from a patient to accurately and efficiently detect and/or predict cardiac events, e.g., using artificial intelligence and/or machine learning technology specifically designed for ECG analysis.

SUMMARY OF THE INVENTION

Provided herein are systems and methods for analyzing ECG data using machine learning algorithms and medical grade artificial intelligence with enhanced accuracy and efficiency. Specifically, systems and methods are provided for analyzing electrocardiogram (ECG) data of a patient using artificial intelligence and a substantial amount of ECG data. The systems receive ECG data from a sensing device positioned on a patient such as one or more ECG leads/electrodes that may be integrated into smart technology (e.g., a smartwatch). The system may analyze ECG data sampled from the patient to accurately and efficiently detect and/or predict cardiac events such as such as cardiac arrhythmias and/or abnormalities including atrial fibrillation (AFib). The system may include an application that communicates with an ECG platform running on a server that processes and analyzes the ECG data, e.g., using neural networks for delineation of the cardiac signal and classification of various abnormalities, conditions and/or descriptors. The ECG platform may be a cloud-based ECG platform that processes and analyzes the ECG data in the cloud. The processed ECG data is communicated from the server for display in a user-friendly and interactive manner with enhanced accuracy. Together the ECG application and ECG platform implement the ECG processing system to receive ECG data, process and analyze ECG data, display ECG data on a system device, and generate a report having ECG data.

A computerized-system is provided herein for analyzing ECG data of a patient generated by one or more electrodes across a plurality of time points and comprising a plurality of beats. The computerized-system may be designed to analyze the ECG data using a delineation algorithm to generate wave information corresponding to a likelihood of a presence of at least one wave at the plurality of time points and further to determine beat onset information and beat offset information for beats of the plurality of beats where at least one wave is determined to be present to generate a plurality of beat onsets and beat offsets. The computerized system may further be designed to extract a plurality of beat portions of ECG data based on the plurality of beat onsets and beat offsets, each beat portion of the plurality of beat portions of ECG data corresponding to a beat of the plurality of beats, and determine that at least two beats of the plurality of beats should be grouped together based on the plurality of beat portions of ECG data, the at least two beats forming a cluster. Determining that the at least two beats of the plurality of beats should be grouped together may involve determining that the group data satisfies a threshold value.

The computerized-system may further be designed to analyze the plurality of portions of ECG data using an embedding algorithm to generate embedding data representative of the plurality of beats, and analyze the embedding data using a grouping algorithm to generate group data. The at least two beats of the plurality of beats may be determined to be grouped together based on the group data. The group data may correspond to a distance between two beats. The delineation algorithm may utilize a first neural network and the embedding algorithm may utilize a second neural network. The grouping algorithm may utilize a third neural network. The computerized-system may further be designed to receive user input data from an input device regarding an inaccuracy corresponding to displayed data related to the ECG data. The computerized-system may further be designed to adjust one or more of the delineation algorithm, embedding algorithm, or grouping algorithm based on the user input data.

The computerized-system may further be designed to modify the displayed data based on the user input data. The user input data may correspond to adding, deleting, or splitting one or more QRS clusters, PVC clusters, or PAC clusters. The embedding data may involve a vector of data for each beat of the plurality of beats. The computerized-system may further be designed to transmit information indicative of the cluster to a computer for display on a graphic user interface. The computerized-system may further be designed to generate information to display at least one overlay comprising at least two beats of the plurality of beats overlaid over one another. The computerized-system may further be designed to analyze the beats in the cluster using a classification algorithm to determine a likelihood of a presence of the one or more abnormalities, conditions, or descriptors associated with cardiac events for the patient.

The computerized-system may further be designed to analyze the wave information from the delineation algorithm using a classification algorithm to determine a likelihood of a presence of the one or more abnormalities, conditions, or descriptors associated with cardiac events for the patient. The wave information may be inputted into the classification algorithm and separately used to determine that at least two beats of the plurality of beats should be grouped together. The computerized-system may further be designed to, prior to analyzing the ECG data using the delineation algorithm, pre-process the ECG data to remove noise from the ECG data. The computerized-system may assign the ECG data and information based on the ECG data to a user account for review. The computerized may receive user input data regarding the ECG data and information based on the ECG data from the user account based on the review.

A method for analyzing electrocardiogram (ECG) data of a patient generated by one or more electrodes across a plurality of time points and comprising a plurality of beats is described herein. The method may involve analyzing the ECG data using a delineation algorithm to generate wave information corresponding to a likelihood of a presence of at least one wave at the plurality of time points, and determining beat onset information and beat offset information for beats of the plurality of beats where at least one wave is determined to be present to generate a plurality of beat onsets and beat offsets. The method may further involve extracting a plurality of beat portions of ECG data based on the plurality of beat onsets and beat offsets, each beat portion of the plurality of beat portions of ECG data corresponding to a beat of the plurality of beats, and determining that at least two beats of the plurality of beats should be grouped together based on the plurality of beat portions of ECG data, the at least two beats forming a cluster.

The method may further involve analyzing the plurality of portions of ECG data using an embedding algorithm to generate embedding data representative of the plurality of beats, and analyzing the embedding data using a grouping algorithm to generate group data. The at least two beats of the plurality of beats may be determined to be grouped together based on the group data. The method may further involve assigning the ECG data and information based on the ECG data to a user account for review of the ECG data. The method may further involve submitting the ECG data and information based on the ECG data for quality review by one or more reviewers. The method may further involve receiving quality control input generated by the one or more reviewers. The method may further involve causing display of the quality control input for additional quality control review. The method may further involving receiving user input data from an input device regarding an inaccuracy corresponding to information based on the ECG data. The method may further involve adjusting one or more of the delineation algorithm, embedding algorithm, or grouping algorithm based on the user input data. The method may further involve assigning the displayed data to a user account for quality review.

A system for analyzing ECG data of a patient may, in one example, involve a first plurality of instructions designed to, when executed, obtain ECG data of the patient over a plurality of time points and may further cause transmission of the ECG data to at least one server. The ECG data may be sampled at a predetermined sampling rate such as a rate of at least 20 samples per second. The system for analyzing ECG data may further involve a second plurality of instructions designed to, when executed, cause the at least one server to receive the ECG data of the patient, analyze the ECG data of the patient using at least one algorithm trained from a plurality of ECG data sets from different patients, quantify a likelihood of a presence of one or more abnormalities, conditions, or descriptors, or any combination thereof, and transmit information corresponding to the presence of the one or more abnormalities, conditions, or descriptors, or any combination thereof, to a computer remote from the at least one server for display.

The system for analyzing ECG data may further involve a third plurality of instructions designed to, when executed by the computer, cause the computer to display information corresponding the presence of the one or more abnormalities, conditions, or descriptors, or any combination thereof, based on the transmitted information from the at least one server. It is understood that each set of the plurality of ECG data sets from the different patients may be generated at a sampling rate equal to the rate used to obtain the ECG data. It is further understood that the computer that executes the third plurality of instructions may also execute the first plurality of instructions.

The second plurality of instructions may, when executed, further cause the at least one server to pre-process the ECG data which may involve removing noise from the ECG data or expressing the ECG data at a predetermined baseline frequency. Further, the second plurality of instructions, when executed, may analyze the ECG data of the patient using at least one algorithm that applies the ECG data to a first neural network for delineation and may further quantify a likelihood of a presence of at least one of a P-wave, QRS complex, or T-wave at each of the plurality of time points. The second plurality of instructions may further calculate at least one onset and at least one offset for at least one of the P-wave, QRS-complex, or T-wave, and/or calculate at least one measurement from one or more of the onset, the offset, or the output of the first neural network.

It is further understood that the second plurality of instructions may, when executed, analyze the ECG data of the patient using at least one algorithm that applies the ECG data to a second neural network for classification. Specifically, the second plurality of instructions may quantify a likelihood of a presence of the one or more abnormalities, conditions, or descriptors, and may apply a threshold to at least one value in the output of the second neural network and assign at least one label corresponding to the one or more abnormalities, conditions, or descriptors if the value exceeds a threshold. The second plurality of instructions may also post-process the ECG data by removing redundant labels.

The system may further include a fourth and/or fifth plurality of instructions. The fourth plurality of instructions may, when executed, cause the at least one server to generate a report including at least the transmitted information corresponding to the presence of the one or more abnormalities, conditions, or descriptors. The fifth plurality of instructions may, when executed, receive user input related to the ECG data and cause the computer to transmit the user input to the at least one server such that the at least one server uses the user input to generate the report. The report may include at least one heart rate density plot representing density of heart rates of the patient as a function of time. It is understood that a third plurality of instructions is further configured to, when executed by the computer, cause the computer to display a heart rate density plot representing density of heart rates of the patient as a function of time.

A system for analyzing ECG data of a patient may, in another example, involve instructions stored on at least one server that are designed to, when executed, cause the at least one server to receive a set of ECG data of the patient over a plurality of time points. The set of ECG data may be sampled at a predetermined sampling rate such as a rate of at least 20 samples per second. The instructions may further be designed to cause the at least one server to analyze the set of ECG data of the patient using at least one algorithm, quantify, at each time point of the plurality of time points, a likelihood of a presence of one or more abnormalities, conditions, or descriptors, or any combination thereof and transmit information corresponding to the likelihood of the presence of the one or more abnormalities, conditions, or descriptors to a computer for display. The at least one algorithm may be trained using a plurality of sets of ECG data generated at a sampling rate of at least 20 samples per second from different patients.

A computerized-method for analyzing ECG data of a patient may similarly involve receiving a set of ECG data of the patient over a plurality of time points sampled at a sample rate and analyzing the set of ECG data of the patient using at least one algorithm trained using a plurality of sets of ECG data. Each set in the plurality of sets of ECG data may be generated at the same sample rate from different patients. The computerized method for analyzing ECG data may further involve identifying, at each time point, one or more abnormalities, conditions or descriptors, or any combination thereof and further may involve transmitting information including the one or more abnormalities, conditions, or descriptors, or any combination thereof to a computer for display. It is understood that the computerized-method may involve analyzing an entire set of sampled ECG data without discarding data from the set of ECG data. The computerized-method may, in one example, involve a sample rate of at least 20 samples per second.

The computerized-method may further involve assigning the set of ECG data and information based on the set of ECG data to a user account for review of the ECG data. The computerized-method may further involve submitting the set of ECG data and information based on the set of ECG data for quality review by one or more reviewers. The computerized-method may further involve receiving quality control input generated by the one or more reviewers. The method may further involve causing display of the quality control input for additional quality control review.

A computerized-system for analyzing electrocardiogram (ECG) data of a patient may, in another example, include a computerized-system to analyze the ECG data to determine a presence of a cardiac event. If the cardiac event is determined to be present based on the analysis of the ECG data, the computerized-system may generate information to identify the presence of the cardiac event for display. If the cardiac event is determined not to be present based on the analysis of the ECG data, the computerized-system may further analyze the ECG data to determine a risk score indicative of future risk of the cardiac event for display. The cardiac event may be atrial fibrillation.

The computerized-system may further perform delineation on the ECG data to determine a plurality of beats, extract a plurality of first features from the plurality of beats, and determine a first risk score based on the plurality of first features. The first risk score may be indicative of future atrial fibrillation for the patient. Performing delineation on the ECG data may determine a plurality of QRS onset values. The computerized-system may further perform classification on the ECG data to classify beats of the plurality of beats as normal, premature atrial complexes (PAC) or premature ventricular complexes (PVC), determine a plurality of timestamps corresponding to the plurality of beats, determine a plurality of heat rate values based on the plurality of timestamps, determine a matrix based on the plurality of timestamps and the plurality of heart rate values, generate a graphical representation of the matrix, and process the graphical representation of the matrix using at least one neural network to determine a second a second risk score indicative of future atrial fibrillation for the patient.

At least one neural network is at least one deep neural network (DNN). The computerized-system may further determine patient information corresponding to the patient, determine a plurality of second features of the ECG data indicative of atrial fibrillation, and apply the plurality of second features to a classifier to determine a third score value indicative of future atrial fibrillation for the patient. The patient information may be one or more of age and sex of the patient. The classifier is one or more of DNN, logistic regression, and a Random Forest. The computerized-system may determine an average of the first risk score, the second risk score, and the third risk score to determine the risk score. The computerized-system may be further configured to apply the first risk score, the second risk score, and the third risk score to a first neural network trained to determine the risk score.

A computerized-system for analyzing ECG data of a patient may, in another example, analyze the ECG data using a delineation algorithm to determine a likelihood of a presence of at least one wave and may analyze the ECG data using a classification algorithm to extract a plurality of feature maps corresponding to the ECG data. The computerized-system may further apply the plurality of feature maps to a recurrent neural network and analyze the plurality of feature maps using the recurrent neural network to determine a sequence label corresponding to a first beat based, at least in part, on a feature map of the plurality of feature maps indicative of a second beat occurring immediately before the first beat. The sequence label may be one of ectopic, supraventricular, or PVC.

A computerized-system for analyzing ECG data of a patient may, in another example, analyze the ECG data using a delineation algorithm to determine wave information indicating a likelihood of a presence of at least one wave and analyze the ECG data and wave information using a baseline classification algorithm. The computerized-system may further determine a first value using the baseline classification algorithm, the first value indicating a presence of at least one cardiac event, and may analyze the ECG data and wave information using a desensitized classification algorithm, the desensitized classification algorithm having decreased sensitivity compared to the baseline classification algorithm. Additionally, the computerized-system may determine a second value using the desensitized classification algorithm, analyze the ECG data and wave information using a sensitive classification algorithm, the sensitive classification algorithm having increased sensitivity compared to the baseline classification algorithm, may determine a third value using the sensitive classification algorithm, and may determine that the baseline classification is certain based on the second value and the third value indicating the presence of the at least one cardiac event. The computerized-system may further automatically generate a report corresponding to the presence of the at least one cardiac event.

A computerized-system for analyzing ECG data of a patient may, in another example, upload ECG data to the computerized-system from a database of ECG data, assign a profile to the ECG data, determine instructions to associate a predetermined label with the ECG data, assign the predetermined label to the profile associated with the ECG data, and determine instructions to filter a plurality of ECG profiles based on the predetermined label, the plurality of profiles including the profile. The computerized-system may further analyze the ECG data to determine a presence of a cardiac event and assign a second label to the profile associated with the ECG data, the second label based on the presence of the cardiac event.

A computerized-system for analyzing ECG data of a patient may, in another example, determine a plurality of ECG data, the plurality of ECG data including first ECG data corresponding to a first lead and second ECG data corresponding to a second lead, cause an ECG interface to display a first graphical representation of at least a portion of the first ECG data, determine instructions to display a second graphical representation of at least a portion of the second ECG data in addition to the first graphical representation, and cause the ECG interface to simultaneously display the second graphical display synced in time with the first graphical display. The computerized-system may further determine third ECG data corresponding to a third lead, the plurality of ECG data further including the third ECG data, may determine instructions to display a third graphical representation of at least a portion of the third ECG data and the second ECG data, and may cause the ECG interface to simultaneously display the third graphical representation synced in time with the second graphical representation.

A computerized-system for analyzing ECG data of a patient may, in another example, analyze the ECG data using a delineation algorithm to determine first information indicating a likelihood of a presence of at least one wave and may analyze the ECG data and the first information using a plurality of classification neural networks. Each of the plurality of classification neural networks may utilize weighted values unique to its classification neural network. The computerized-system may further determine a plurality of outputs using the plurality of classification neural networks. Each output of the plurality of outputs may correspond to a classification neural network of the plurality of classification neural networks. The computerized-system may further analyze the plurality of outputs using a combiner to determine a probability of atrial fibrillation and a confidence score indicative of an accuracy of the probability of atrial fibrillation. The combiner may determines an average value by averaging the plurality of outputs. Alternatively, the combiner may determines a minimum value of the plurality of outputs. In another example, the combiner may determines a maximum value of the plurality of outputs.

A computerized-system for analyzing ECG data of a patient may, in another example, analyze the ECG data using a delineation algorithm to determine first information indicating a likelihood of a presence of at least one wave, may analyze the ECG data and first information using an input transformer to modify the ECG data and generate a plurality of inputs, and may analyze the plurality of inputs using a classification neural network. Further, the computerized-system may determine a plurality of outputs using the classification neural network. Each output of the plurality of outputs may correspond to an input of the plurality of inputs. Further, the computerized-system may analyze the plurality of outputs using a combiner to determine a probability of atrial fibrillation and a confidence score indicative of an accuracy of the probability of atrial fibrillation. The combiner may determine an average value by averaging the plurality of outputs. The combiner may determine a minimum value of the plurality of outputs. The combiner may determine a maximum value of the plurality of outputs. The input transformer may perform an amplification transformation to amplify the ECG data using a float value. The input transformer may perform a dilation transformation to warp the ECG data in time.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

FIGS. 15A-15E illustrate exemplary methods for analyzing ECG data and determining the certainty and/or confidence of the likelihood of the presence of an anomaly and/or condition.

The foregoing and other features of the present invention will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION OF THE INVENTION

The present invention is directed to an electrocardiogram (ECG) processing system having medical grade artificial intelligence involving an ECG application run on a system device and an ECG platform run on a server(s). The ECG application and ECG platform implement the ECG processing system by processing and analyzing the ECG data using machine learning algorithms to detect and/or predict cardiac events such as such as cardiac arrhythmias and/or abnormalities including atrial fibrillation (AFib). The system may achieve delineation of the cardiac signal and classification of various abnormalities, conditions, and descriptors. The server(s) may be located in a different location than the system device(s) and the servers need not be in the same physical location as one another (e.g., the server(s) may be a remote server(s)). Alternatively, the server(s) and the system device(s) may be located in the same general area (e.g., on a local area network (LAN)). The ECG platform may be a cloud-based ECG platform that may implement the ECG processing system by processing and analyzing the ECG data in the cloud.

To implement the ECG processing system, ECG application running on the system device may receive ECG data (i.e., cardiac signal) from a sensing device and may transmit the ECG data to a ECG platform running on the server. The ECG platform may execute a first and second neural network and may apply the ECG data to the first and second neural network. The first neural network may be a delineation neural network having machine learning functionality. The second neural network may be a classification neural network having machine learning functionality. The output of the first and/or second neural networks may be processed by the ECG platform to achieve delineation and classification of the ECG data. The ECG data and/or data generated by the ECG platform may be communicated from the ECG platform to the ECG application. The ECG application may cause the ECG data and/or data generated by the ECG platform to be displayed in an interactive manner. The ECG platform may generate reports including ECG data and/or data generated by the ECG platform, and may communicate the reports to the ECG application.

Figure 1A:
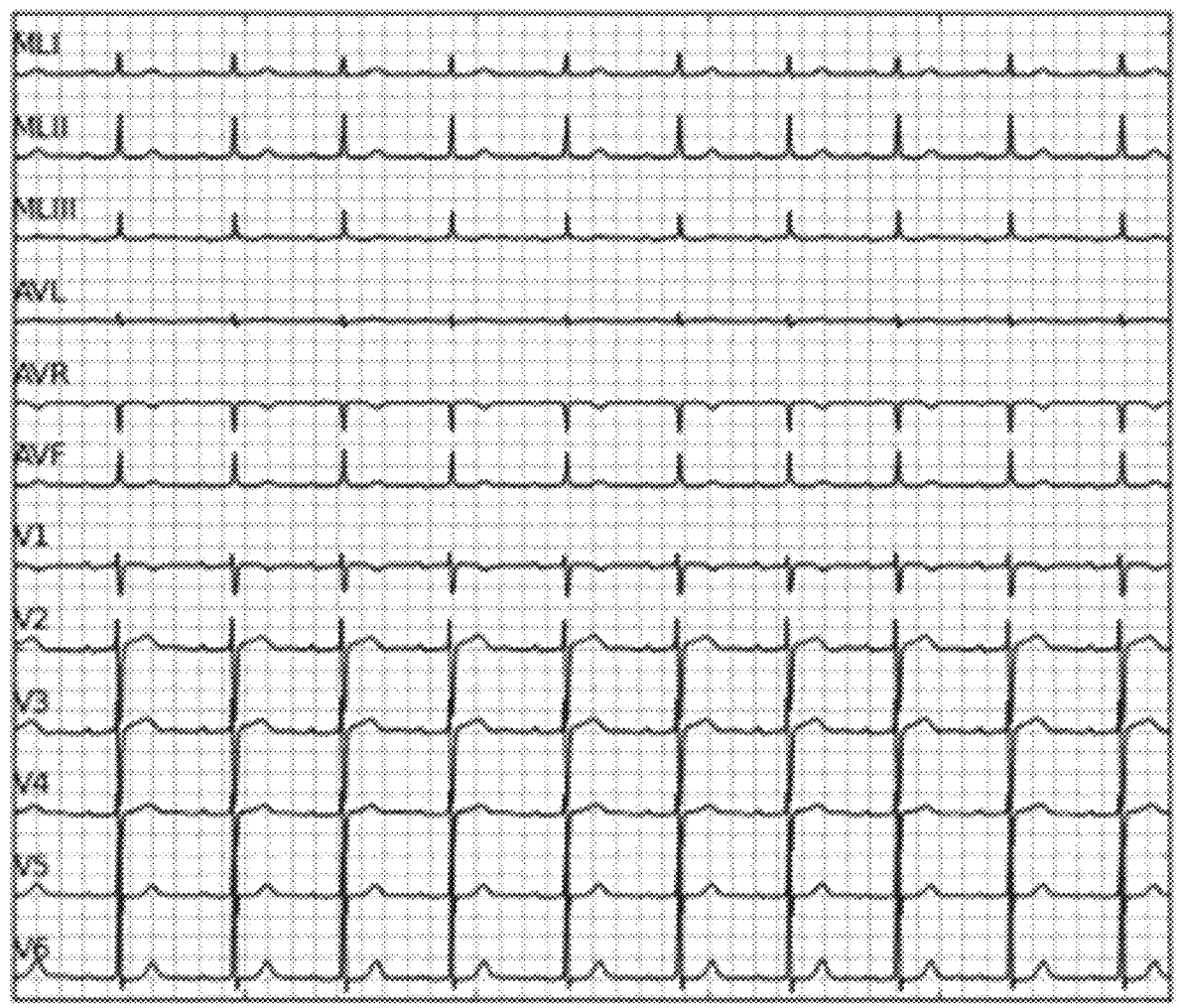
FIG. 1A is a recording of a standard 12-lead resting ECG and FIG. 1B is a recording of an exemplary P-wave, QRS complex and T-wave.
Figure 1B:
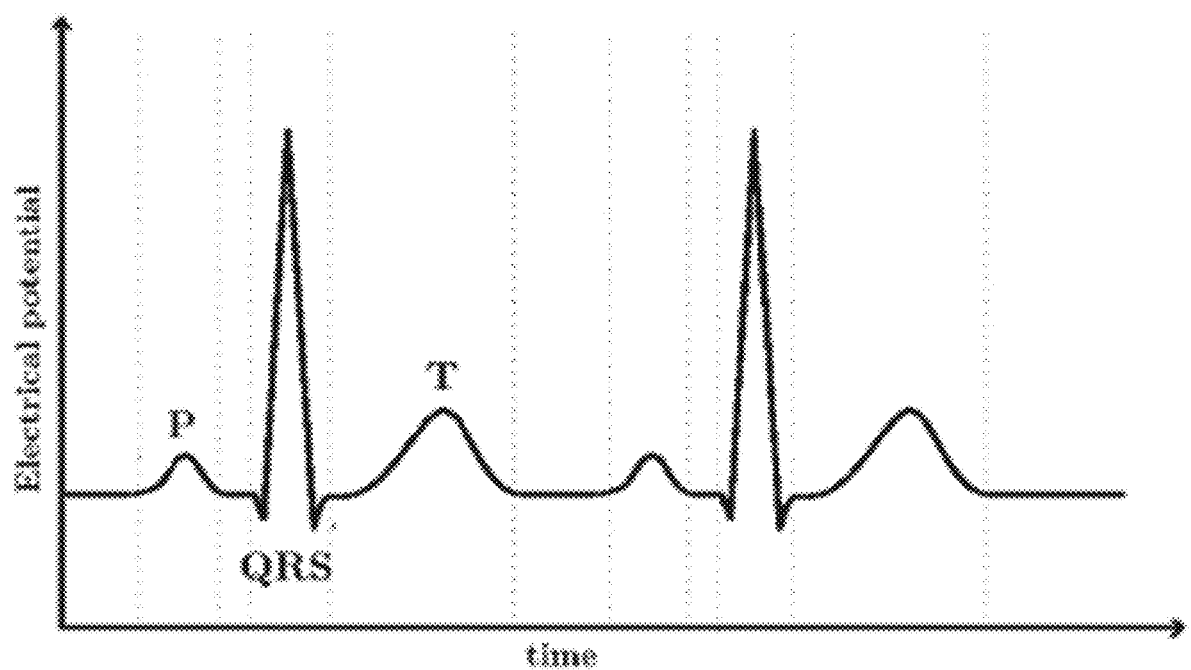
Figure 2:
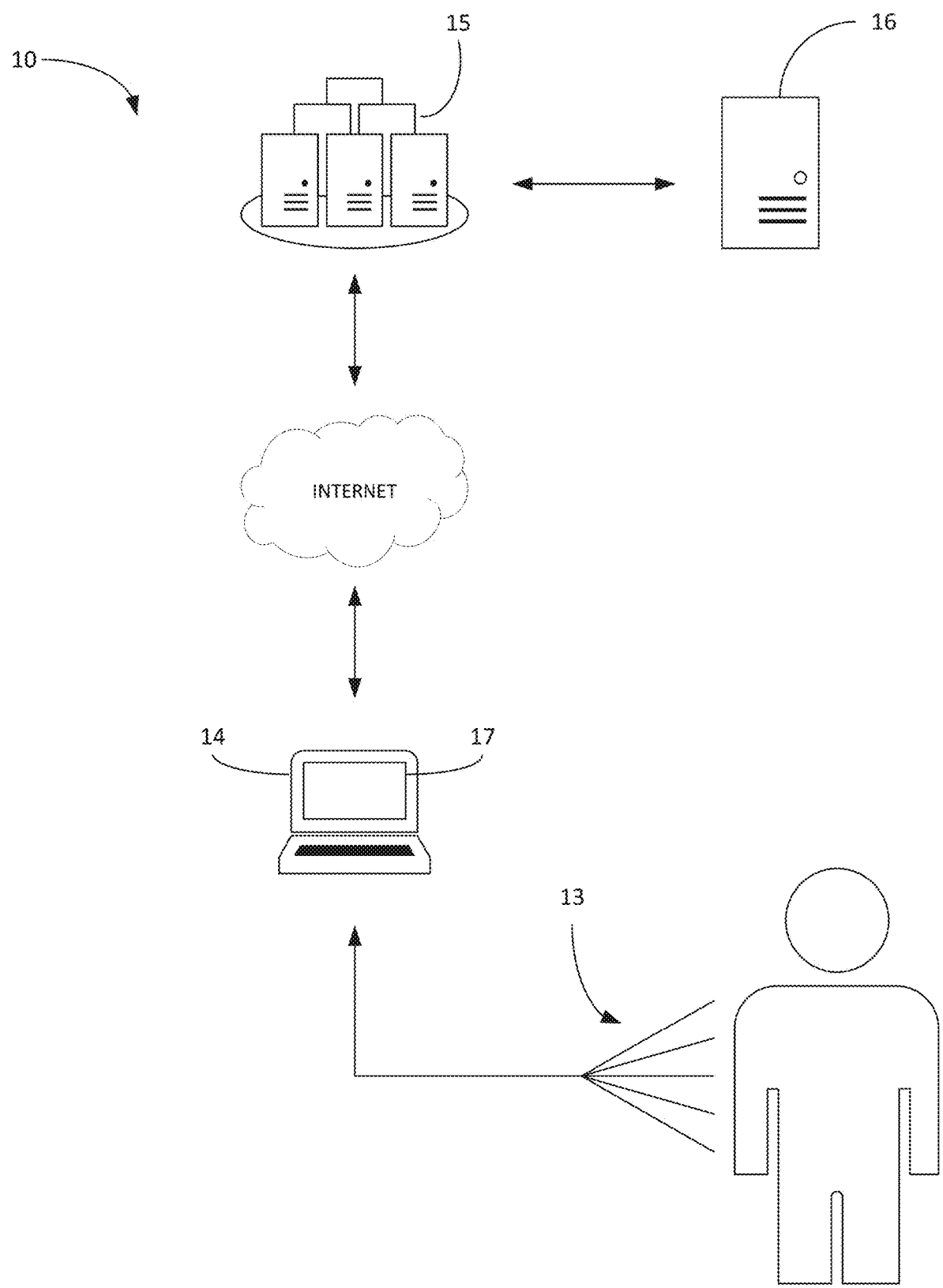
FIG. 2 is a diagram illustrating exemplary components for executing systems and methods in accordance with aspect of the present disclosure.

Referring now to FIG. 2, exemplary components for executing electrocardiogram (ECG) processing system 10 are illustrated. FIG. 2 shows ECG sensing device 13, system device 14, and server 15, as well as drive 16.

ECG sensing device 13 is designed to sense the electrical activity of the heart for generating ECG data. For example, sensing device 13 may be one or more electrodes that may be disposed on one or more leads. ECG sensing device 13 may be an ECG-dedicated sensing device such as a conventional 12-lead arrangement or may be a multi-purposes device with sensing hardware for sensing electrical activity of the heart for ECG generation such as the Apple Watch available from Apple, Inc., of Cupertino, Calif. Sensing device 13 may be placed on the surface of the chest of a patient and/or limbs of a patient. Sensing device 13 may be in electrical communication with system device 14 running the ECG application 29 such that the electrical signal sensed by sensing device 13 may be received by the ECG application 29. ECG application 29 may include instructions that cause sensing device 13 to sense or otherwise obtain ECG data.

System device 14 is preferably one or more computing devices (e.g., laptop, desktop, tablet, smartphone, smartwatch, etc.) having the components described below with reference to FIG. 3A and the functionality described herein. System device 14 running ECG application 29 may connect with server 15 running ECG platform 37 via any well-known wired or wireless connection. For example, system device 14 may connect to the Internet using well known technology (e.g., WiFi, cellular, cable/coaxial, and/or DSL) and may communicate with server 15 over the Internet.

Server 15 is preferably one or more servers having the components described below with reference to FIG. 3B and the functionality described herein. Server 15 preferably has processing power superior to system device 14 such that server 15 can process and analyze cardiac signals having a sampling rate above a predetermined threshold, such as at least 20 samples per second, at least 250 samples per second, or at least 1000 samples per second. As will be readily apparent to one skilled in the art, server 15 may include a plurality of servers located in a common physical location or in different physical locations. In a preferred embodiment, server 15 is located in a different, remote location (e.g., on the cloud) than system device 14, although server 15 and system device 14 may be located in a common location (e.g., on a local area network (LAN)).

Server 15 may optionally communicate with drive 16 which may be one or more drives having memory dedicated to storing digital information unique to a certain patient, professional, facility and/or device. For example, drive 16 may include, but is not limited to, volatile (e.g. random-access memory (RAM)), non-volatile (e.g. read-only memory (ROM)), flash memory, or any combination thereof. Drive 16 may be incorporated into server 15 or may be separate and distinct from server 15 and may communicate with server 15 over any well-known wireless or wired connection.

Aspects of ECG processing system 10 and/or any other ECG processing systems described throughout this application may be the same or similar to the ECG processing system described in WO2020161605A1, which is the published application of PCT/IB2020/050850, filed on Feb. 3, 2020, (corresponding to U.S. Ser. No. 17/390,714), which claims priority to U.S. Pat. No. 10,959,660 to Li, the entire contents of each of which are incorporated herein by reference.

Figure 3A:
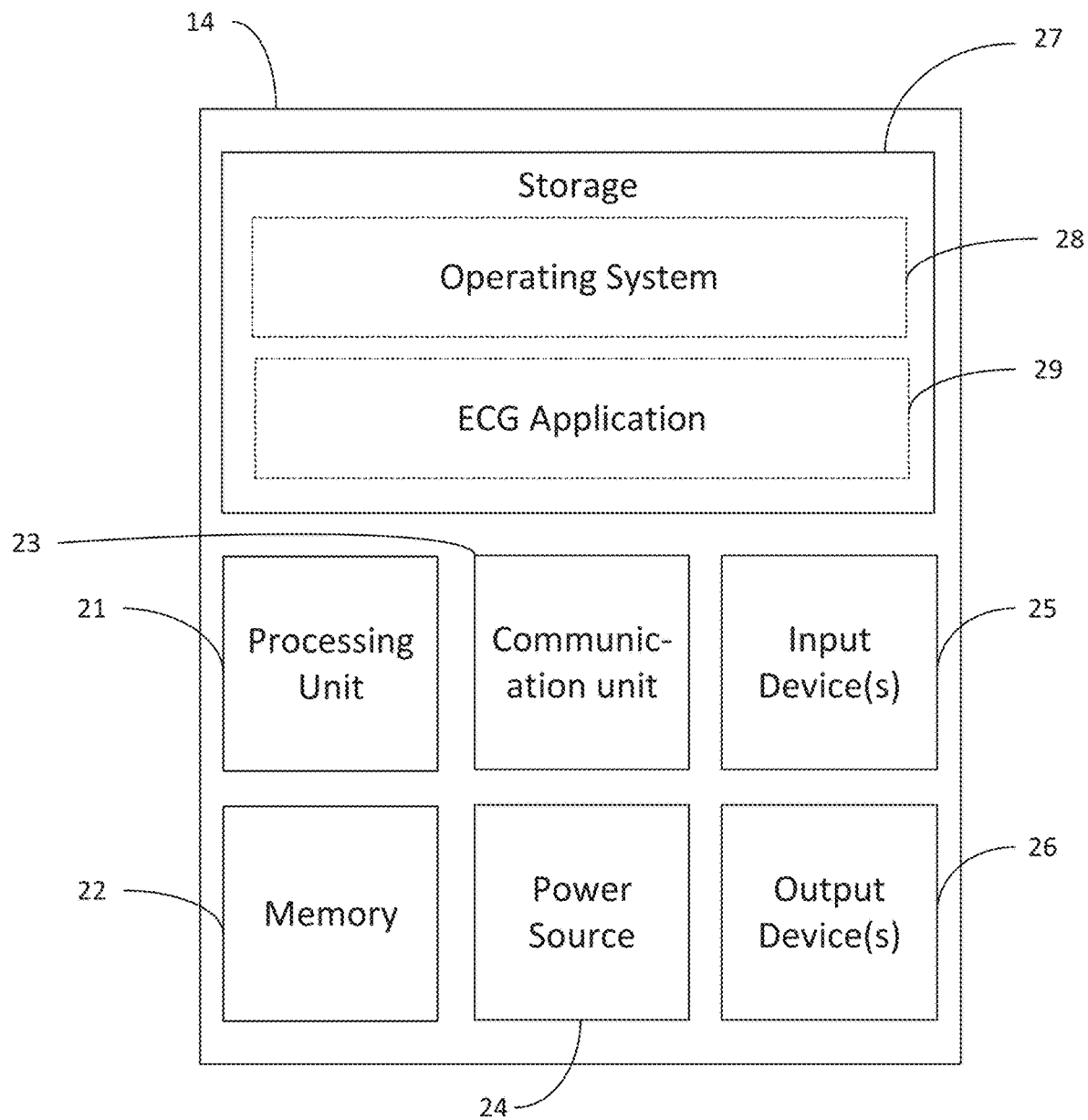
FIGS. 3A-3B are schematic views of the exemplary hardware and software components of an exemplary system device and an exemplary server, respectively.
Figure 3B:
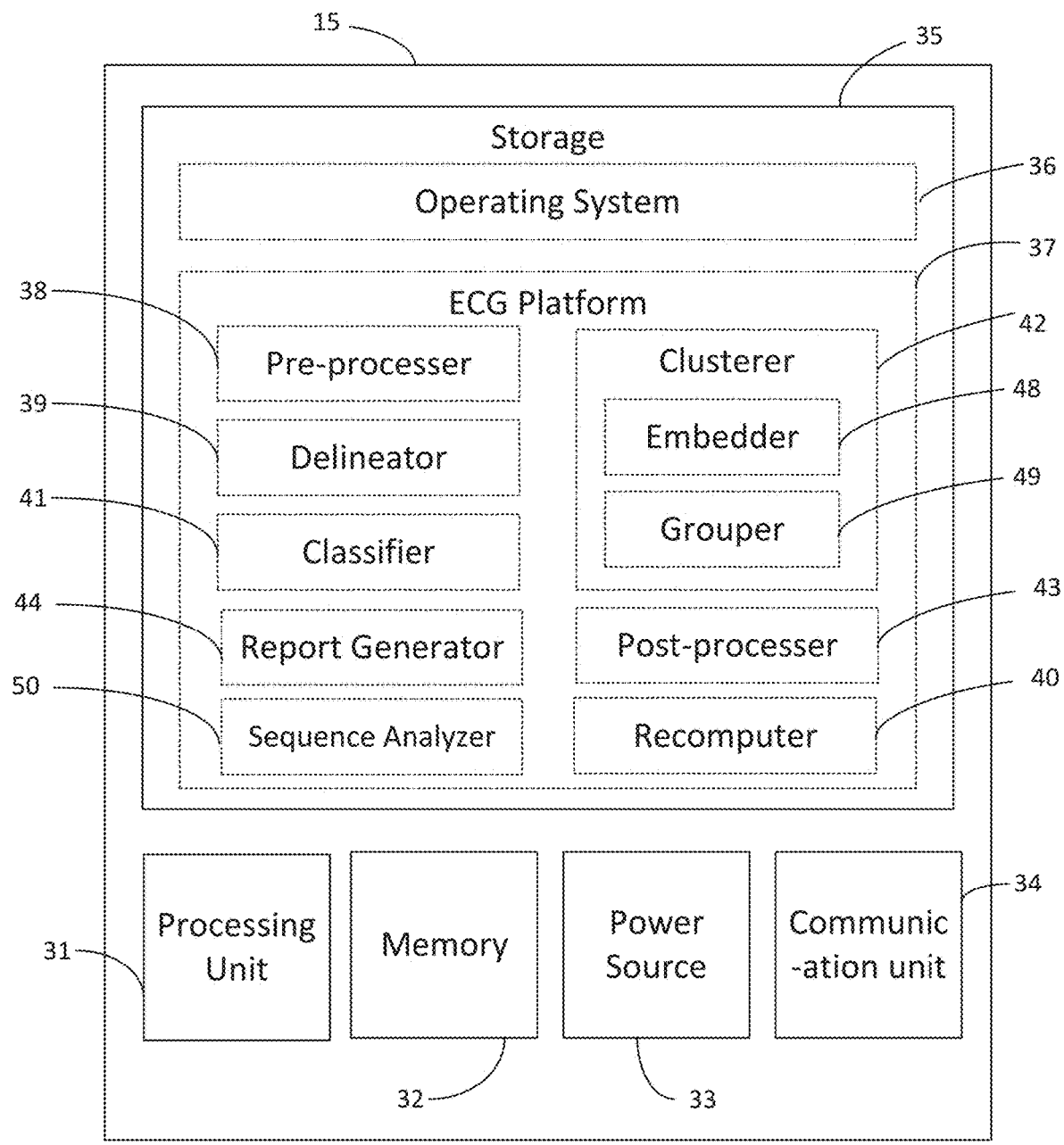

Referring now to FIGS. 3A-3B, exemplary functional blocks representing the hardware and software components of system device 14 and server 15 are shown. Referring now to FIG. 3A, hardware and software components of system device 14 may include one or more processing unit 21, memory 22, storage 27, communication unit 23, and power source 24, input devices 25 and output devices 26.

Processing unit 31 may be one or more processors configured to run collaboration operating system 28 and ECG application 29 and perform the tasks and operations of system device 14 set forth herein. Memory 22 may include, but is not limited to, volatile (e.g. random-access memory (RAM)), non-volatile (e.g. read-only memory (ROM)), flash memory, or any combination thereof. Communication unit 23 may receive and/or transmit information to and from other components in ECG processing system 10 including, but not limited to, sensing device 13 and server 15. Communication unit 23 may be any well-known communication infrastructure facilitating communication over any well-known wired or wireless connection, including over any well-known standard such as any IEEE 802 standard. Power source 24 may be a battery or may connect system device 14 to a wall outlet or any other external source of power. Storage 27 may include, but is not limited to, removable and/or non-removable storage such as, for example, magnetic disks, optical disks, or tape.

Input device 25 may be one or more devices coupled to or incorporated into system device 14 for inputting data to system device 14. Input device 25 may further include a keyboard, a mouse, a pen, a sound input device (e.g., microphone), a touch input device (e.g., touch pad or touch screen), a location sensor, and/or a camera, for example. Output device 26 may be any device coupled to or incorporated into system device 14 for outputting or otherwise displaying data and includes at least a display 17. Output device 26, may further include speakers and/or a printer, for example.

ECG application 29 may be stored in storage 27 and executed on processing unit 21. ECG application 29 may be a software application and/or software modules having one or more sets of instructions suitable for performing the operations of system device 14 set forth herein, including facilitating the exchange of information with sensing device 13 and server 15. For example, ECG application 29 may cause system device 14 to receive ECG data from sensing device 13, to record ECG data from sensing device 13, to communicate ECG data to server 15, to instruct server 15 to process and analyze ECG data, to receive processed and/or analyzed ECG data from server 15, to communicate user input regarding report generation to server, and to generate a graphic user interface suitable for displaying raw, analyzed and/or processed ECG data and data related thereto.

Operating system 28 may be stored in storage 27 and executed on processing unit 21. Operating system 28 may be suitable for controlling the general operation of system device 14 and may work in concert with ECG application 29 to achieve the functionality of system device 14 described herein. System device 14 may also optionally run a graphics library, other operating systems, and/or any other application programs. It of course is understood that system device 14 may include additional or fewer components than those illustrated in FIG. 3A and may include more than one of each type of component.

Referring now to FIG. 3B, hardware and software components of server 15 may include one or more processing unit 31, memory 32, storage 35, power source 33, and communication unit 34. Processing unit 31 may be one or more processors configured to run operating system 36 and ECG platform 37 and perform the tasks and operations of server 15 set forth herein. Given the volume of data and processing tasks assigned to processing unit 31, it is understood that processing unit 31 has superior processing power compared to processing unit 21.

Memory 32 may include, but is not limited to, volatile (e.g. random-access memory (RAM)), non-volatile (e.g. read-only memory (ROM)), flash memory, or any combination thereof. Storage 35 may include, but is not limited to, removable and/or non-removable storage such as, for example, magnetic disks, optical disks, or tape. Communication unit 34 may receive and/or transmit information to and from other components of ECG processing system 10 including, but not limited to, system device 14 and/or drive 16. Communication unit 34 may be any well-known communication infrastructure facilitating communication over any well-known wired or wireless connection. Power source 33 may be a battery or may connect server 15 to a wall outlet or other external source of power.

Operating system 36 and ECG platform 37 may be stored in storage 35 and executed on processing unit 31. Operating system 36 may be suitable for controlling general operation of server 15. ECG platform 37 may be a software application and/or software modules having one or more sets of instructions. ECG platform 37 may facilitate and oversee the processing and analysis of ECG data received from system device 14, report generation, and otherwise may be suitable for performing the operations of server 15 set forth herein.

ECG platform 37 may include several sub-modules and/or applications including, but not limited to, pre-processor 38, delineator 39, classifier 41, clusterer 42 which may include embedder 48 and grouper 49, post-processor 43, report generator 44, recomputer 40 and/or sequence analyzed 50. Each sub-module and/or application may be a separate software application and/or module having one or more sets of instructions. Pre-processor 38 may pre-process raw ECG data, delineator 39 may execute a first neural network to achieve delineation, classifier 41 may execute a second neural network to achieve classification, clusterer 42 may identify clusters in data processed by the first neural network, post-processor 43 may post-process data processed by the second neural network, embedder 48 may execute one or more algorithms and/or a third neural network to achieve embedding, grouper 49 may execute one or more algorithms and/or a fourth neural network to generate cluster groups, report generator 44 may generate reports based on raw ECG data and ECG data processed by ECG platform 37, and recomputer 40 may recompute and/or adjust embedder 48 and/or grouper 49 based on user input data. For example, recomputer 40 may recalculate episodes based on corrected wave information. Sequence analyzer 50 may be one or more algorithms and/or a third neural network which may be a recurrent neural network. Sequence analyzer 50 may analyze feature maps to determine one or more sequence labels and thereby achieve sequence identification as explained below. ECG platform 37 may also perform various other functions including, but not limited to, receiving requests from system device 14 to process and/or analyze ECG data, communicating processed and/or analyzed ECG data to system device 14, receiving a request to generate a report, requesting and/or receiving user interaction and/or instructions from system device 14, receiving user input data and/or instruction information from system device 14 regarding report generation, and/or communicating a report to system device 14.

Server 15 may also optionally run a graphics library, other operating systems, and/or any other application programs. It of course is understood that server 15 may include additional or fewer components than those illustrated in FIG. 3B and may include more than one of each type of component.

Figure 4:
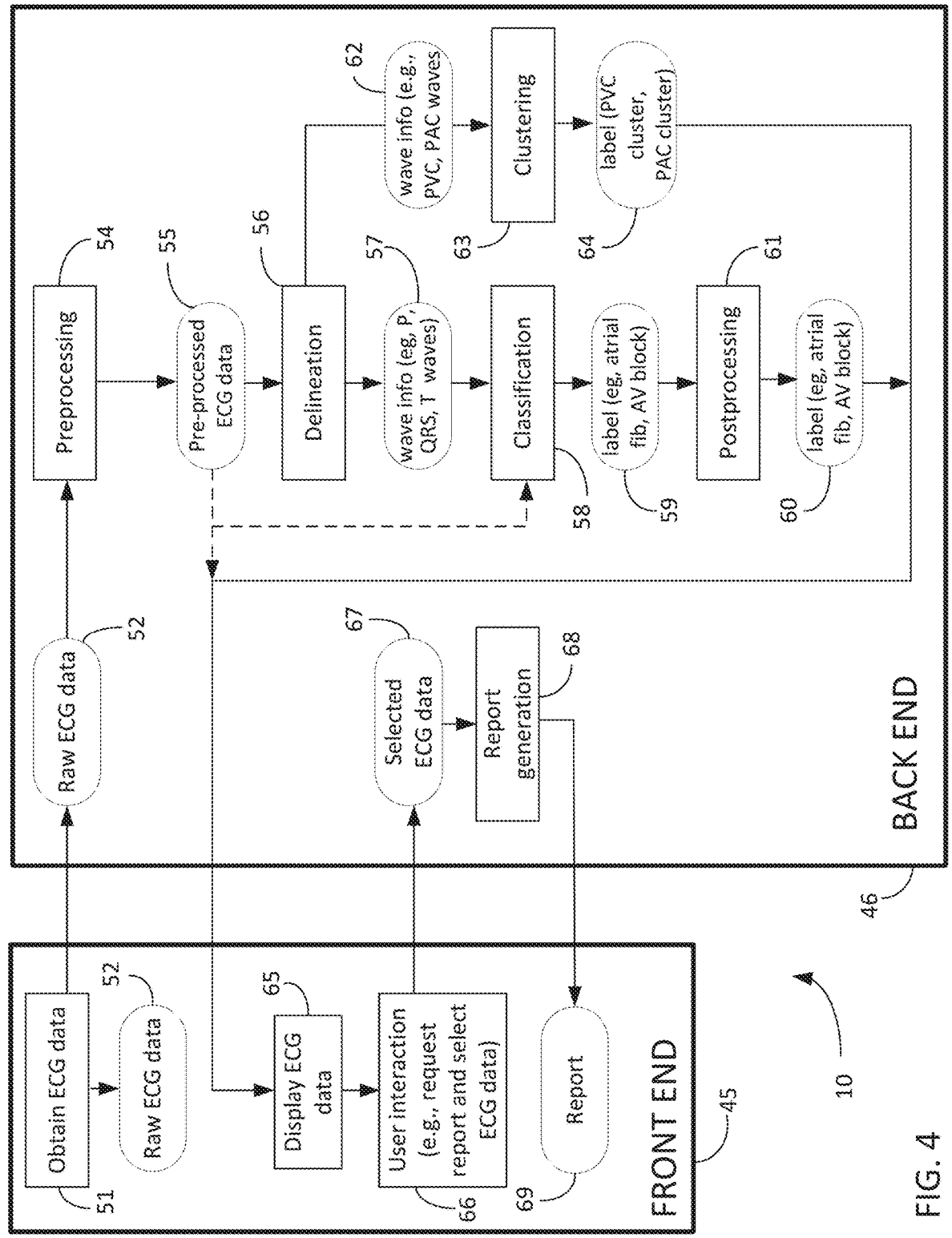
FIG. 4 is a flow chart of an exemplary method of processing ECG data using, displaying ECG data, and generating a report including ECG data.

FIG. 4 illustrates an exemplary process for implementing ECG processing system 10 to receive and record ECG data, process and analyze ECG data, and generate reports involving ECG data, and further shows the flow of information between front end 45 and back end 46 of ECG processing system 10, as described, for example, in U.S. Pat. Nos. 10,959,660, 10,779,744, and 10,426,364, the entire contents of each of which are incorporated herein by reference. Front end 45 includes at least ECG application 29 running on system device 14. Back end 46 includes at least ECG platform 37 running on server 15.

As is shown in FIG. 4, at step 51, ECG application 29 may cause system device 14 to receive and/or otherwise obtain raw ECG data 52 from sensing device 13. For example, ECG application 29 may cause sensing device 13 to sense the cardiac signal and communicate the cardiac signal sensed by sensing device 13 to system device 14. Raw ECG data is the cardiac signal sensed by sensing device 13. Raw ECG data 52 has not been processed or analyzed by ECG processing system 10. Raw ECG data 52 preferably involves data sampled multiple times per heartbeat over a plurality of heartbeats. It is understood that sensing device 13 may convert an analog cardiac signal into a digital signal, a different component not shown in FIG. 2 may convert the analog cardiac signal to a digital signal, or ECG application 29 may cause system device 14 to convert the analog cardiac signal to a digital signal. Raw ECG data in both analog and digital form are referred to herein as raw ECG data 52.

Upon receiving raw ECG data 52, ECG application 29 may cause system device 14 to record raw ECG data 52 and may optionally save some or all of raw ECG data 52 to system device 14. As explained above, the signals may correspond to one or more leads. When multiple leads are used, all leads may be processed simultaneously. It is understood that the cardiac signal generated by each lead may have varying lengths. It is further understood that the cardiac signal may be short term (e.g., 10 seconds in standard ECGs) or long term (several days in holters). System device 14 may optionally display raw ECG data 52 or a portion thereof on display 17.

As is shown in FIG. 4, raw ECG data 52 may be transmitted from front end 45 to back end 46. Specifically, ECG application 29 may cause system device 14 to communicate raw ECG data 52 to ECG platform 37 running on server 15. Upon receiving raw ECG data 52, ECG platform 37 may cause server 15 to save some or all of raw ECG data 52 to server 15. Further, after receiving raw ECG data 52, ECG platform 37 cause raw ECG data 52 to be preprocessed at step 54 by pre-processor 38. It is understood that pre-processor 38 may be a stand-alone component of ECG platform 37 or subcomponent of delineator 39.

Pre-processor 38 may process raw ECG data 52 or a portion thereof by removing the disturbing elements of the cardiac signal, such as noise from the raw ECG data. For noise filtering, a multivariate functional data analysis approach may be used (Pigoli and Sangalli. Computational Statistics and Data Analysis, Vol. 56, 2012, pp 1482-1498). As the signal sensed by sensing device 13 may vary due to a patient's movements, the baseline frequency of raw ECG data 52 may be removed by pre-processor 38 and the cardiac signal may be expressed at a chosen frequency. The frequencies of the signal corresponding to the patient's movements may be removed using median filtering (Kaur et al., Proceedings published by International Journal of Computer Applications, 2011, pp 30-36). Applying raw ECG data 52 to pre-processor 38 generates pre-processed ECG data 55. At this point, ECG platform 37 may cause pre-processed ECG data 55 to optionally be communicated to ECG application 29 running on system device 14 for display on display 17. ECG platform 37 may alternatively, or additionally, cause pre-processed ECG data 55 to be used as an input at classification step 58, discussed in more detail.

At step 56, ECG platform 37 causes pre-processed ECG data 55 to be applied to delineator 39 for delineation. Delineator 39 applies a first neural network that is a delineation neural network to pre-processed ECG data 55. A neural network refers to a mathematical structure or algorithm that may take an object (e.g., matrix or vector) as input and produce another object as an output though a set of linear and non-linear operations called layers. For example, the input of the first neural network may be one or more multi-lead cardiac signals that are pre-processed to remove noise and/or baseline wandering.

To apply pre-processed ECG data 55 to the first neural network, delineator 39 may cause some or all of raw ECG data 52 to be expressed as matrix X, which may be a matrix of real numbers. For example, matrix X may be a matrix of size m×n at the frequency used for training the networks, described in more detail below. The constant "m" may be a number of leads in sensing device 13, which is typically 12, though any number of leads may be used. In this example, the number of samples "n" provides the duration of the cardiac signal "n/f" with f being the sampling frequency of the cardiac signal. The sample rate is above a predetermined rate and is preferably relatively high, such as, for example, at least 20, at least 250, at least 500 or at least 1000 samples per second, etc. In one embodiment, all of the sampled ECG data is transferred to the server for input into the processing algorithms without filtering out ECG data. While the ECG data applied to the first neural network is preferably pre-processed ECG data 55, it is understood that a non-preprocessed cardiac signal (i.e., raw ECG data 52, or a portion thereof) may be applied to the first neural network.

The first neural network may provide as an output, values corresponding to the likelihood of the presence of or one or more waves at a plurality of time points in the cardiac signal. The time points may be dictated by the raw ECG data, may be selected by the user of system device 14, or may be preprogrammed. The first neural network may be a convolutional neural network, and is preferably a fully convolutional neural network. Convolutional neural networks are a particular type of neural network where one or more matrices, which are learned, do not encode a full linear combination of the input elements, but the same local linear combination at all the elements of a structured signal, such as a cardiac signal, through a convolution (Fukushima, Biol. Cybernetics, Vol. 36, 1980, pp 193-202, LeCun et al., Neural Computation, Vol. 1, 1989, pp 541-551). A network which only contains convolutional networks is called a fully convolutional neural network.

Accordingly, at step 56, delineator 39 causes the first neural network to read each time point of the cardiac signal, spatio-temporally analyze each time point of the cardiac signal, and assign a score at each time point corresponding to one or more types of waves. In this manner, all types of waves in the cardiac signals may analyzed and the likelihood of their presence at each time point, quantified, in a single step. Accordingly, each score generated by delineator 39 is indicative of the likelihood of the presence of a particular wave type at a given time point of the cardiac signal. The wave types may be any well know wave type such as, P-waves, Q-wave, R-wave, S-wave, Q-waves, R-waves, S-waves, QRS complexes, and/or T-waves, for example. In this manner, delineator 39 may process data sampled multiple times per heart beat across a plurality of heart beats.

The output of the first neural network may be a matrix Y, which may be a matrix of real numbers. For example, matrix Y may be a matrix of the size p×n. Matrix Y may include scores for each type of wave at each time point of the cardiac signal. In matrix Y, "n" is the number of samples, as discussed above with respect to Matrix X, and "p" is the number of wave types plus the number of wave characterizations. As explained in more detail below, wave characterization may correspond to conductivity, prematurity, ectopy, and/or origin of the waves in the cardiac signal, for example. In one example, the wave types include (1) P-waves, (2) QRS complexes, and (3) T-waves, and the wave characterizations include (1) premature waves, (2) paced waves, (3) ventricular QRS complexes, (4) junctional QRS complexes, (5) ectopic P waves, and (6) non-conducted P waves. Accordingly, in this example, p=3+6=9. Each wave type may be expressed according to certain characteristics of that wave, such as start and end points (i.e., onset and offset)).

Figure 5A:
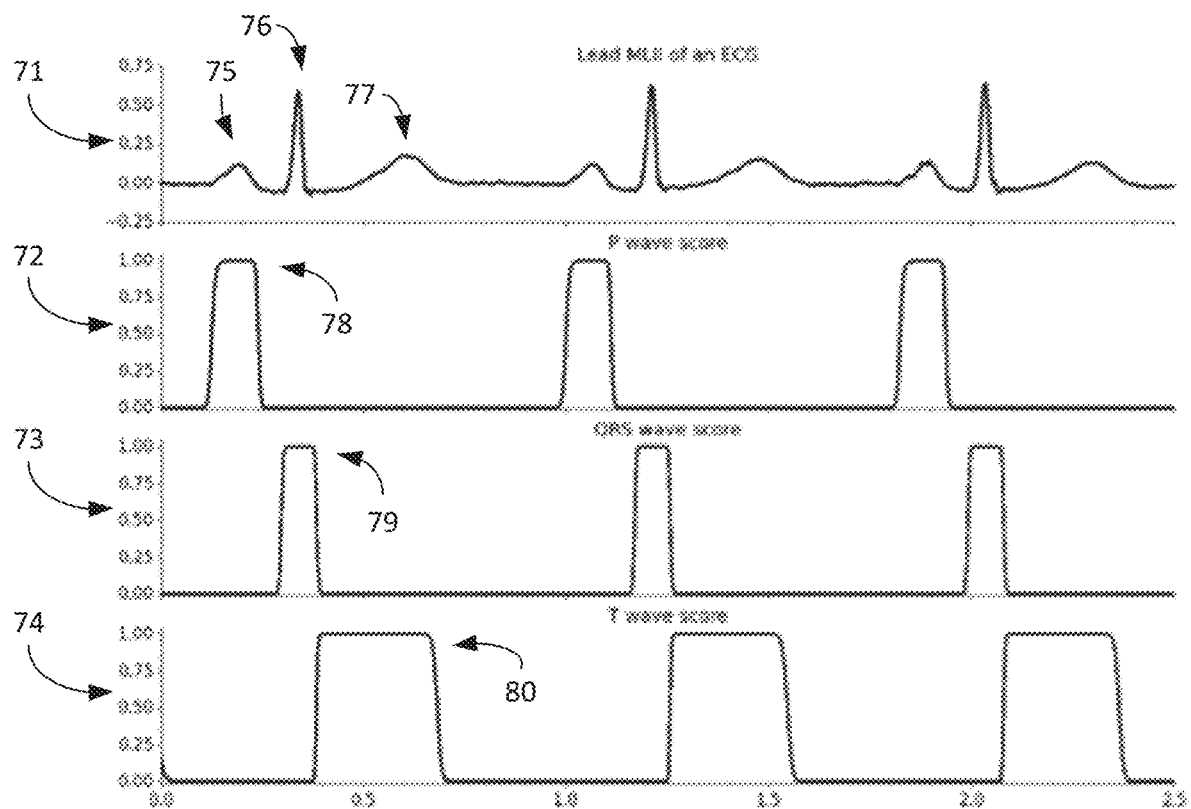
FIGS. 5A-5B are line graphs representing an exemplary ECG signal and an exemplary output of a first neural network for each wave type analyzed, respectively.
Figure 5B:
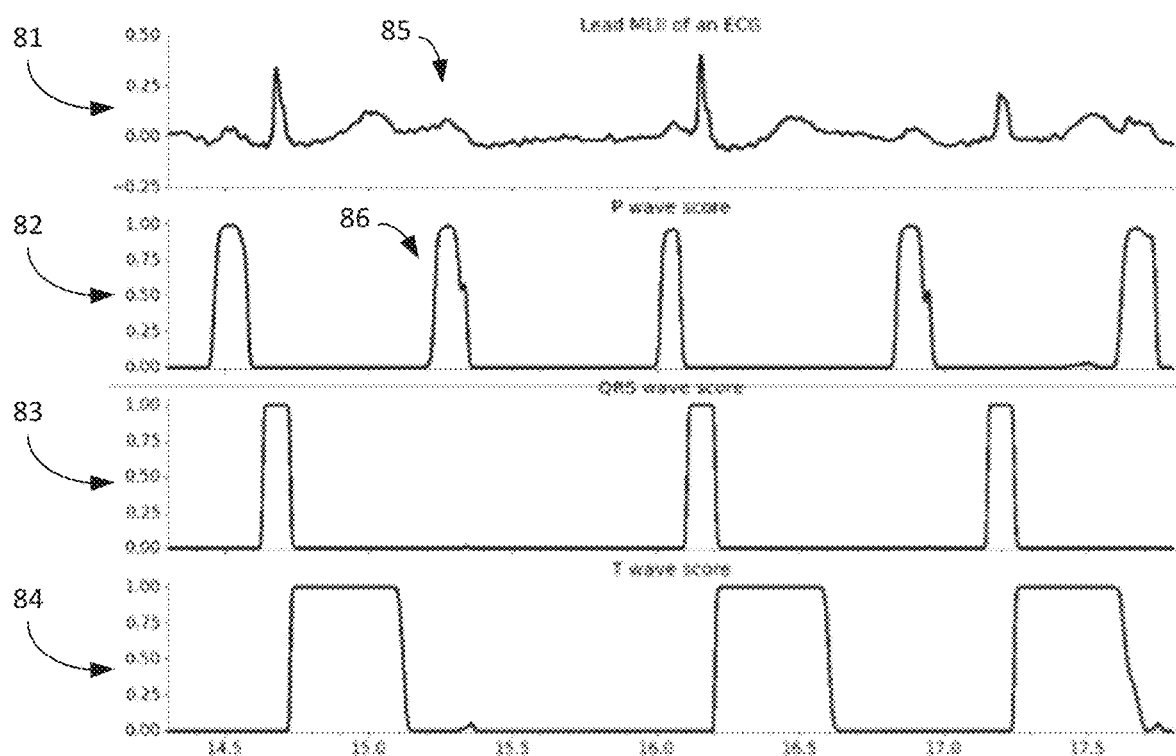

Referring now to FIGS. 5A and 5B, exemplary outputs of the first neural network are graphed for each wave type to illustrate the value of generating scores at each time point corresponding to a plurality of types of waves. Specifically, FIG. 5A illustrates an exemplary output where the delineation neural network processed a normal cardiac signal (with no abnormalities) and FIG. 5B illustrates an exemplary output where the delineation neural network processed a cardiac signal having "hidden" P-waves, for example due to an atrioventricular block.

Referring now to FIG. 5A, four line graphs are illustrated, each graph showing time on the x-axis. Line graph 71 represents the cardiac signal over multiple beats. The plotted signal reflects the well-known ECG waveform having a P-Wave (point 75), QRS complex (point 76), and T-wave (point 77). Line graph 72 is a graph the P-wave score over the same time points in the cardiac signal. Similarly, line graph 73 and line graph 74 are graphs of the QRS score and T-wave scores, respectively, over the same time points. The y-axis for each line graphs 72-74 is the score assigned at each time point, ranging from 0 to 1, with 0 indicating a low likelihood of the presence of a particular wave and 1 indicating a high likelihood of the presence of a particular wave. For example, line graph 72 indicates a very high likelihood of the presence of P-waves at score 78 which corresponds to the time points near point 75, line graph 73 indicates a very high likelihood of the presence of a QRS complex at score 79 which corresponds to the time points near point 76, and line graph 74 indicates a very high likelihood of the presence of a T-wave at score 80 which corresponds to the time points near point 77.

FIG. 5B, like FIG. 5A, illustrates four line graphs, line graphs 81-82, which are similar to line graphs 71-74. Specifically, line graph 81 represents the cardiac signal over several beats, line graph 82 represents the P-wave score over the cardiac signal, line graph 83 represents the QRS score over the cardiac signal, and line graph 84 illustrates the T-wave score over the cardiac signal. Unlike FIG. 5A, the ECG signal in line graph 81 includes hidden P-waves such as the hidden P-wave shown at point 85. Hidden P-waves are P-waves that occur during another wave or complex such as a T-wave. As the cardiac signal processed by the delineation network involves a high sample rate and the delineation network generates data for each wave type at each time point, the output recovered is robust enough (i.e., includes enough sample points) to identify two waves occurring at the same time, such as the case with hidden P-waves. For example, line graph 82 indicates a very high likelihood of the presence of P-waves at score 86 which corresponds to the time points near point 85. Accordingly, it is understood that the delineation neural network is not limited to recovering only one wave at each time point and therefore can identify several waves at any time point. It is further understood that signals from one or more leads may be processed simultaneously by the first neural network.

Using the scores assigned to each time point corresponding to each wave type (e.g., P-wave, QRS complex, T-wave, etc.), delineator 39 may post-process the cardiac signal. Post-processing involves, assigning to each time point, none, one, or several waves, calculating the onset and offset of each of the identified waves, and optionally determining the characterization of the waves. Waves may be assigned to each time point by determining that a wave exists at that time point if a certain value is achieved. Computing the "onset" and "offset" of each wave involves computing the time points of the beginning and the end of each wave in the cardiac signal, the beginning referred to as the "onset" and the end referred to as the "offset." This may involve analyzing the time points corresponding begging and end of the highest values for each wave type. Delineator 39 may characterize the waves by identifying prematurity, conductivity and ectopy. Wave characterization leverages the contextual information between each wave and/or each beat. For example, the premature label may be applied to the wave if a certain threshold value is achieved at a certain time point or an average value over several time points.

After computing the onset and offset of each wave type in the cardiac signal, delineator 39 may calculate global measurements. Global measurements are derived from the onset and offset of each wave type and may relate to features and characteristics of the cardiac signal such as intervals between waves and wave durations. For example, global measurements may include, but are not limited to, PR interval, P-wave duration, QRS complex duration, QRS axis, QT interval, corrected QT interval (Qtc), T-wave duration, JT interval, corrected JT interval, heart rate, ST elevation, Sokolov index, number of premature ventricular complexes, number of premature atrial complexes (PAC), ratio of non-conducted P waves, and/or ratio of paced waves.

Delineator 39 may further deduce labels solely from the information generated by delineator 39. For example, the following labels may be deduced by delineator 39: short PR interval (i.e., PR interval <120 ms), first degree AV block (e.g., PR interval >200 ms), axis deviations, long QTc, short QTc, wide complex tachycardia, and/or intraventricular conduction blocks. Labels determined solely from information generated by delineator 39 are referred to as delineation based labels.

Referring again to FIG. 4, ECG platform 37 may cause the output of step 56 (e.g., wave information 62) as well as pre-processed ECG data 55 to be communicated or otherwise applied to clusterer 42 for clustering at step 63. Wave information 62 may include scores regarding PVC waves and PAC waves including onsets and offsets generated and relevant durations. Clusterer 42 may process wave information 62 and identify clusters of PAC or PAV waves during the duration of the cardiac signal. Once identified, clusterer 42 may assign cluster label 64 to one or more time windows, identifying either a PVC or a PAC cluster for each time window. A time window is defined by two time points in the cardiac signal.

Referring again to FIG. 4, ECG platform 37 may also cause the output of step 56 (e.g., wave information 57) as well as pre-processed ECG data 55 to be communicated or otherwise applied to classifier 41 for classification at step 58. Classification at step 58 involves applying a second neural network (i.e., classification neural network) to pre-processed ECG data 55. Accordingly, in one example, the input of the second neural network may be one or more multi-lead cardiac signals with variable length that is pre-processed. Classifier 41 may also process wave information 57 and/or other information such as patient-specific information including the patient's age or any relevant clinical information. As explained above, ECG platform 37 may cause optionally cause pre-processed ECG data 55 to be communicated directly to classifier 41 and processed by classifier 41 if delineation at step 56 is not necessary. In this manner, classifier 41 may process data sampled multiple times per heart beat across a plurality of heart beats.

The second neural network generates an output having values that correspond to the likelihood of the presence of one or more abnormality, condition and/or descriptor at each time point of the cardiac signal. If a time point or time window is determined to correspond to a certain abnormality, condition, and/or descriptor, a label corresponding to that abnormality, condition, and/or descriptor will be assigned to that time point or window. In one example, one or more labels 59 may be assigned to a time point or time window if a score achieves a predetermined threshold. Accordingly, multi-label localization may be achieved for abnormalities, conditions, and/or descriptors by generating a plurality of values at each time point and assigning one or more labels at each time point.

Classifier 41 may recover the output of the classification neural network as a vector of size q. The values in the vector correspond to the presence of each label at each time point or each time window. For example, the output of the classification neural network may be the vector [0.98: 0.89; 0.00] with the corresponding labels for each element of the vector: Right Bundle Branch Bloc; Atrial Fibrillation; Normal ECG. The scores may be between 0 and 1. For the vector above, a threshold of 0.5 would result in the labels "Right Bundle Branch Block" and "Atrial Fibrillation" being assigned by classifier 41 to the time point or time window corresponding to the score. It is understood that the threshold may be preprogrammed and/or selected by the user and may be modified to provide varying degrees of sensitivity and specificity. By assigning one or more labels for each time point, onsets and offsets corresponding to each label may be computed to identify durations of episodes (e.g., abnormalities episodes).

Abnormalities and conditions may include any physiological abnormality or condition which may be identifiable on the cardiac signal. Today about 150 measurable abnormalities may be identified on cardiac signal recordings. Abnormalities and conditions may include but are not limited to, sinoatrial block, paralysis or arrest, atrial fibrillation, atrial flutter, atrial tachycardia, junctional tachycardia, supraventricular tachycardia, sinus tachycardia, ventricular tachycardia, pacemaker, premature ventricular complex, premature atrial complex, first degree atrio-ventricular block (AVB), 2nd degree AVB Mobitz I, 2nd degree AVB Mobitz II, 3rd degree AVB, Wolff-Parkinson-White syndrome, left bundle branch block, right bundle branch block, intraventricular conduction delay, left ventricular hypertrophy, right ventricular hypertrophy, acute myocardial infarction, old myocardial infarction, ischemia, hyperkalemia, hypokalemia, brugada, and/or long QTc. Descriptors may include descriptive qualities of the cardiac signal such as "normal" or "noisy ECG."

Upon applying the second neural network at step 58, classifier 41 may read each time point of the cardiac signal as well as each global measurement, analyze each time point of the cardiac signal and each global measurement, compute time windows by aggregating at least two time points, and compute scores for each time window, the scores corresponding to a plurality of non-exclusive labels.

Figure 6A:
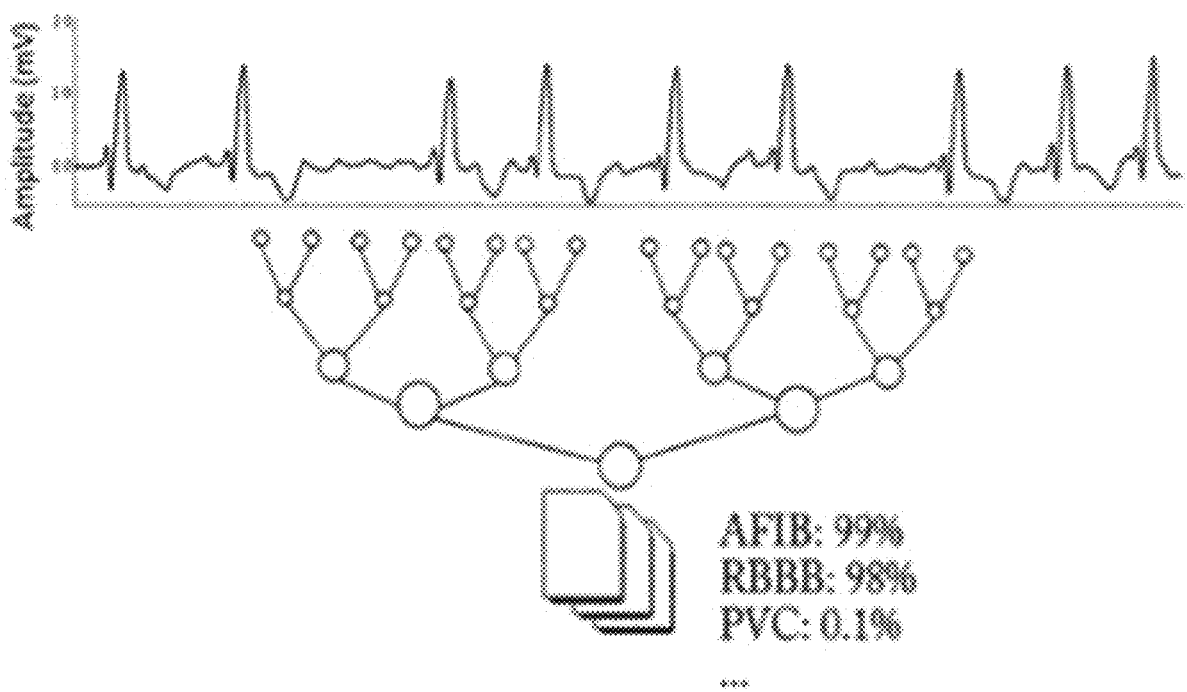
FIGS. 6A-6B are exemplary representations of classification neural networks in the form of a convolutional neural network and a recurrent neural network, respectively.

The classification neural network may be a convolutional neural network or a recurrent neural network. Referring now to FIG. 6A, a classification neural network in the form of a convolutional neural network is illustrated applied to an ECG signal. Most convolutional neural networks implement a few convolutional layers and then standard layers so as to provide a classification. The ECG signal is given as input to the network, which aggregates the information locally and then combines it layer by layer to produce a high-level multi-label classification of the ECG. For each label a score is provided. The labels of the convolutional neutral network shown in FIG. 6 include atrial fibrillation (AFIB), right bundle branch block (RBBB) and, and premature ventricular complex (PVC).

Figure 6B:
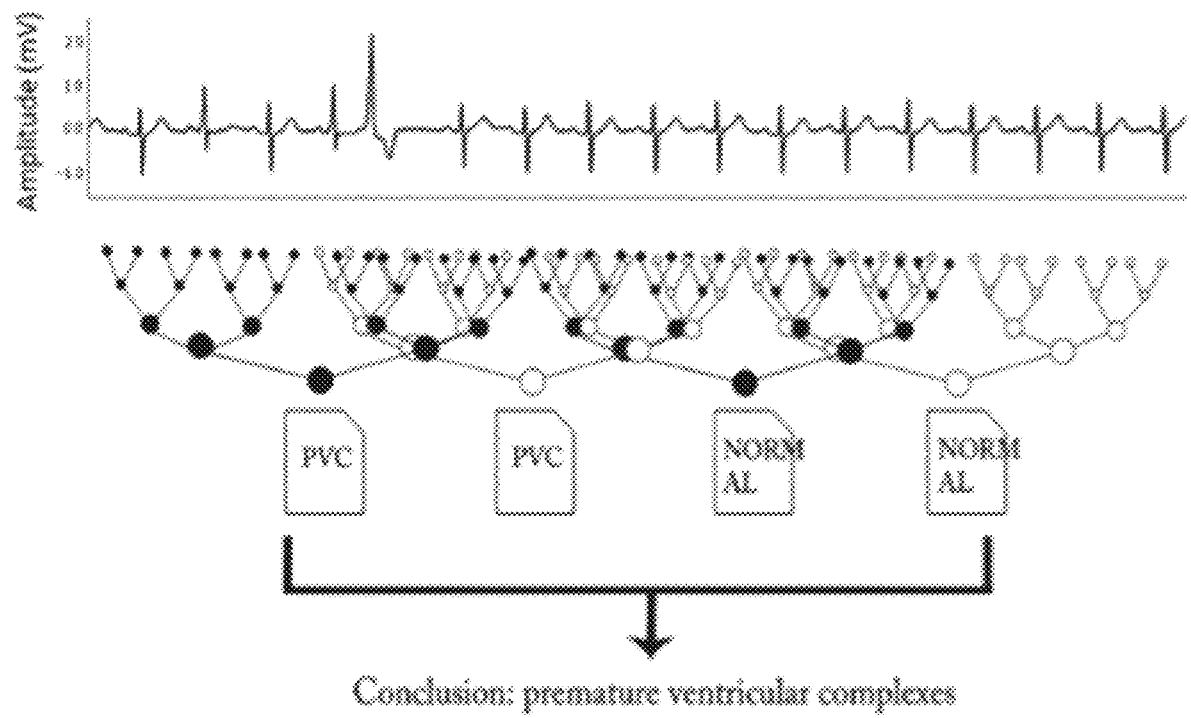

Referring now to FIG. 6B, a classification neural network in the form of a recurrent convolutional neural network is illustrated. Similar to FIG. 6A, the ECG signal is given as input to the network. A recurrent convolutional neural network refers to a particular convolutional neural network structure able to keep memory of the previous objects it has been applied to. A recurrent convolutional neural network is composed of two sub-networks: a convolutional neural network which extracts features and is computed at all time points of the cardiac signal, and a neural network on top of it which accumulates through time the outputs of the convolutional neural network in order to provide a refined output. In this manner, the convolutional neural network acts as a pattern detector whose output will be accumulated in time by the recurrent neural network.

As is shown in FIG. 6B, the output of the convolutional neural network identified four labels at various time points including premature ventricular complex (PVC) and Normal. Those labels were then applied to the second neural network which produced the refined output "premature ventricular complex." In this example, the network correctly recognized a premature ventricular complex (PVC, the fifth and largest beat) in the first part of the signal while the second part of the signal is considered normal. As the cardiac signal includes abnormality, it cannot therefore be considered as normal, and the accumulated output is therefore PVC.

The first neural network (i.e., delineation neural network) and the second neural network (i.e., classification neural network) must be trained to achieve the behavior and functionality described herein. In both the delineation and the classification embodiments, the networks may be expressed using open software such as, for example, Tensorflow, Theano, Caffe or Torch. These tools provide functions for computing the output(s) of the networks and for updating their parameters through gradient descent.

Training the neural networks involves applying numerous datasets containing cardiac signals and known outputs to the neural networks. A database of the datasets containing cardiac signals collected across a plurality of patients using the systems and methods described herein may be stored on server 15 and/or drive 16 (e.g., in the cloud). The datasets in the database may be used by server 15 to analyze new cardiac signals inputted into the system for processing. In a preferred embodiment, any cardiac signal applied to the trained neural network will have the same sampling rate and/or frequency as the cardiac signals in the datasets used to train the neural network. For example, training of the classification neural network begins with a dataset containing cardiac signals and their known delineation. As explained above, the cardiac signal is expressed as a matrix of size m×n at a predefined frequency. For example, the network may be trained at 250 Hz, 500 Hz or 1000 Hz, though any frequency could be used. The delineation is then expressed in the form of a Matrix Y of size p×n where p is the number of types of waves. Each wave is expressed with their start and end points such as, for example: (P, 1.2 s, 1.3 s), (QRS 1.4 s 1.7 s), (T, 1.7 s, 2.1 s), (P, 2.2 s, 2.3 s). In this example, the first row of Matrix Y corresponds to P-waves, and will have a value of 1 at times 1.2 s and 1.3 s, and as well as 2.2 s and 2.4 s, and 0 otherwise. The second row of Matrix Y corresponds to QRS complexes and will have a value of 1 at times 1.4 s and 1.7 s, and otherwise 0. Finally, the third row of Matrix Y corresponds to T-waves and will have a value of 1 at times 2.2 s and 2.3 s, and otherwise 0. The parameters of the network may then be modified so as to decrease a cost function comparing the known delineation and the output of the network. A cross-entropy error function is used so as to allow for multi-labeling (i.e., allowing for multiple waves at a given instant). This minimization can be done though a gradient step, repeating the foregoing steps at least once for each cardiac signal of the dataset. It is understood that a similar approach may be used to train the delineation neural network (i.e., second neural network).

Figure 7:
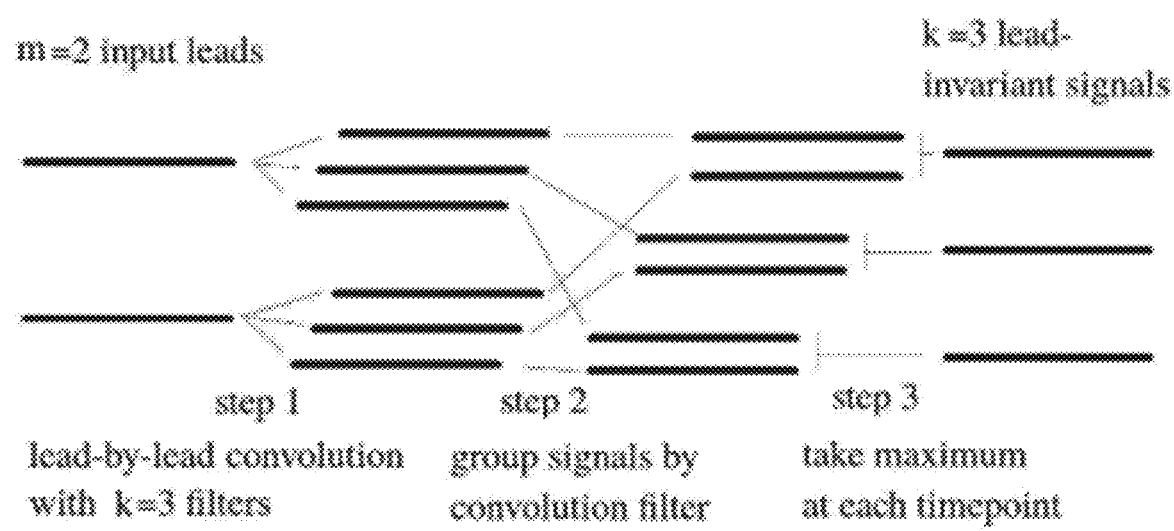
FIG. 7 is an exemplary representation of a variable number of lead entries and a constant number of outputs.

It is further understood that ECG platform 37 may cause neural networks described herein to process cardiac signals having a differing number of leads in entry. For example, the neural network may include a sequence of layers at the beginning of the network so as to obtain a network which is independent of the number of input leads and can therefore process cardiac signals with any number of leads m. For example, FIG. 7 illustrates two input leads (m=2) and three output signals (k=3). However, the same structure can process any number of input leads m and will still provide the same number of output signals, which can be fed to the rest of the network for which a fixed number of input signals is required. For this reason, the number of input leads may vary and need not be fixed.

As is shown in FIG. 7, to obtain k signals from an m input leads, the leads may be convoluted using a lead-by-lead convolution with k filters. The signal may then be grouped by a convolution filter in order to obtain k groups of m leads and a mathematical function is finally applied to each group to obtain k leads. The mathematical function may be the maximum at each time point or may be any other function known to one skilled in the art.

Referring again to FIG. 4, at step 61, ECG platform 37 may cause labels for each time window (i.e., labels) to be aggregated by post-processor 43 to generate processed labels 60. The labels may be derived from global measurements based on delineation. For example, the label corresponding to first degree atrioventricular block may be derived from a PR interval longer than 200 ms. As explained above, the PR interval is a global measurement based on the delineation. Post-processor 43 may also aggregate the delineation-based labels with the classification labels corresponding to the same time points.

Post-processor 43 may also filter the labels to remove redundant labels, assemble labels according to a known hierarchy of labels, or ignore labels that are known to be of lesser importance according to a hierarchy or weighted values. Post-processor 43 may also aggregate the labels through time so as to compute the start (onset) and end (offset) times of each abnormality. It is understood that post-processor 43 may be a standalone component or may be a subcomponent of classifier 41.

As is shown in FIG. 4, the information generated on back end 46 by ECG platform 37 in steps 54, 56, 58 and 61, and optionally, 63, may be communicated by ECG platform 37 to ECG application 29 on front end 45. ECG application 29 may cause the foregoing information to be displayed, at step 65, on display 17 of system device 14. The information generated on back end 46 may be automatically transmitted by ECG platform 37 or ECG platform 37 may cause the information to be stored on server 15 until requested by ECG application 29. Upon generating the data, ECG platform 37 may transmit a message to ECG application 29, informing ECG application 29 that the data is available from ECG platform 37.

ECG application 29 may receive data (e.g., raw ECG data, pre-processed ECG data, wave information, labels and any other data generated during steps 54, 56, 58, 61, and/or 63) and cause system device 14 to display as described in U.S. Patent Pub. No. 2020/0022604, the entire contents of which are incorporated herein by reference. Specifically, the '604 publication explains that the ECG signal, features of the ECG signal, and/or descriptors of the ECG signal may be displayed in a multiple field display in an interactive manner.

Figure 8:
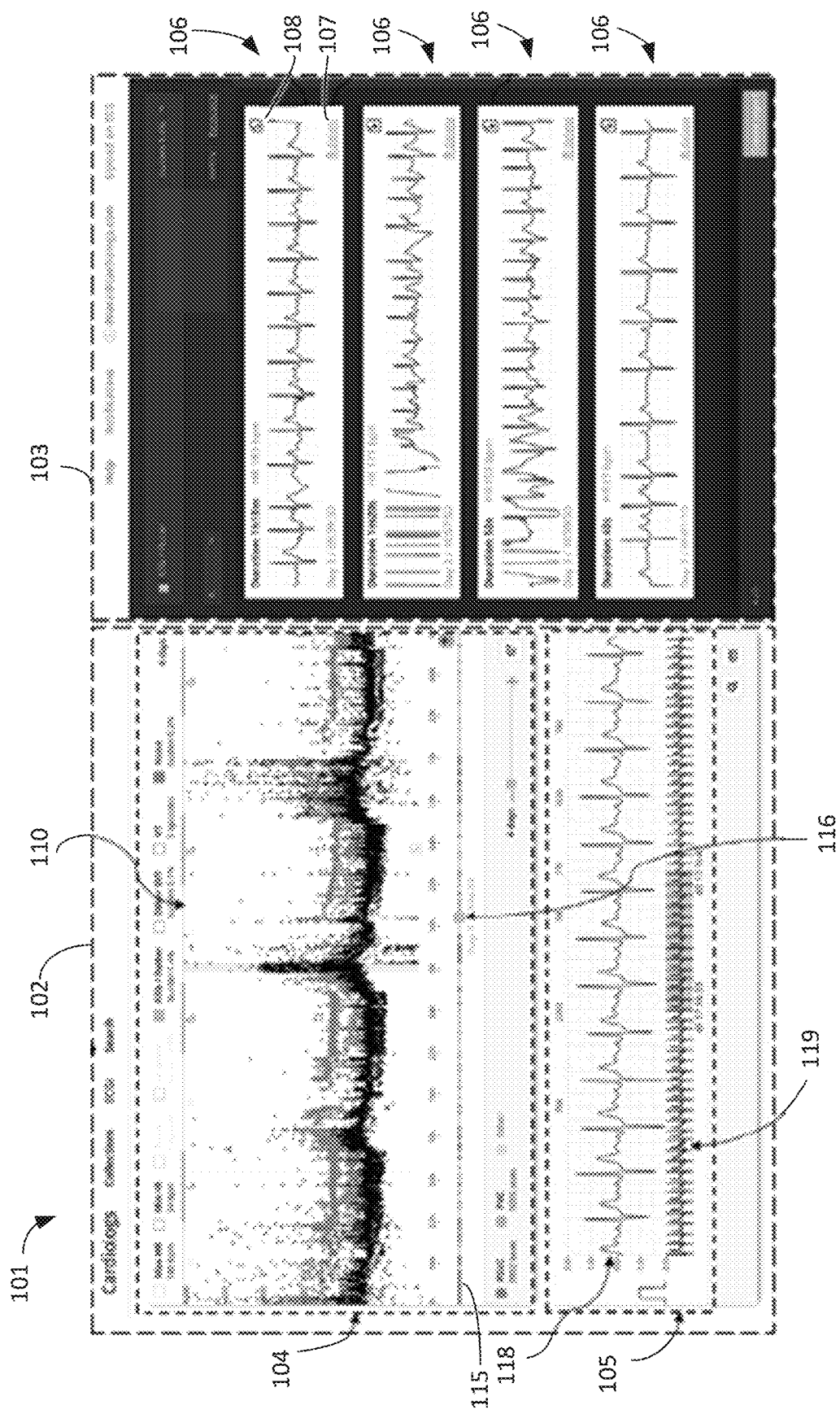
FIG. 8 is an exemplary user interface having an R-R plot generated in accordance with aspects of the recent disclosure.

Referring now to FIG. 8, an exemplary display, interactive display 101, is illustrated. Interactive display 101 includes first side 102 and second side 103. First side 102 further includes second graphic window 105 and first graphic window 104, having plot 110 which includes data corresponding to the ECG signal. First graphic window 104 includes plot 110 providing a global view of an ECG signal.

Figure 9:
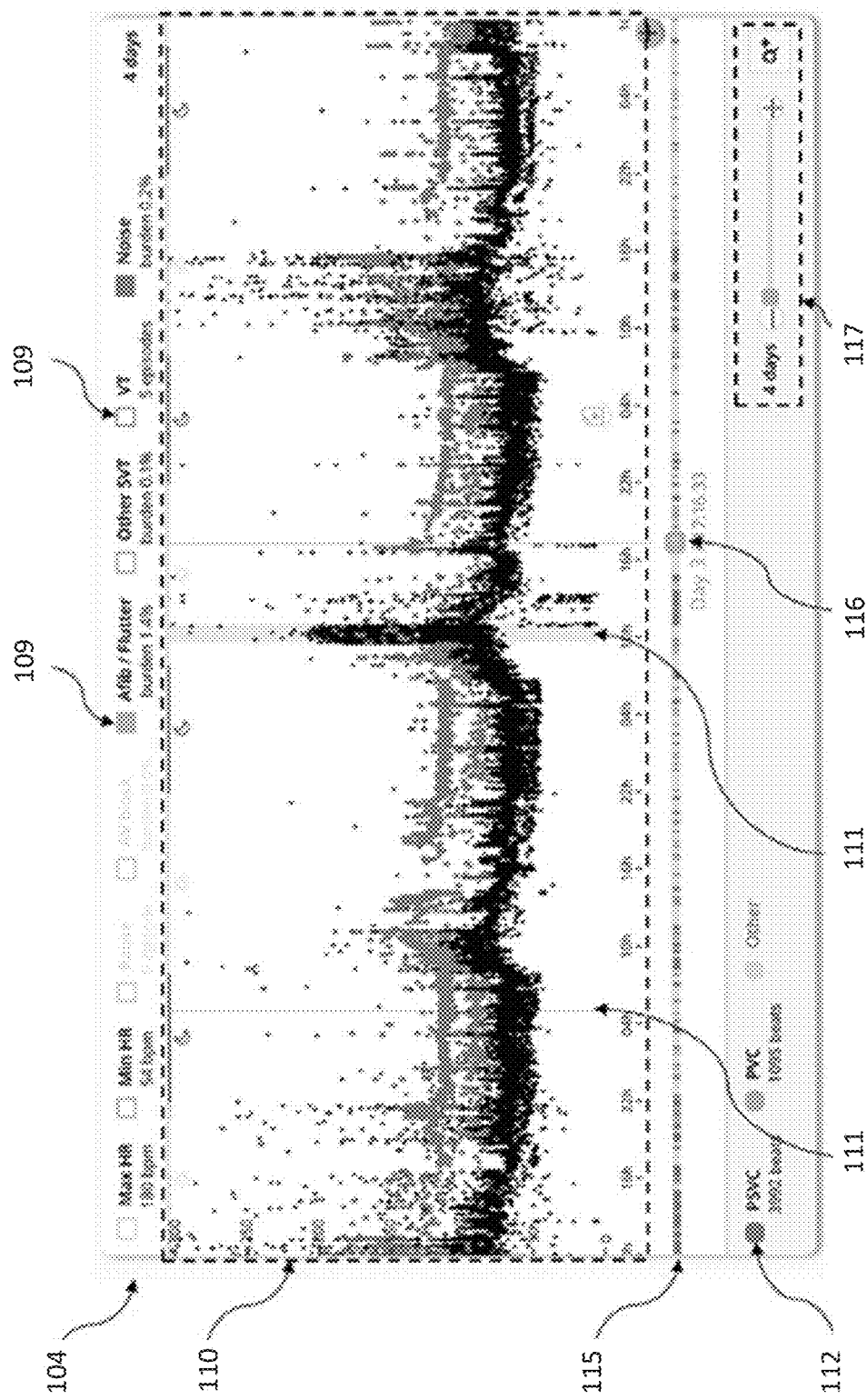
FIG. 9 is a zoomed-in view of the R-R plot shown in FIG. 8.

Referring now to FIG. 9, a zoomed-in version of first graphic window 104 is illustrated. In this exemplary display, plot 110 is an R-R interval plot which is a plot of R-R intervals (interval between two QRS waves) through time. As shown in FIG. 9, the upper region of first graphic window 104 comprises multiple label buttons 109. Each label button 109 has, displayed in its proximity, text describing the label to which it is associated. Each label button 109 is associated with a color so that, when label button 109 is selected by the user, graphic portion 111 is displayed on the plot 110 to visually indicate the presence the episodes and/or events corresponding to the label associate with label button 109. This provides visual references for the user permitting easy identification of a specific category of events and/or episodes along the cardiac signal. In the exemplary display illustrated in FIG. 9, secondary labels 112 are included. In this exemplary display, secondary labels 112 include beat label PVC (premature ventricular complex) and PSVC (premature supraventricular complex), though it is understood that other secondary labels may be included. The points in the plot 110 associated with the label PVC and PSVC are colored, as shown in FIG. 9 by the presence of points of color different from black.

First graphic window 104 further comprises, parallel to the time axis of the plot 110, temporal bar 115. Temporal bar 115 provides a linear representation of the total ECG acquisition time wherein the time periods associated to episodes or events are represented as colored segments. As is shown in FIG. 9, the darker grey zones on temporal bar 115 correspond to time periods of noisy signal (e.g., when the signal is too artifacted and the analysis algorithm cannot propose a delineation and proper detection). First graphic window 104 further comprises interactive cursor 116. A user using ECG application 29 may move interactive cursor 116 along temporal bar 115 to allow a navigation of the plot 110 along the total ECG acquisition time. In the right bottom corner of first graphic window 104, first graphic window 104 comprises second interactive means 117 configured to cause plot 110 to zoom in and out.

Referring again to FIG. 8, second side 103 includes multiple episode plots 106. Each episode plot 106 displays at least one segment of the ECG strip corresponding to a detected episode and may include text regarding the duration (e.g., "Duration: 1 h 38 m") and/or the starting time of the episode (e.g., "Day 3/09:39:30"). Each episode plot 106 includes third interactive icon 108 to select the corresponding episode plot for inclusion in a report. Each episode plot 106 further includes fourth interactive icon 107 which permits the user to remove the respective ECG plot from interactive display 101. Second side 103 may further include text describing one or more of episode plots 106.

Interactive display 101 further includes graphic window 105 including ECG strip 118 in a second time window starting at the time point selected by the cursor 116. Second graphic window 105 further includes ECG strip 119 in a third time window which is larger than the second time window which is inclusive of the second time window. The third time window includes a shaded portion which corresponds to the second time window.

Figure 10:
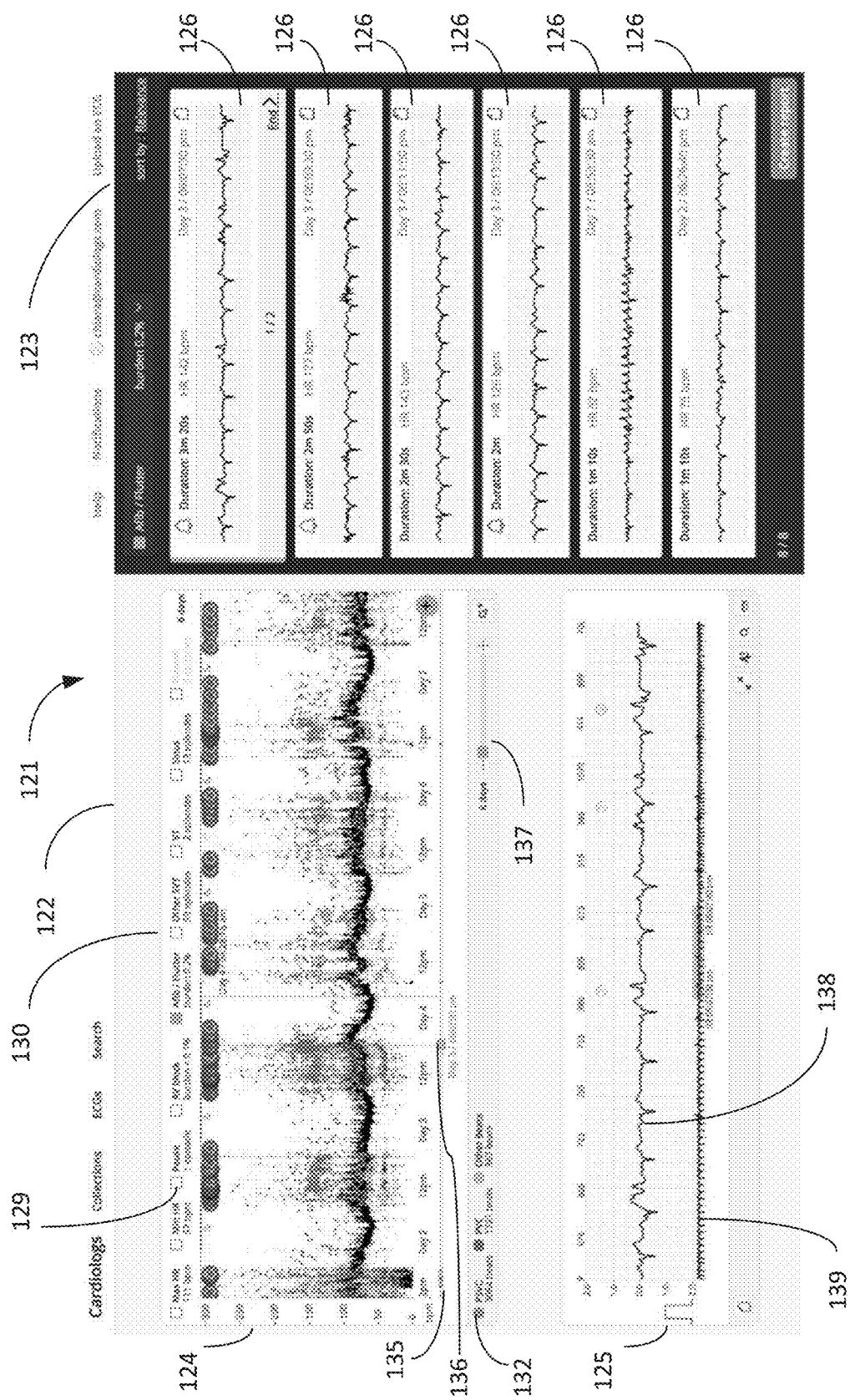
FIG. 10 is an exemplary user interface having a heart rate density plot generated in accordance with aspects of the present disclosure.

Referring now to FIG. 10, a similar display, interactive display 121, is illustrated. Interactive display 121 includes first side 122 and second side 123. First side 122 further includes first graphic window 124 and second graphic window 125. Second side 113 has the same functionality as second side 103 described above, and includes episode plots 126 similar to episode plots 106. Further, second graphic window 125 has the same functionality as second graphic window 105, and includes ECG strip 138 and ECG strip 139 similar to ECG strip 118 and ECG strip 119.

First graphic window 124 is similar to first graphic window 104 except for plot 130. Like first graphic window 104, first graphic window 124 includes multiple label buttons 129 having the same functionality as multiple label buttons 109, secondary labels 132 having the same functionality as secondary labels 112, temporal bar 135 and curser 136 having the same functionality as temporal bar 115 and cursor 116, and second interactive means 137 having the same functionality as second interactive means 117. Unlike plot 110, plot 130 is a heart rate density plot which is the projection onto a bivariate intensity plot of the histogram of the density of heart rates as a function of time.

Figure 11:
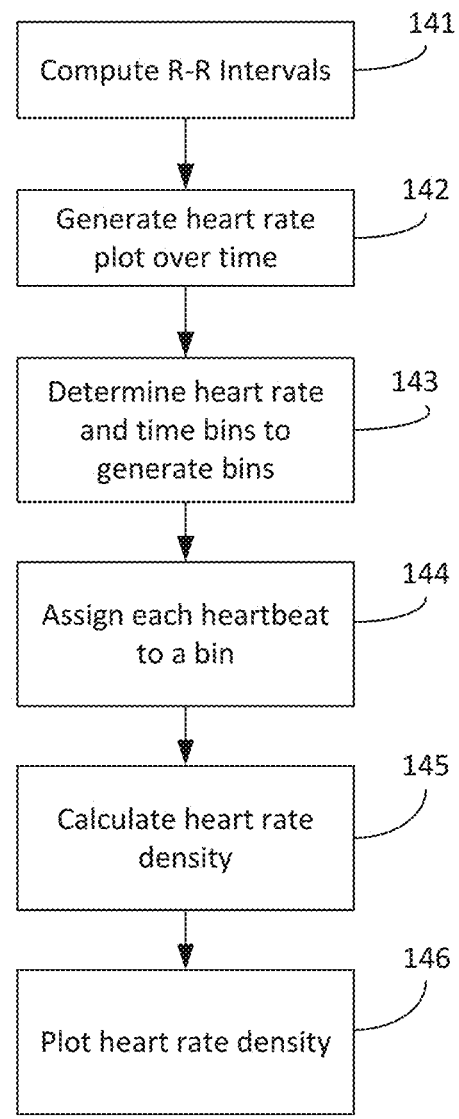
FIG. 11 is a flow chart illustrating an exemplary approach for generating a heart rate density plot.

Referring now to FIG. 11, steps for generating and plotting a heart rate density plot, such as plot 130, are provided. At step 141, ECG platform 37 computes R-R intervals in the cardiac signal (i.e., ECG data). For example, ECG platform 37 may apply the cardiac signal to the delineation neural network to determine the RR intervals, as described above. At step 142, ECG platform 37 may generate the heart rate plot over time. An exemplary heart rate plot, HRDP 150, is illustrated in FIG. 12.

Figure 12:
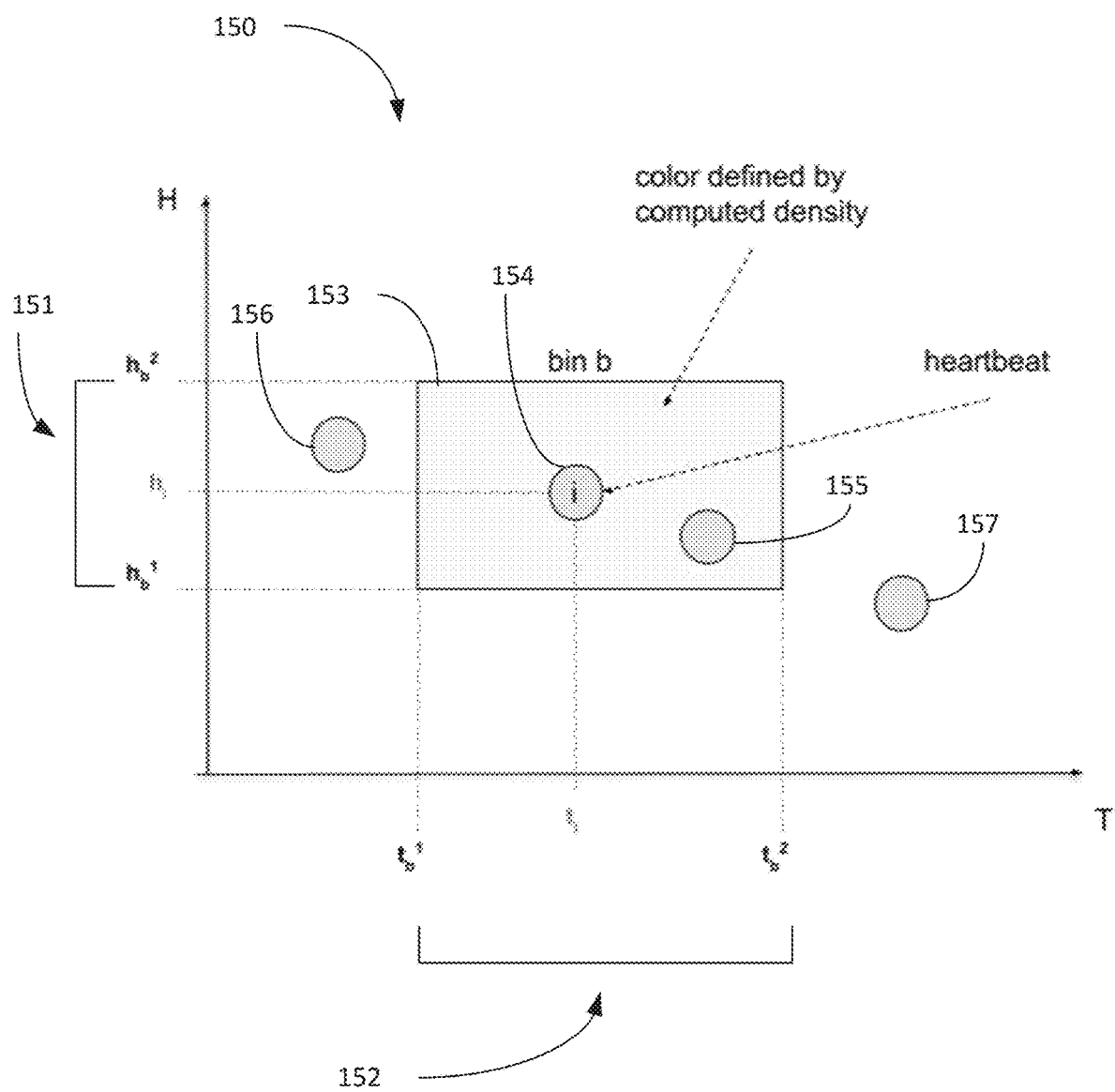
FIG. 12 is an exemplary heart rate density plot generated in accordance with aspects of the present disclosure.

As is shown in FIG. 12, time is projected along the x-axis and the heart rate (e.g., beats per minute) is projected along the y-axis. In one embodiment, both time and heart rate are scaled linearly. However, time and/or heart rate may be scaled logarithmically or using other well-known scales. For simplicity, only four heart beats are shown in FIG. 12.

Referring again to FIG. 11, at step 143, ECG platform 37 may cause the y-axis and the x-axis may be divided into elementary elements, referred to as HR bins and time bins respectively. For example, in FIG. 12, HR bin 151 and time bin 152 are illustrated. HR bin 151 is defined by a first and second heart rate value (e.g., $h_b^1$ and $h_b^2$). Similarly, time bin 152 is defined by a first and second time value (e.g., $t_b^1$ and $t_b^2$). The intersection of a HR bin and a time-bin will be referred to as a bin. In other words, a bin will be defined by a first and second heart rate value and a first and second time value. In FIG. 12, bin 153 is illustrated and defined by HR bin 151 and time bin 152.

Referring again to FIG. 11, at step 144, ECG platform 37 will cause each heartbeat to be assigned to a bin. Specifically, a heartbeat (e.g., QRS complex) that occurs during a time window of a given time bin is included in the computation of the column corresponding to that time bin. Further, a heart rate corresponding to that heartbeat determines which HR bin it belongs to in the column defined by the time bin. For example, in FIG. 12, heartbeat 154 and heartbeat 155 each have a corresponding time and heart rate value that fall within time bin 152 and HR bin 151, respectively. Conversely, heartbeat 156 and heartbeat 157 each have a time value that falls outside time bin 151 and thus neither are included in bin 153.

Referring again to FIG. 11, at step 145, ECG platform 47 will calculate the heart rate density for each time bin. For a given bin, the area defined by the respective time bin and heart rate bin will be represented according to the density of the heart beats comprised in the bin (i.e., number of heartbeats within the bin). Each bin may then be color coded according to the density. For example, each bin may have certain shades of colors or patterns, such as grey levels, for example. In the example in FIG. 12, bins may be represented as levels of grey that get darker as the density of heart rates increases. As is shown in FIG. 12, bin 153, which includes 2 heartbeats, may be represented by a darker shade of grey than a bin with only 1 heartbeat, but a lighter shade of grey than a bin having 3 or more heartbeats.

In a preferred embodiment, the density is calculated as a function of the number of R-waves in the bin divided by the heart rate of the HR bin (e.g. the mean of the minimum and maximum bounds of the time window). This preferred computation of density considers the time spent in a specific bin. For example, in a time bin of 3 minutes, if there occurs 100 beats at a heart rate of 50 bpm (beats per minute) in a first HR bin and 100 beats at 100 bpm in a second HR bin, there will be as many beats in each bin, but 2 minutes will be spent at 50 bpm and only one minute at 100 bpm. Therefore, this bin would have the same density representation if only the number of beats are considered. However, when considering the count of beats divided by the heart rate, the first bin corresponding to the heart rate bin of 50 bpm will be darker than the bin corresponding to the heart rate bin of 100 bpm, as dividing by the heart rate gives higher weight to lower heart rate values. The preferred embodiment therefore captures this temporal information better than only considering the count of beats.

Referring again to FIG. 11, at step 146, ECG platform 37 will plot the heart rate density for each bin. It is understood that capturing temporal information in the column (time bin), in addition to the temporal information naturally given as function of the x-axis, facilitates expression of the density in a manner superior to other forms of aggregated representations of the ECG signal, such as the R-R plot in plot 110.

It is understood that the bounds of the x-axis of the HR density plot may be the beginning and end of the signal. However, in a preferred embodiment, the bounds of the x-axis may interactively vary with the action of zooming in and out performed by the user. The bounds of the y-axis remain fixed when performing this action. Referring again to FIG. 10, plot 130 includes interactive means 137 which may be used to zoom-in on the heart rate density plot. The zoom action may only change the size of the plot display. Alternatively, zooming in and out changes the size of the time window corresponding to a time-bin. With the zooming-in action, a bin represented with the same number of pixels covers a shorter time window. Zooming in therefore causes a new computation of the histogram with finer temporal divisions, and consequently, finer temporal information. This allows for a representation of the ECG signal that shows varying levels of aggregation of the information as a function of the time scale one chooses to display, in order for the histogram to remain both readable and informative at any level of zoom.

Figure 13:
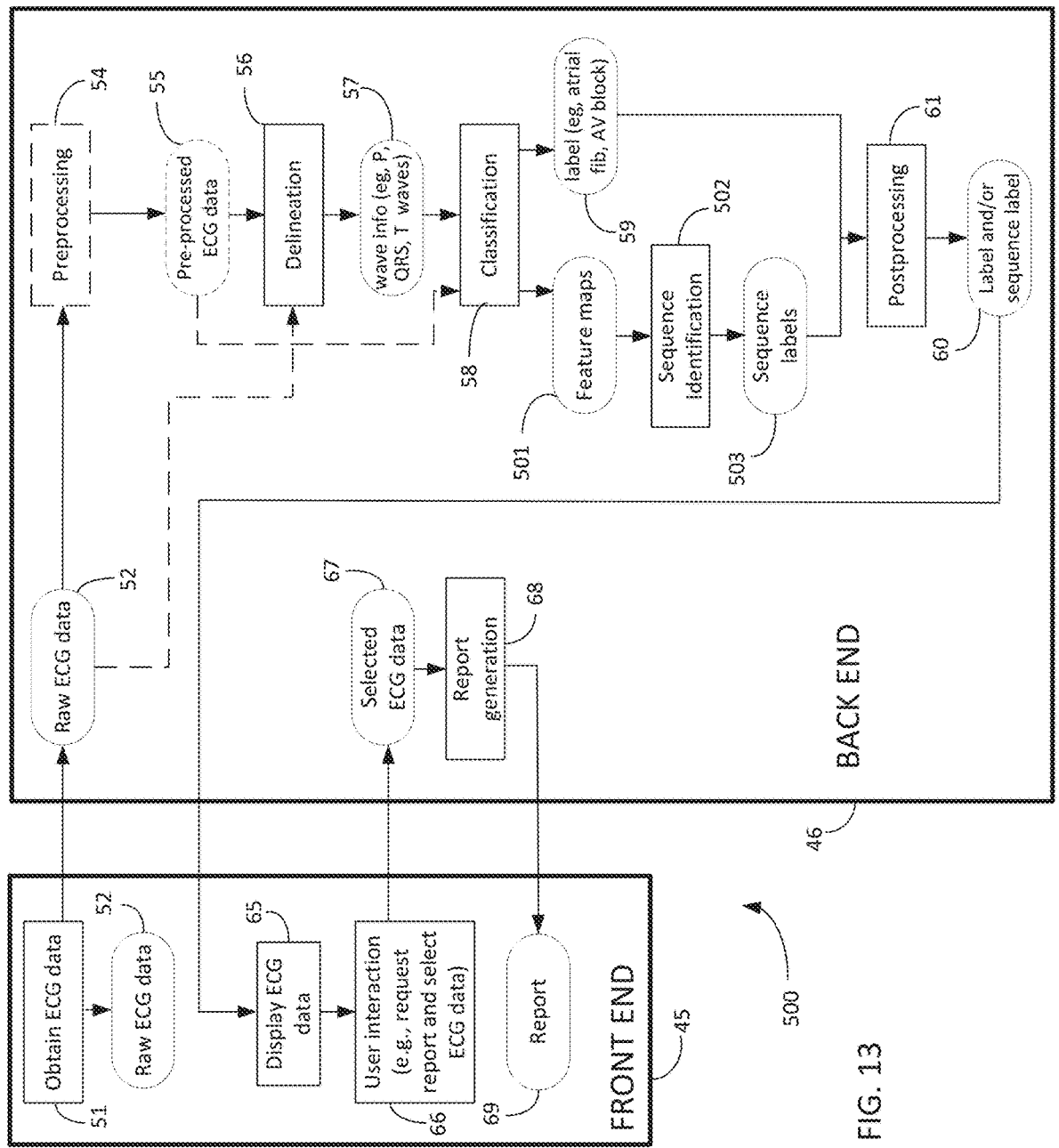
FIG. 13 is a flow chart of an exemplary method of processing ECG data, performing sequence identification, displaying ECG data, and generating a report including ECG data.

Referring now to FIG. 13, an exemplary process for implementing ECG processing system 500 to receive and record ECG data, process and analyze ECG data and sequences of ECG data, and generate reports involving the same is illustrated. FIG. 13, like FIG. 4 shows the flow of information between front end 45 and back end 46 of ECG processing system 10. As explained above, front end 45 includes at least ECG application 29 running on system device 14 and back end 46 includes at least ECG platform 37 running on server 15.

Also similar to FIG. 4, at step 51, ECG application 29 may cause system device 14 to receive and/or otherwise obtain raw ECG data 52 from sensing device 13. Upon receiving raw ECG data 52, ECG application 29 may optionally cause system device 14 to record raw ECG data 52 and may optionally save some or all of raw ECG data 52 to system device 14. As explained above, the signals may correspond to one or more leads. System device 14 may optionally display raw ECG data 52 or a portion thereof on display 17.

As is shown in FIG. 13 and explained above with respect to FIG. 4, raw ECG data 52 may be transmitted from front end 45 to back end 46 by ECG application 29 causing system device 14 to communicate raw ECG data 52 to ECG platform 37 running on server 15. Upon receiving raw ECG data 52, ECG platform 37 may cause server 15 to save some or all of raw ECG data 52 to server 15. Further, after receiving raw ECG data 52, ECG platform 37 may optionally cause raw ECG data 52 to be preprocessed at step 54 by pre-processor 38. Applying raw ECG data 52 to pre-processor 38 may generate pre-processed ECG data 55. Pre-processor 38 may process raw ECG data 52 as explained above with respect to FIG. 4. At this point, ECG platform 37 may cause pre-processed ECG data 55 to optionally be communicated to ECG application 29 running on system device 14 for display on display 17. ECG platform 37 may alternatively, or additionally, cause pre-processed ECG data 55 to be used as an input at classification step 58. Alternatively, raw ECG data 52 may be used as an input at classification step 58.

At step 56, ECG platform 37 causes pre-processed ECG data 55 or raw ECG data 52 to be applied to delineator 39 for delineation. As explained above, delineator 39 applies a first neural network that is a delineation neural network to pre-processed ECG data 55 or raw ECG data 52 and may cause some or all of the ECG data to be expressed as matrix X, which may be a matrix of real numbers. While the ECG data applied to the first neural network is preferably pre-processed ECG data 55, it is understood that a non-preprocessed cardiac signal (i.e., raw ECG data 52, or a portion thereof) may be applied to the first neural network. The first neural network may provide as an output, values corresponding to the likelihood of the presence of or one or more waves at a plurality of time points in the cardiac signal. The first neural network may be a convolutional neural network, and is preferably a fully convolutional neural network. Accordingly, at step 56, delineator 39 causes the first neural network to read each time point of the cardiac signal, spatio-temporally analyze each time point of the cardiac signal, and assign a score at each time point corresponding to one or more types of waves.

The output of the first neural network may be a matrix Y, which may be a matrix of real numbers. For example, matrix Y may be a matrix of the size p×n as explained above. Matrix Y may include scores for each type of wave at each time point of the cardiac signal and each wave type may be expressed according to certain characteristics of that wave, such as start and end points (i.e., onset and offset). The output of the first neural network may detect beats in the input ECG data or may be used to detect beats in the ECG data. ECG platform 37 may cause the output of step 56 (e.g., wave information 57) as well as pre-processed ECG data 55 or raw ECG data 52 to be communicated or otherwise applied to classifier 41 for classification at step 58.

As explained above with respect to FIG. 4, classification at step 58 involves applying a second neural network (i.e., classification neural network) to pre-processed ECG data 55 or raw ECG data 52. Classifier 41 may also process wave information 57 and/or other information such as patient-specific information including the patient's age or any relevant clinical information. ECG platform 37 may optionally cause pre-processed ECG data 55 or raw ECG data 52 to be communicated directly to classifier 41 and processed by classifier 41 if delineation at step 56 is not necessary. It is understood that the first neural network and the second neural network may alternatively be a single neural network that performs the functions and operations of the first neural network and the second neural network.

As explained above with respect to FIG. 4, at step 58, the second neural network may generate an output having values that correspond to the likelihood of the presence of one or more abnormality, condition and/or descriptor at each time point of the cardiac signal. If a time point or time window is determined to correspond to a certain abnormality, condition, and/or descriptor, a label corresponding to that abnormality, condition, and/or descriptor will be assigned to that time point or window as label 59. In one example, one or more labels 59 may be assigned to a time point or time window if a score achieves a predetermined threshold. In addition, at step 58, the second neural network may determine feature maps 501 corresponding to raw ECG data 52, ECG data 54 and/or wave information 57 input into the second neural network.

At step 502, feature maps 501 may be extracted by sequence analyzer 50 which may be one or more algorithms and/or a third neural network. For example, the third neural network, may be a recurrent neural network. Sequence analyzer 50 may analyze feature maps 501 to determine one or more sequence labels 503 and thereby achieve sequence identification of the ECG data.

Figure 14:
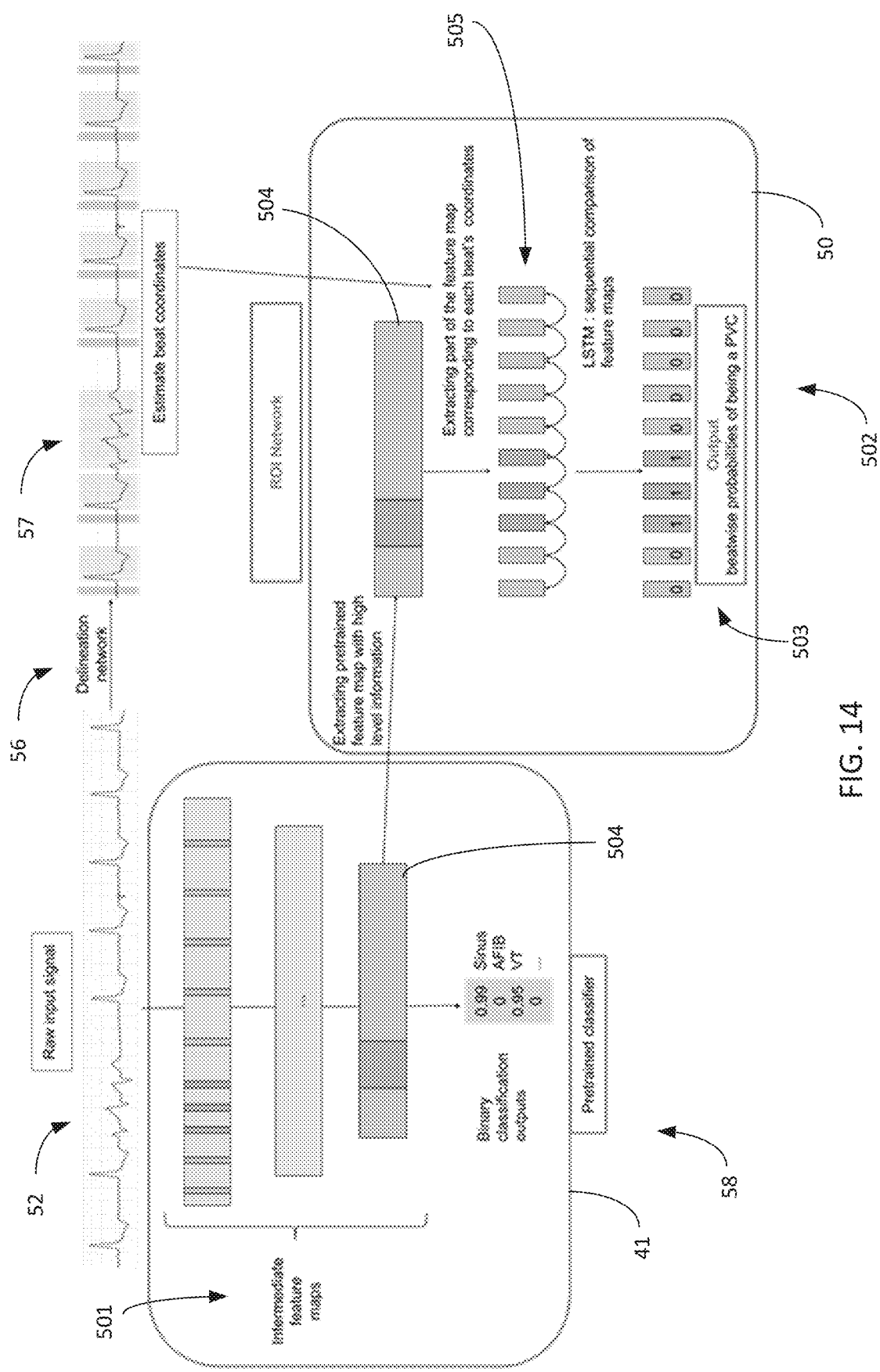
FIG. 14 is an exemplary representation of a process for applying a classification neural network and extracting feature maps for analysis by a sequence analyzer.

Referring now to FIG. 14, steps 56, 58, and 502 are illustrated. As shown in FIG. 14, raw ECG data 52 is shown entering the first neural network (i.e., the delineation neural network) which outputs wave information 57. FIG. 14 further illustrates the classifier 41 and sequencer analyzer 50. ECG data 52 and/or wave information 57 may be applied by classifier 41 as inputs to the second neural network (i.e., the classification neural network), as described above with respect to FIG. 13. The classification neural network may be a convolutional neural network with a few convolutional layers and then standard layers so as to provide a classification. The ECG signal is given as input to the network, which aggregates the information locally and then combines it layer by layer to produce a high-level multi-label classification of the ECG.

As shown in FIG. 14, units of the layers of the neural network may be segmented into feature maps 501. Feature maps 501 may represent the output of filters applied to a the ECG data and may be used to identify certain features in the input to the neural network (e.g., the ECG data). A feature map 504 may include high level information such (e.g., information about a ventricular tachycardia run (e.g., 3 PVCs in a row)). Accordingly, classifier 41 may project the beats determined by the delineation neural network onto feature maps to create a fixed size feature for each beat.

The feature maps 501 determined by classifier 41 may be extracted by sequence analyzer 50 at step 502. Sequence analyzer 50 may further extract or otherwise break up the feature map corresponding to each beat's coordinates, resulting a feature map portions 505. Feature map portions 505 may be organized in sequence according the position of each beat in the ECG data. Sequence analyzer 50 may feed the third neural network (e.g., long short-term memory or simple recurrent neural network) with the sequence of feature map portion 505. The third neural network, being a recurrent neural network, may analyze each feature map portion 505 with respect to the neighboring feature map portions and/or earlier sequence map portions to extract information about the sequence of feature map portions 505. The third neural network, being a recurrent neural network may be trained end-to-end. The third neural network may output probabilities for feature map portion 505 corresponding to certain sequence labels 503.

Sequence labels 503 may be assigned to a beat associated with one beat map portion 505 and may indicate information determined based on the surrounding beats and/or the sequence of beats. For example, sequence labels 503 may include ectopic, supraventricular, PVC, or normal labels. It is further understood that the probabilities for each feature map portion 505 may be processed using a threshold to determine the presence of a sequence label. As shown in FIG. 14, the beat map portions corresponding to PVC (e.g., the beat map portions in red) are assigned "1" for satisfying the PVC threshold value, and the other beat map portions of the ECG data strip (e.g., the beat map portions in green) are assigned "0" for not satisfying the threshold.

Referring again to FIG. 13, after determining feature maps 501 and labels 59 at step 58, and after determining sequence identification 502 and sequence labels 503, step 61 is initiated as described above with respect to FIG. 4. Specifically, at step 61, ECG platform 37 may cause labels for each time window (i.e., labels) to be aggregated by post-processor 43 to generate processed labels 60. The labels may be labels 59 and/or sequence labels 53. Post-processor 43 may also filter the labels to remove redundant labels, assemble labels according to a known hierarchy of labels, or ignore labels that are known to be of lesser importance according to a hierarchy or weighted values. Post-processor 43 may also aggregate the labels through time so as to compute the start (onset) and end (offset) times of each abnormality. It is understood that post-processor 43 may be a standalone component or may be a subcomponent of classifier 41.

As explained above with respect to FIG. 4, the information generated on back end 46 by ECG platform 37 in steps 54, 56, 58, 502, 61 may be communicated by ECG platform 37 to ECG application 29 on front end 45. ECG application 29 may cause the foregoing information to be displayed, at step 65, on display 17 of system device 14. Further, at step 66, the user may request a report and may select customized features such as certain data to be included in the report (e.g., abnormality/condition data, episode data, episode plots, etc.). At step 67, ECG application 29 may transmit the request for a report and selected customizable features (e.g., ECG data to be included in the report) to ECG platform 37 and ECG platform 37 may receive the request and information. ECG platform 37 may log the request and save the information received from ECG application 29. At step 68, ECG platform 37 may cause report generator 44 to generate a report 69 according to the information received from system ECG application 29.

Figure 15A:
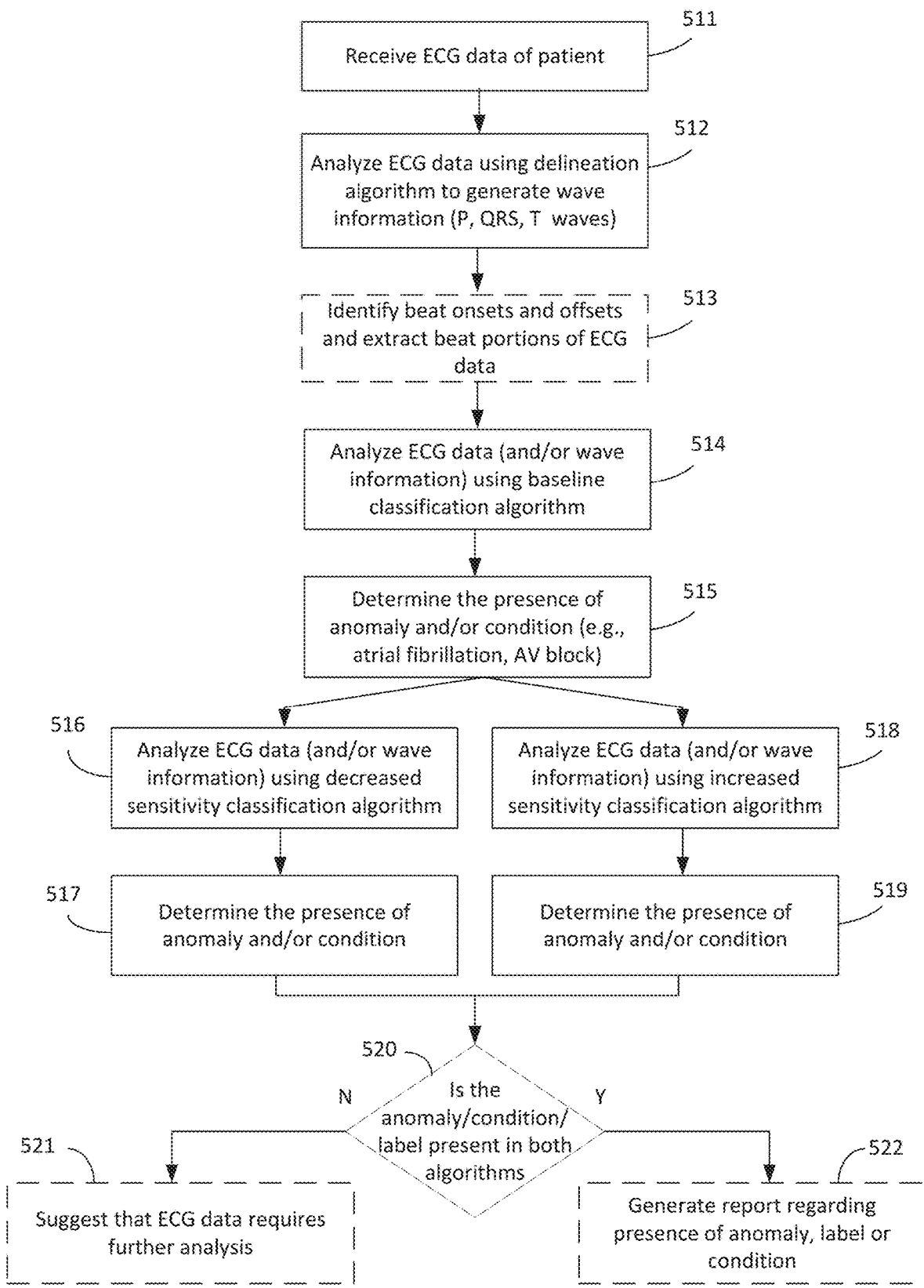

Referring now to FIG. 15A, an exemplary process for determining certainty in a classification system and automatically generating a report regarding the presence of an anomaly and/or condition is illustrated. Steps 511-513 are similar to steps 52 and 56 of FIG. 4, described above. Specifically, at step 511 the system may receive, determine or otherwise obtain ECG data of a patient. At step 512, the ECG data (e.g., raw ECG data or pre-processed ECG data) may be analyzed using a delineation algorithm to generate wave information (e.g., scores corresponding to the likelihood of the presence of a t-wave, p-wave, QRS complex, etc.). Further at optional step 513, beat onsets and offsets may optionally be determined (e.g., based on the wave information) and beat portions of the ECG data may be extracted based on the beat onsets and beat offsets.

At step 514, ECG data (e.g., beat portions and/or wave information) may be analyzed using a classification algorithm having baseline settings. The baseline settings may include a baseline sensitivity determined by training the classification algorithm. Step 514 may be substantially similar to step 58 of FIG. 4, described above. At step 515, the classification algorithm may process the ECG data to determine the presence of an anomaly, label and/or condition (e.g., atrial fibrillation, AV block, normal). For example, the classification algorithm may determine the likelihood of the presence of one or more anomaly, label and/or condition. A threshold may be applied to the likelihood of the presence of the one or more anomaly, label and/or condition to determine the presence of the anomaly, label and/or condition based on whether the likelihood satisfies a threshold value.

At step 516, the ECG data analyzed at step 514 may be analyzed by a classification algorithm with decreased sensitivity as compared to the classification algorithm in step 514. The classification algorithm with decreased sensitivity may be determined by training the algorithm to have decreased sensitivity. For example, the classification algorithm in step 516 may be trained to identify the presence of one or more anomaly, label, and/or condition more often than the baseline classification algorithm in step 514 given the same ECG data. At step 517, the presence of the anomaly, label and/or condition corresponding to step 516 may be determined similar to step 515.

At step 518, the ECG data analyzed at step 514 and/or corresponding wave information may be analyzed by a classification algorithm with increased sensitivity as compared to the classification algorithm in step 514. The classification algorithm with increased sensitivity may be determined by training the algorithm to have increased sensitivity. For example, the classification algorithm in step 516 may be trained to identify the presence of one or more anomaly, label, and/or condition less often than the baseline classification algorithm in step 514 given the same ECG data. At step 519, the presence of the anomaly, label and/or condition corresponding to step 518 may be determined similar to step 515. It is understood that steps 516-517 and steps 518-519 may occur in parallel or in series.

At decision 520, ECG system (e.g., ECG platform 37) may determine whether the anomaly/condition/label determined to be present at steps 514 and 515 is also determined to be present at steps 516 and 517 as well as 518 and 519. Accordingly, at decision 520, the system determines whether the decreased sensitivity classification algorithm and increased sensitivity classification algorithm also result in a determination that the anomaly, label, and/or condition are present.

If the anomaly, label, and/or condition are determined not to be present based on one or more of the decreased sensitivity classification algorithm and increased sensitivity classification algorithm then the determination of the presence of the anomaly, label and/or condition by the baseline classification algorithm (e.g., at steps 514 and 515) is identified as uncertain and at optional step 521, the system may suggest and/or recommend that the ECG data requires further analysis (e.g., by a user).

Alternatively, if the anomaly, label, and/or condition are determined to be present based on both the decreased sensitivity classification algorithm and increased sensitivity classification algorithm then the determination of the presence of the anomaly, label and/or condition by the baseline classification algorithm (e.g., at steps 514 and 515) is identified as certain and at optional step 522 a report based on the presence of the anomaly, label, and/or condition may be generated. For example, the report may be generated according to steps 68 and 69 of FIG. 4, described above. In one example, the report may be fully automatic and thus may be generated without any human interaction. It is understood that the process described in 516-520 may be a standalone set of algorithms or may be one or more layers on top of the classification neural network. It also is understood that the steps described in FIG. 15A may be performed in addition to or along with other operations set forth herein included those described above with respect to FIG. 4.

It is further understood that the certainty of the classification algorithm may alternatively be determined by, or may be further informed by, determining the area under the curve (AUC) for a Receiver Operating Characteristic (ROC) Curve. Specifically, the sensitivity of the neural network may be plotted against 1-specificity and the area under the curve may inform the accuracy of the model. The specificity may be determined by dividing the number of true positives by the sum of the true positives and the false negatives. Further "1-specificity" may be determined by the number false positives by the sum of false positives plus true negatives. An area under the curve value close to 1 may indicate an accurate model.

Referring now to FIG. 15B, robust classification system 565 is illustrated. Similar to the process described above with respect to FIG. 15A, robust classification system 565 may be a component of the ECG processing systems described above (e.g., ECG processing system 10, ECG processing system 10' and/or ECG processing system 500). For example, ECG processing system 565 may replace or otherwise supplement classification step 58. Specifically, robust classification module 568 may replace classification step 58. Robust classification module 568 may include classifier 569 which may be the same or similar to classifier 41, described above. Specifically, classifier 569 may execute a neural network to achieve classification. Classifier 569 may receive pre-processed ECG data 566 as well as RR data 567 as inputs. Pre-processed ECG data 566 may be the same as pre-processed ECG data 56, described above. Further RR data 567 data may be the output of a delineation neural network such as the output of delineation step 56, described above. For example, RR data 567 may be the same as wave information 57, described above.

As shown in FIG. 15B, classifier 569 may process pre-processed ECG data 566 and RR data 567 to determine AFib probability 571, similar to classifier 41 in classification step 58, described above. AFib probability 571 is the likelihood that pre-processed ECG data 566 includes an episode of atrial fibrillation. The output of classifier 569, pre-processed ECG data 566 and/or RR data 567 may also be applied to and processed by confidence estimator 570 to determine confidence score 572 which may correspond to the likelihood that AFib probability 571 is accurate and/or certain. Confidence estimator 570 may be one or more algorithms (e.g., a neural network) and may have the same classifier structure (e.g., architecture) as classifier 569, but may be trained to be more specific. For example, confidence estimator 570 may perform steps similar to steps 516-517, described above with respect to FIG. 15A.

Referring now to FIG. 15C, robust classification system 573 is illustrated and is similar to robust classification system 565, but includes robust classification module 574. Also similar to robust classification system 565, robust classification system 573 may replace or otherwise supplement classification step 58, described above. Robust classification module 574 may receive ECG pre-processed data 566 and RR data 567 and may output AFib probability 571 and confidence score 572, similar to robust classification module 568. Unlike robust classification module 568, robust classification module 574 may include confidence classifier 575 instead of classifier 569 and confidence estimator 570. Confidence classifier 575 may be one neural network that performs the same functions and operations of classifier 569 and confidence estimator 570 to output AFib probability 571 and confidence score 572.

Figure 15D:
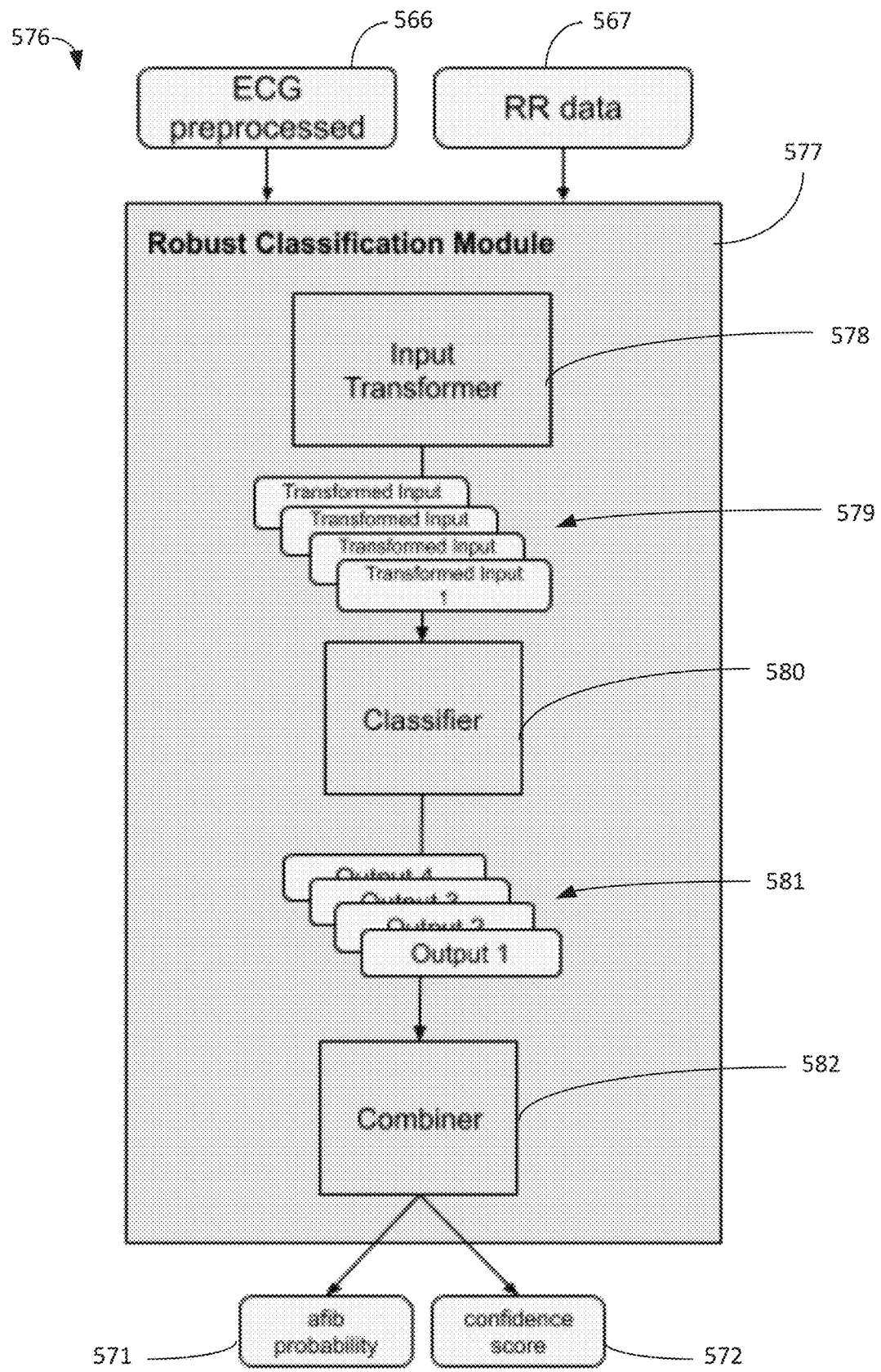

Referring now to FIG. 15D, robust classification system 576 is illustrated. Similar to robust classification system 565 and robust classification system 573, robust classification system 576 includes pre-processed ECG data 566 and RR data 567 as inputs and may replace or otherwise supplement classification step 58, described above. ECG classification system 576 may include robust classification module 577.

Robust classification module 577 may include classifier 580 which may be the same or similar to classifier 41, described above. Specifically, classifier 580 may execute a neural network to achieve classification. Robust classification module 577 may further include input transformer 578 and combiner 582. Input transformer 578 may process inputs to robust classification module 577 (e.g., pre-processed ECG data 566 and/or RR data 567) and may apply transformations to such inputs. Transformations may be amplifications, dilation, and/or lead selection, for example. An amplification transformation may amplify the signal (e.g., pre-processed ECG data 566) using a float value. A dilation transformation may involve the signal (e.g., pre-processed ECG data 566) being warped in time and the RR data 567 being consequently adjusted and/or otherwise modified. If the ECG data received by the ECG system corresponds to more than one lead, subsets of data (e.g., pre-processed ECG data and/or RR data) may be saved and/or maintained and may be retrieved. By applying pre-processed ECG data 566 and RR data 567 to input transformer 578, transformed inputs 579 may be generated. Transformed inputs 579 may include several (e.g., four) transformed copies of the same signal. While four transformed inputs 579 are illustrated in FIG. 15C, it is understood that any number of transformed inputs may be generated. It is further understood that amplification, dilation, lead selection and/or any other transformation technique may be used to generate transformed inputs 579.

As shown in FIG. 15D, transformed inputs 579 may be applied to and processed by classifier 580. Like classifier 569, classifier 580 may be the same or similar to classifier 41, described above. Specifically, classifier 580 may execute a neural network to achieve classification. Classifier 580 may generate outputs 581. Classifier 580 may process each copy of transformed inputs 579 and may generate an output for each copy. Accordingly, if transformed inputs 579 includes four transformed copies of the signal, classifier 580 may generate four outputs.

Robust classification module 577 may further include combiner 582. Outputs 581 may be applied to and processed by combiner 582. Combiner 582 may take the outputs of classifier 580, which have the same format (e.g., size N) and combine the outputs. For example, combiner 582 may combine outputs 581 by taking an average of outputs 581, which may result in a single output that may have size N. Alternatively, to achieve more sensitivity, combiner may instead determine a maximum value of outputs 581. Similarly, to achieve less sensitivity, combiner may instead determine a minimum value of outputs 581. Combiner 582 may output AFib 571 and Confidence score 572. For example, classifier 580 may be similar to confidence classifier 575 and one set of outputs 581 corresponding to AFib probability 571 may be generated in addition to a second set of outputs 581 corresponding to confidence score 572. Combiner may process the different output sets separately to result in AFib probability 571 and confidence score 572. Alternatively, combiner 582 and/or classifier 580 may be similar to confidence classifier 575 and together may determine AFib probability 571 and confidence score 572.

Figure 15E:
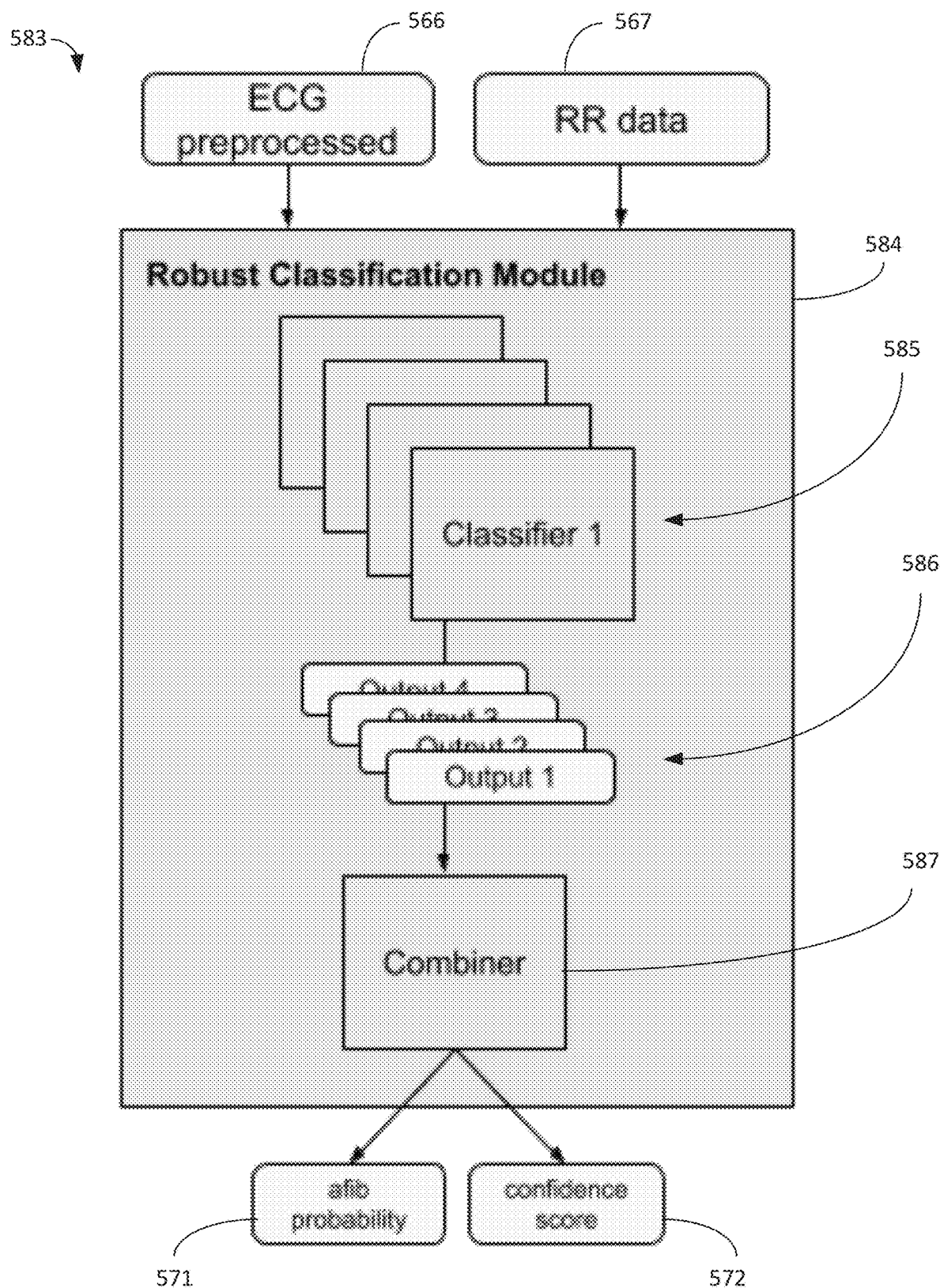

Referring now to FIG. 15E, robust classification system 583 is illustrated. Similar to robust classification system 565, robust classification system 573, and robust classification system 576, robust classification system 583 includes pre-processed ECG data 566 and RR data 567 as inputs and may replace or otherwise supplement classification step 58, as described above. ECG classification system 583 may include robust classification module 584.

Robust classification module 584 may include classifiers 585 which may be several distinct classifiers which each may be the same or similar to classifier 41, described above. Specifically, classifiers 581 each may execute a neural network to achieve classification. Each classifier may be trained differently (e.g., using a different dataset and/or each having different weights). For example, classifiers 581 may each be the same structure (e.g., architecture) with different weights, yielding different classifiers. As shown in FIG. 15E, classifiers 381 could include four classifiers that each were trained using four different training datasets and consequently have different sets of weights. This may result in classifiers with varying degrees of sensitivity (e.g., some classifiers with lower and/or higher sensitivity than others). The same pre-processed ECG data 566 and/or RR data 567 may be input and processed by each classifier of classifiers 585. Each classifier of classifier 585 may then generate a corresponding output. Together, classifiers 585 generate outputs 586.

Robust classification module 584 may further include combiner 587. Outputs 586 may be applied to and processed by combiner 587. For example, combiner 587 may take the outputs of classifier 586, which have the same format (e.g., size N for example) and combine the outputs. The combiner may combine outputs 586 by taking an average of outputs 586, which may result in a single output of size N. Alternatively, to achieve more sensitivity, combiner may instead determine a maximum value of output 586. Similarly, to achieve less sensitivity, combiner may instead determine a minimum value of output 586. Combiner 587 may output AFib 571 and Confidence score 572. For example, classifiers 585 may be similar to confidence classifier 575 and for each classifier, one output of outputs 586 corresponding to AFib probability 571 may be generated in addition to second output of outputs 581 correspond to confidence score 572. Combiner may process the different output sets separately to result in AFib probability 571 and confidence score 572. Alternatively, combiner 587 and/or classifiers 586 may be similar to confidence classifier 575 and together may determine AFib probability 571 and confidence score 572.

Based on the AFib probability 571 and confidence score 572, the ECG system may determine there is no atrial fibrillation present with high confidence, that there is no atrial fibrillation present with low confidence, that there is atrial fibrillation present with high confidence, or that there is there is atrial fibrillation present with high confidence. If confidence is low, the corresponding ECG signal will be identified as uncertain. If the confidence is high, the ECG signal will be qualified and/or otherwise identified as having atrial fibrillation or not having atrial fibrillation. If the ECG signal is qualified as having atrial fibrillation or not having atrial fibrillation, the ECG system will generate a report. For example, the report may include the daily heart rate trend, the most relevant ECG strips of the ECG data based on certain criteria (e.g., the beginning of an atrial fibrillation episode, the fastest atrial fibrillation episode, etc.), and/or the conclusion and/or determination about the presence of atrial fibrillation. If the ECG signal is qualified as uncertain, the ECG signal may be flagged and/or submitted for human review.

It is understood that the approaches illustrated in FIGS. 15D and 15E and described above could be combined to include a robust classification system including the input transformer as well as multiple classifiers, each trained differently. For example, the approaches could be combined into a robust classification module which takes a signal and transforms it into N modified signals, which are each input into M classifiers, which provides N*M outputs that can be applied to a combiner to determine the AFib probability and confidence score.

It is also understood while pre-processed ECG data 566 is described as an input into classifier 569 and/or confidence estimator 570, raw ECG data may alternatively be input to the robust classification module in FIGS. 15B-E. It is further understood that while FIGS. 15A-E are described above with respect to atrial fibrillation, the same system may be trained to detect any other condition and/or anomaly detectable using ECG data and a corresponding confidence score.

Figure 16:
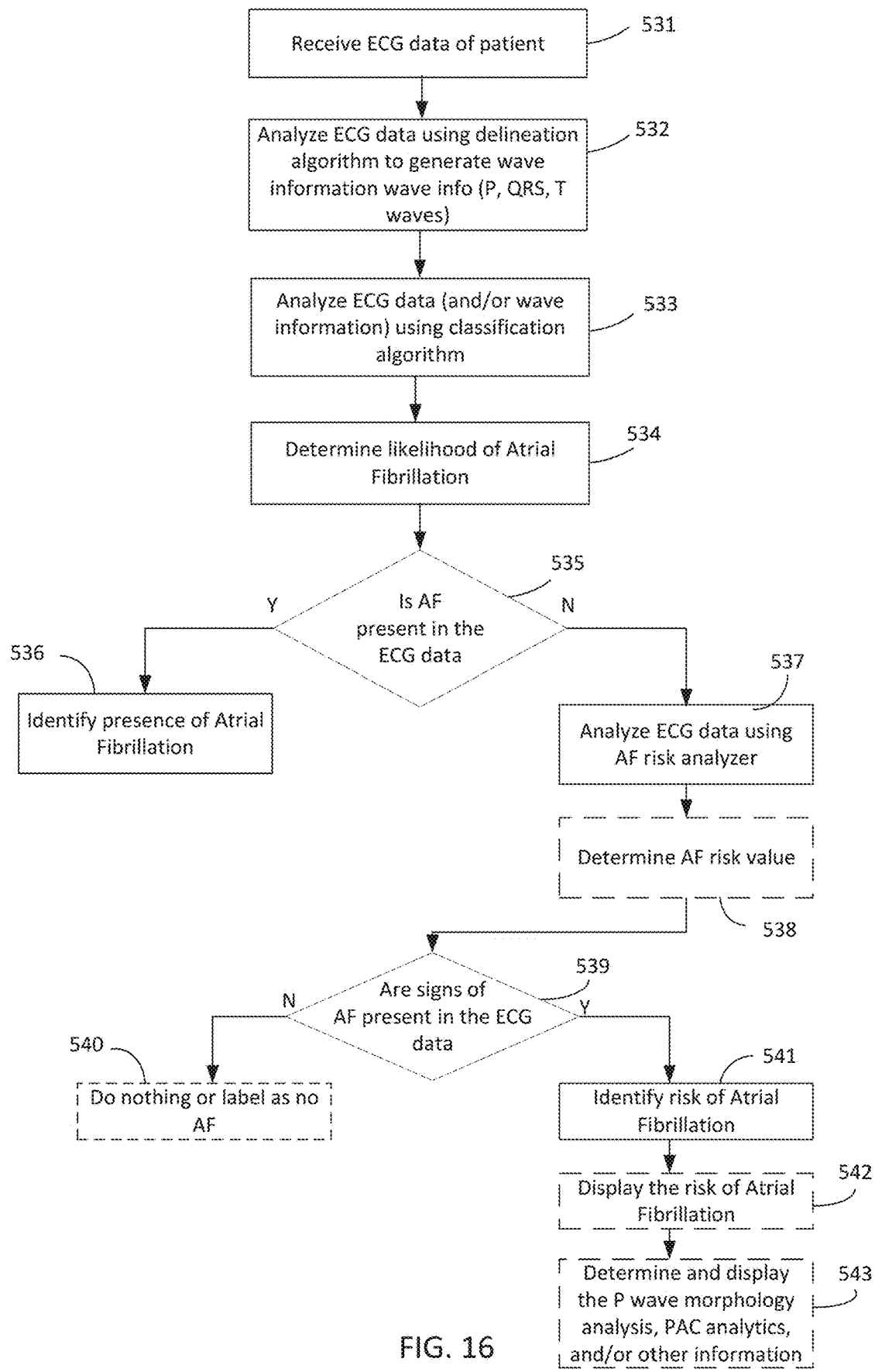
FIG. 16 is an exemplary process for analyzing ECG data and determining the presence of asymptomatic atrial fibrillation.

Referring now to FIG. 16, an exemplary process for determining a risk of a cardiac event (e.g., atrial fibrillation) for ECG data that is asymptomatic with respect to the cardiac event (e.g., devoid of an atrial fibrillation episode) is illustrated. The process may be performed by ECG platform 37. While the process is illustratively described to determine a risk of atrial fibrillation, the process may be used to determine the risk of other cardiac events. Similar to FIG. 15A, the exemplary process in FIG. 16 begins with receiving or obtaining ECG data of patient at step 531 which is similar to step 511, analyzing ECG data using a delineation algorithm to generate wave information at step 532 which is similar to step 512, and analyzing ECG data (and/or wave information) using a classification algorithm at step 533 which is similar to step 514. The process in FIG. 16 further includes step 534 which involves determining a likelihood of atrial fibrillation. Similar to step 515 of FIG. 15A, at step 534 the classification algorithm may process the ECG data to determine the presence of atrial fibrillation. For example, the classification algorithm may determine the likelihood of the presence atrial fibrillation. A threshold may be applied to the likelihood of the presence of atrial fibrillation to determine the presence of atrial fibrillation based on whether the likelihood satisfies the threshold value.

At decision 535, ECG platform 37 may determine whether atrial fibrillation is present in the ECG data based on the determination made at step 534. If it is determined that atrial fibrillation is present in the ECG data, then at step 536, the ECG data may be identified as having atrial fibrillation present. For example, label 59 of FIG. 4 corresponding to atrial fibrillation may be assigned to the ECG data and one or more of steps 61, 65, 66, and 68 of FIG. 4 may be initiated, as described above.

Alternatively, if at decision 535, it is determined that the atrial fibrillation is not present in the ECG data based on the determination made at step 534, the ECG data analyzed at step 533 may be analyzed using an atrial fibrillation (AF) risk analyzer. The AF risk analyzer may be a standalone set of algorithms (e.g., neural network) or may be one or more layers on top of the classification neural network.

The AF risk analyzer may output one or more values indicating the likelihood of the patient corresponding to the ECG data having atrial fibrillation despite no atrial fibrillation being detected at step 534. For example, the AF risk analyzer may be convolutional neural network that may analyze ECG data and or wave information such as morphological and temporal features, for example. The AF risk analyzer may include several blocks (e.g., one or more layers). For example, the AF risk analyzer may include batch normalization layer to account for the normalization of the data distribution and a non-linear rectified linear unit (ReLU) function. The ReLU function may have output zero for negative inputs and identity output for positive inputs to facilitate feature extraction. The blocks may include a shortcut link to permit gradient propagation between layers and/or components of the neural network and may further include a pooling layer, one or more convolution layers, a dropout layer and/or an output layer. It is understood that the AF risk analyzer may be trained using ECG data from patients diagnosed with atrial fibrillation but without atrial fibrillation episodes present in the ECG data to identify or otherwise determine features in the ECG data associated with patients with atrial fibrillation.

At step 538, the output of the AF risk analyzer may be used to determine an atrial fibrillation risk value. For example, the classification algorithm may determine the likelihood of the presence atrial fibrillation. A threshold may be applied to the likelihood of the presence of atrial fibrillation to determine the presence of atrial fibrillation based on whether the likelihood satisfies a threshold value.

At decision 539, the system (e.g., ECG platform 37) may determine whether signs of atrial fibrillation are present in the ECG data. For example, if threshold value is satisfied (e.g., the likelihood of the presence of atrial fibrillation exceeds or is the same as the threshold value) then it may be determined that there are signs of atrial fibrillation in the ECG data. If it determined that there or no signs of atrial fibrillation in the ECG data and/or the threshold value is not satisfied, then at optional step 540, the system may do nothing or may label the ECG data as not having atrial fibrillation. Alternatively, if it is determined that there are signs of atrial fibrillation in the ECG data and/or the threshold value is not satisfied, then at step 541, the risk of atrial fibrillation may be identified. For example, an atrial fibrillation label or risk of atrial fibrillation label may be assigned to the ECG data.

At optional step 542, the system may cause the risk of atrial fibrillation to be displayed on display 17. The risk may be displayed as a score or some indication of risk level. For example, the risk could be displayed as the calculated risk value on a predetermined scale (e.g., 75 out of 100). The risk could also be categorized based on where the calculated risk value falls within predetermined threshold risk ranges (e.g., 0 to 35 out of 100 corresponds to "low," 35 to 70 out of 100 corresponds to "medium," and 70 to 100 out of 100 corresponds to "high.") The categorization may be displayed with or without the calculated risk value. Also, at optional step 543, a P wave morphology analysis, PAC analytics and/or other information corresponding to the risk of atrial fibrillation may be determined as described herein and optionally may be displayed on display 17. It is understood that the steps described in FIG. 16 may be performed in addition to or along with other operations set forth herein included those described with respect to FIG. 4. It is further understood that the risk analyzer may be trained to detect the presence of another anomalies and/or conditions (e.g., a cardiac event) that are asymptomatic in the analyzed ECG data.

Figure 17:
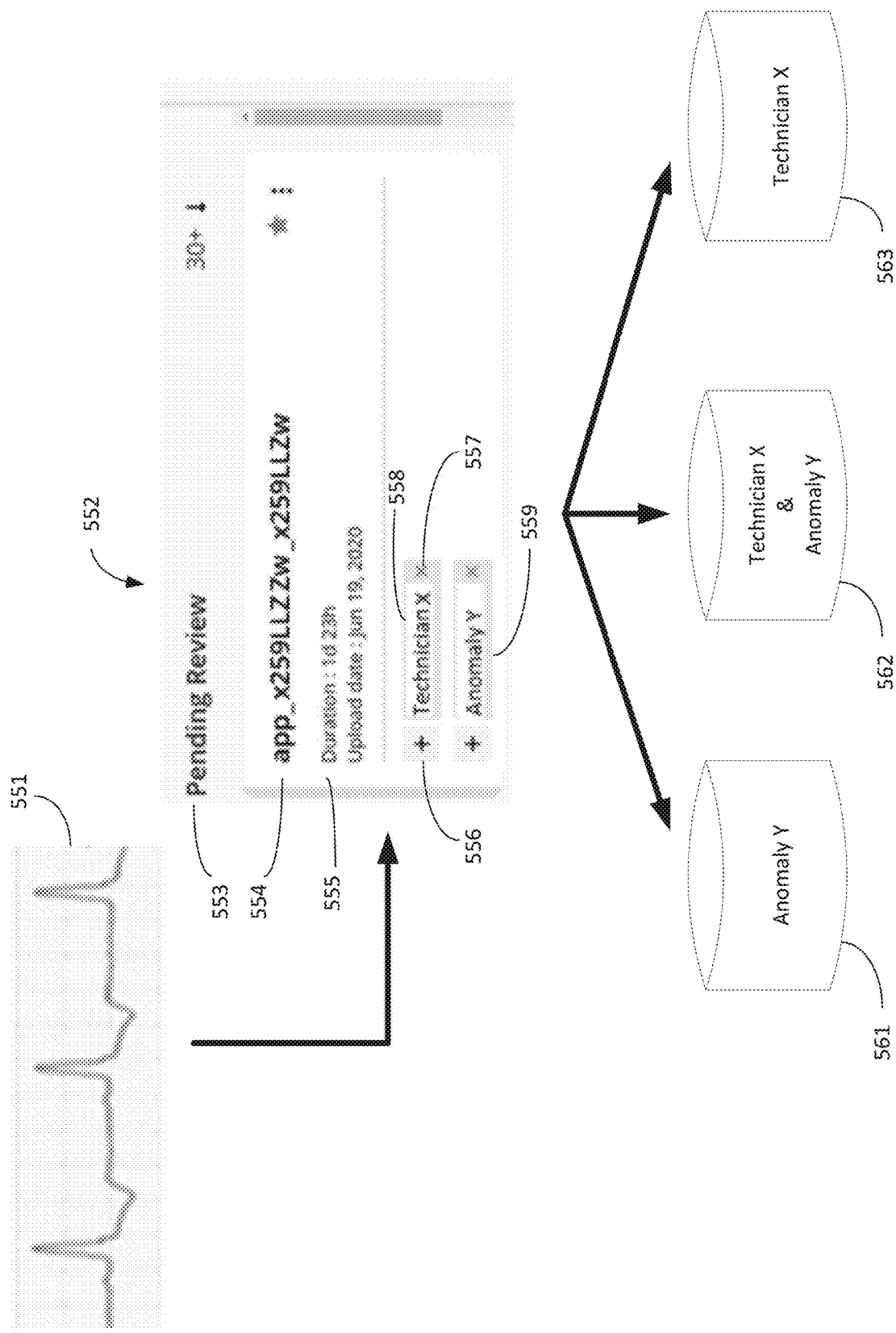
FIG. 17 is an exemplary representation of a process of applying labels to ECG data.

Referring now to FIG. 17, labelling ECG data is illustrated. As shown in FIG. 17, upon determining or otherwise obtaining ECG data 551, the system (e.g., ECG platform 37 and/or ECG application 29) may assign profile 552 to ECG data 551. Profile 552 may be displayed on display 17 and may include certain information about ECG data 551. For example, profile 552 may include review status 553, title 554, and ECG information 555. Review status 553 may include information about whether ECG data 551 has been reviewed. For example, review status 553 may be "pending review" or "reviewed". Title 554 may include letters and numbers associated with ECG data 551 and used to identify ECG data 551. ECG information 555 may include information about ECG data 551 such as recording duration time (e.g., 1 day and 23 hours) and/or upload date (e.g., Jun. 19, 2020).

Profile 552 may include one or more labels assigned to ECG data 551. For example, ECG label 558 and ECG label 559 may be added to profile 552. ECG label 558 may identify a technician or healthcare provider assigned to ECG data 551. ECG label 559 may identify an anomaly, condition, label and/or sequence label assigned to analyze ECG data 551. It is understood that the ECG data may be automatically processed by the delineation and/or classification neural network and thus the system may automatically determine the presence of an anomaly, episode and/or condition in the ECG data and may assign ECG label to profile 552 of ECG data 551 to associate the ECG data with that anomaly, episode or condition. For example, ECG label 559 may say "Anomaly Y". Alternatively, this label may be added manually. Profile 552 may include add button 556 to add a label and/or delete button 557 to delete a label from profile 552. Accordingly, ECG labels 552 may be automatically generated or may be generated by a user.

Various ECG data determined or otherwise obtained by the system may be categorized and/or filtered based on information in profile 552. For example, labels assigned to ECG data 551 in profile 552 may be used to filter ECG data. In the example illustrated in FIG. 17, ECG data 552 may fall into three different groups of ECG data. First, ECG data 551 may be included in group 561 which may include ECG data having Anomaly Y. Second, ECG data 563 may be included in group 563 which may include ECG data assigned to Technician X. Additionally, ECG data 551 may even be grouped into group 562 having both labels, Technician X and Anomaly Y. These groups may be used to view other ECG data associated with the given labels for the respective group. This may be a useful tool for a technician to find ECG data assigned to him/her and/or for a user to view ECG data with similar labels.

It is understood that a profile may include information about ECG data that is not embedded into the ECG data but may impact the way the ECG data is managed in the ECG system. Labels may be visible for all users within the same organization or may otherwise be limited to certain users within an organization.

Figure 18A:
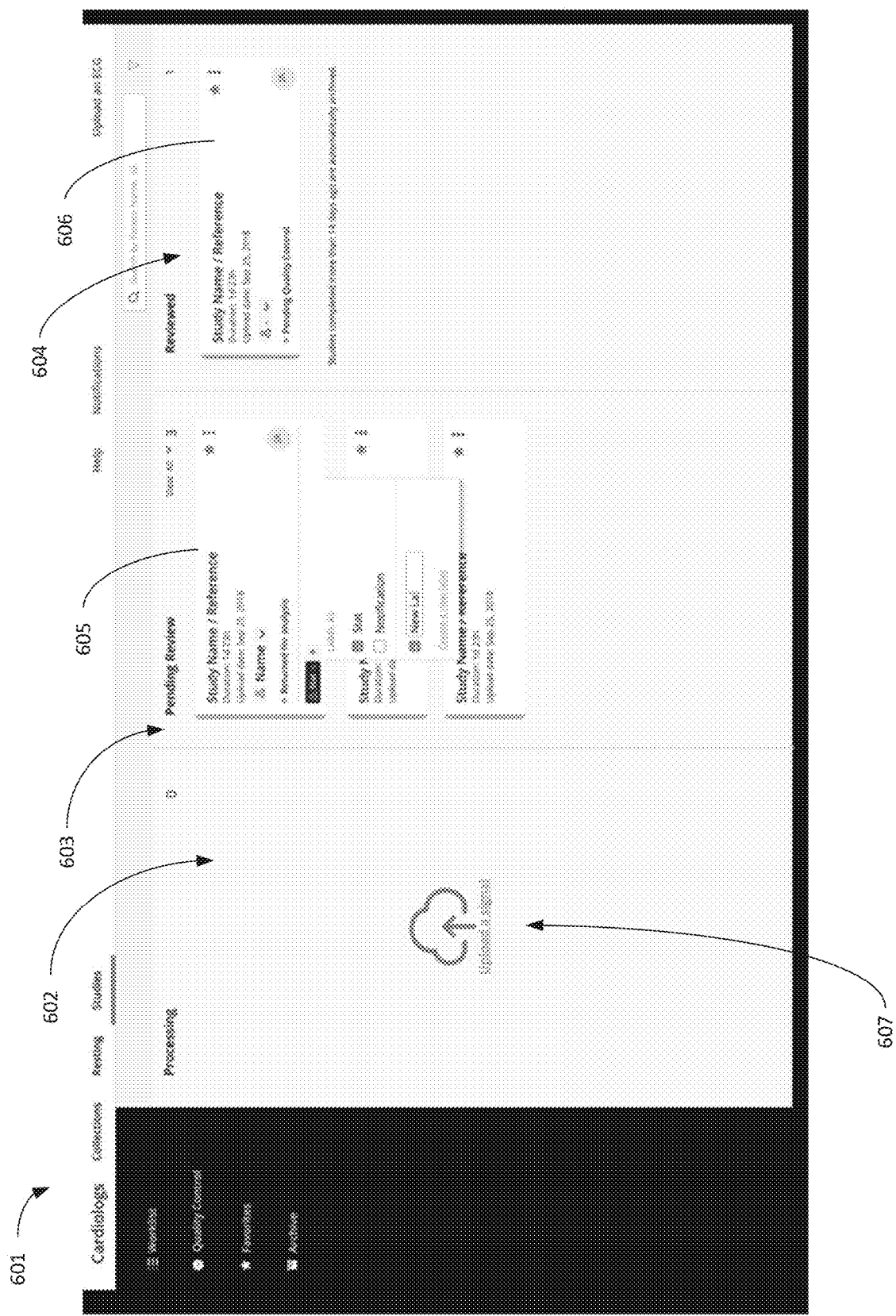
FIGS. 18A-18H illustrate user interfaces for assigning labels and other information to ECG data.

Referring now to FIG. 18A, interface 601 is illustrated. Interface 601 may include processing window 602, pending review window 603 and reviewed window 604. Processing window 602 may include upload button 607 which may be engaged to upload an ECG signal. For example, upload button 607 may cause ECG platform 37 to retrieve an ECG signal from a database or may cause electrodes to obtain the ECG signal. Window 603 may include ECG profiles of ECG signals that have been uploaded but have not been reviewed. For example, profile 605 may be included in pending window 603 and may be similar to profile 552. Additionally, reviewed window 604 may include ECG profiles of ECG signals that have been uploaded and reviewed. For example, profile 606 may be included in reviewed window 606 and may be similar to profile 552.

Figure 18B:
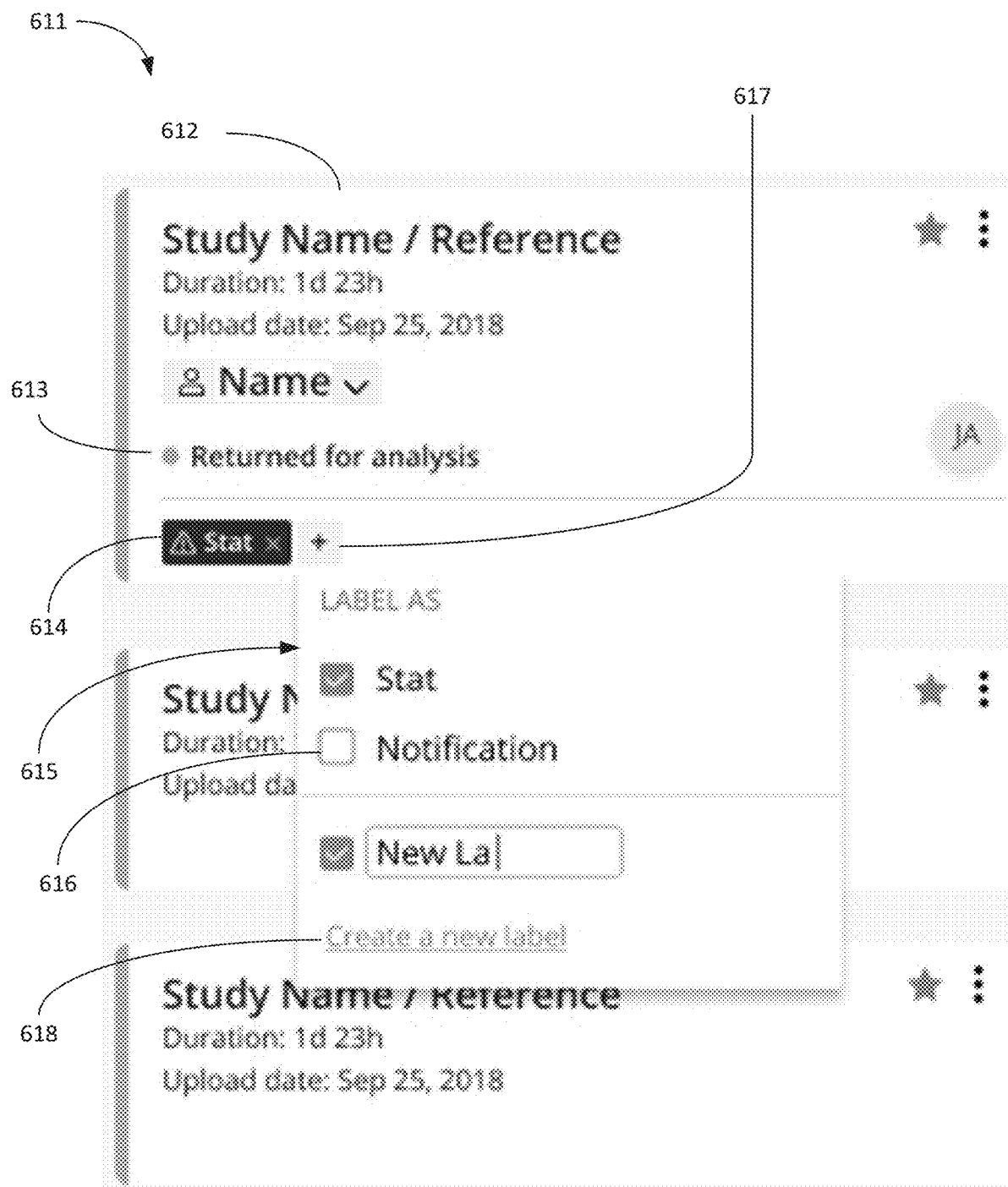

Referring now to FIG. 18B, exemplary profiles 611 is illustrated. Exemplary profiles 611 may be included in processing window 602 or reviewed window 603. Exemplary profile 611 may include profile 612 which may be similar to profile 552 and may include a title, ECG information, and at least one label. As shown in FIG. 18B, profile 552 may include notification 613 stating that the ECG data was "returned for analysis." As explained above, this may happen where the ECG platform 37 does not have a high degree of confidence in the analysis or determination of a condition and/or anomaly. Also shown in FIG. 18B, profile 612 may further include labels such label 614 which may state "stat" to indicate that the ECG data needs to be analyzed. Further, add label button 617 may be engaged to add more labels to profile 612. For example, engage label button 617 may result in label window 615 which may show available labels and selected labels profile 612. In this example, the label "stat" is selected and the label "notification" is available but not selected. Further, create new label button 618 may be included in label window 615 to create a new label for profile 612. The new labels created may be used by any ECG profile. It is understood that certain labels may be available by default (e.g., stat, notification) and/or may not be available to edit.

Figure 18C:
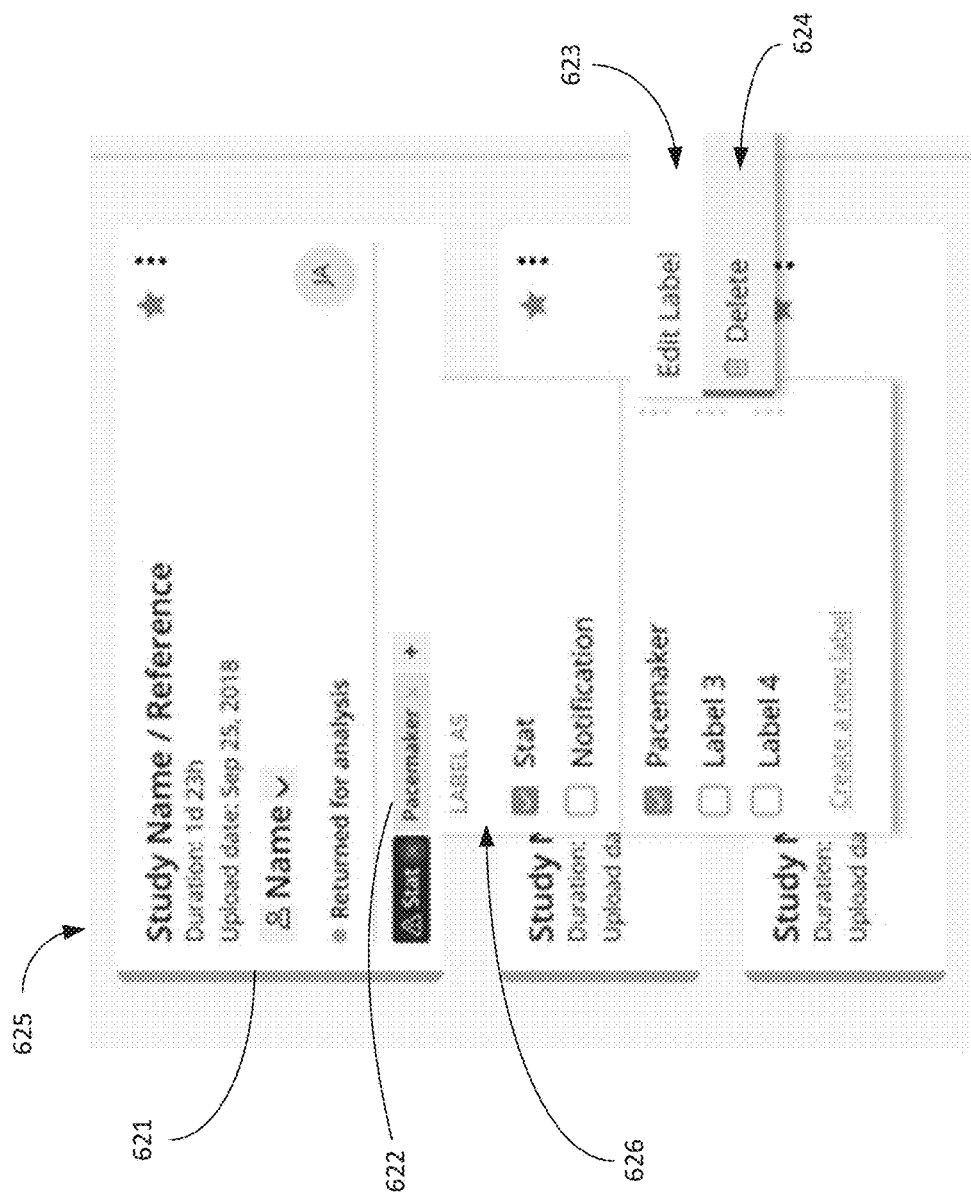

Referring now to FIG. 18C, profiles 625 is illustrated, which may be similar to profiles 611. Profiles 625 may include profile 621 which may be similar to profile 611 as it may include a title, ECG information, and at least one label. For example, profile 621 may include label 622 which may indicate that the patient corresponding to the ECG data for profile 621 has a pacemaker. Label window 626 may be included in profile 621 and may be similar to label window 615. Label window 626 may further include edit button 623 and delete button 624. Edit button 632 may be engaged to edit the name of a label in label window 622. Further, delete button 624 may be engaged to delete a label in label window 626.

Figure 18D:
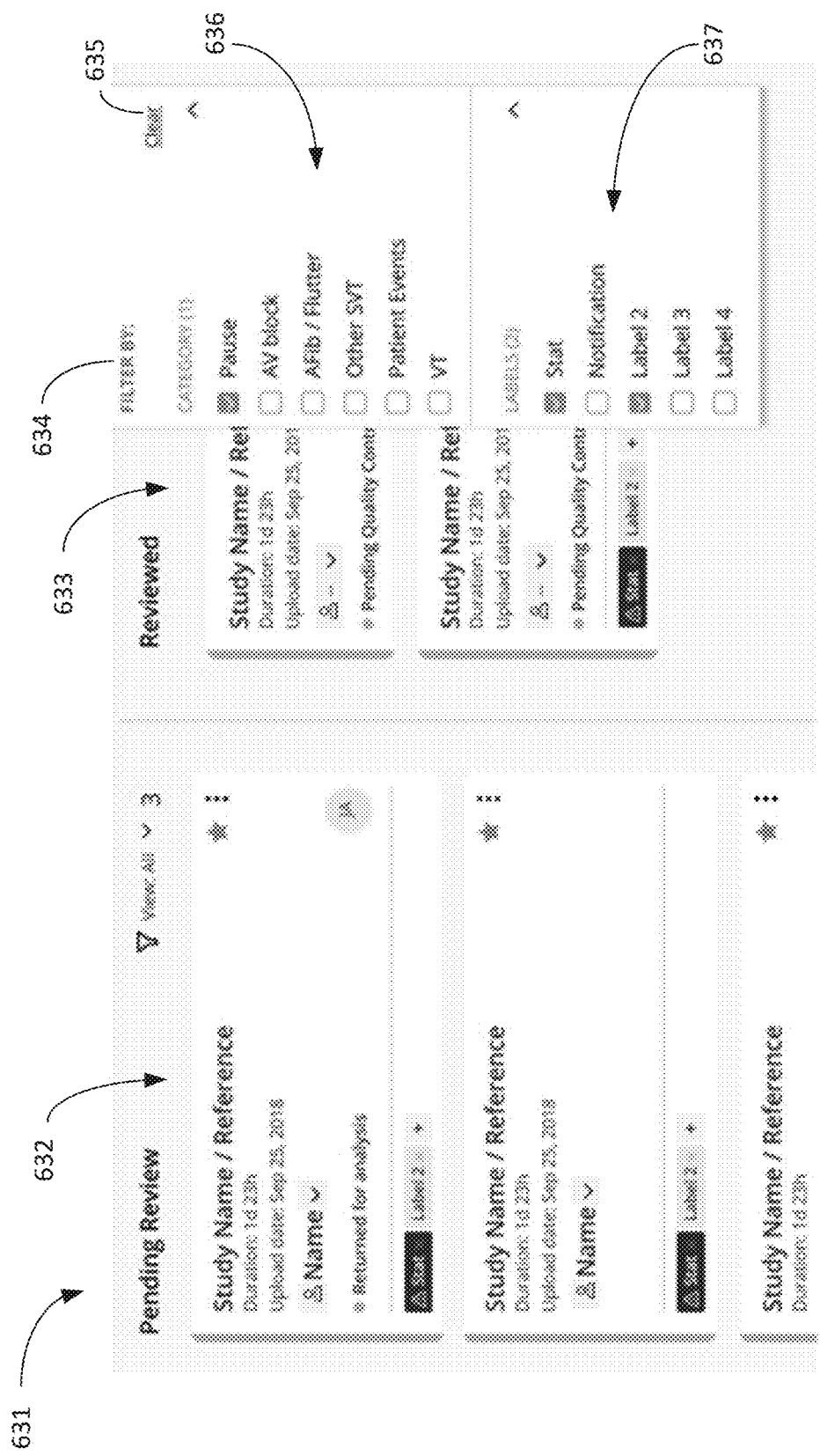

Referring now to FIG. 18D, interface 631 illustrates pending review window 632, which may be similar to pending review window 603, and reviewed window 633, which may be similar to reviewed window 604. As shown in FIG. 18D, interface 631 may include filter window 634 which may be used to filter profiles of the ECG system. Filter window 634 may include category section 636 and label section 637. Category section 636 may include a special type of label corresponding to a condition, anomaly, or event. Label section 637 may include labels to indicate information about a respective ECG profile such as "stat" and "notification". Notification may correspond to a highlighted or flagged portion of the ECG data and/or may include certain information about the ECG data. The categories and/or labels in filter window 634 may be elected to display only the ECG profiles having the selected categories and/or labels. Clear button 635 may be used to reset the filter.

Figure 18E:
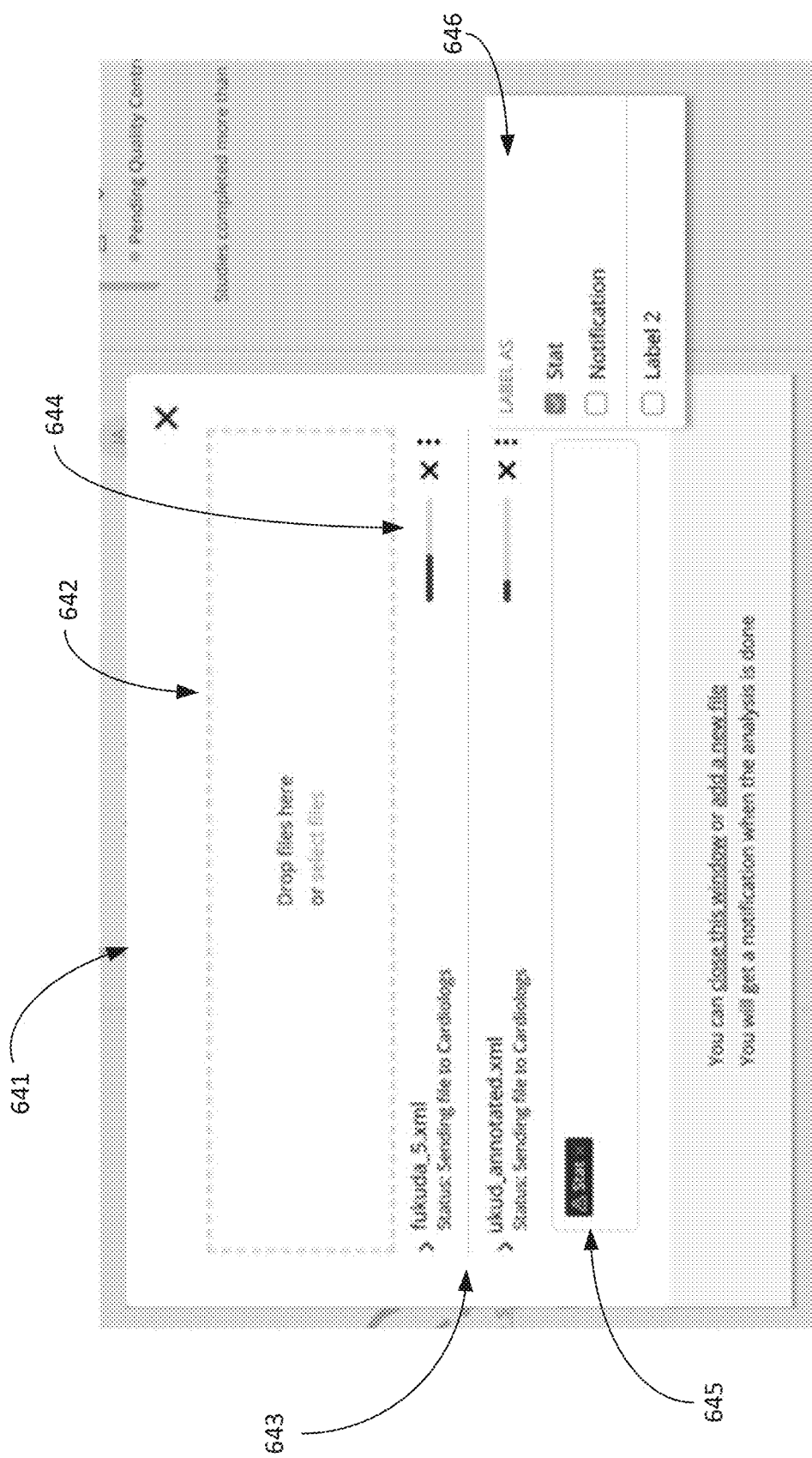

Referring now to FIG. 18E, interface 641 is illustrated which may be used to upload a new ECG signal. Upload interface 641 may be generated when upload button 607 in FIG. 18A is engaged. Interface 641 may include upload window 642 which may be used to upload ECG data to the ECG system. Upon selecting an ECG file to upload, the ECG file will be placed in upload queue 643 which may show the files selected to be uploaded and may further show download progress meter 644 that visually displays the progress of the upload to the ECG system. From the upload queue, label window 646 may be displayed to add a label to the ECG file while it is being uploaded to the ECG system. Upload interface may further include label window 645 which may show the labels selected for an ECG signal in upload queue 643.

Figure 18F:
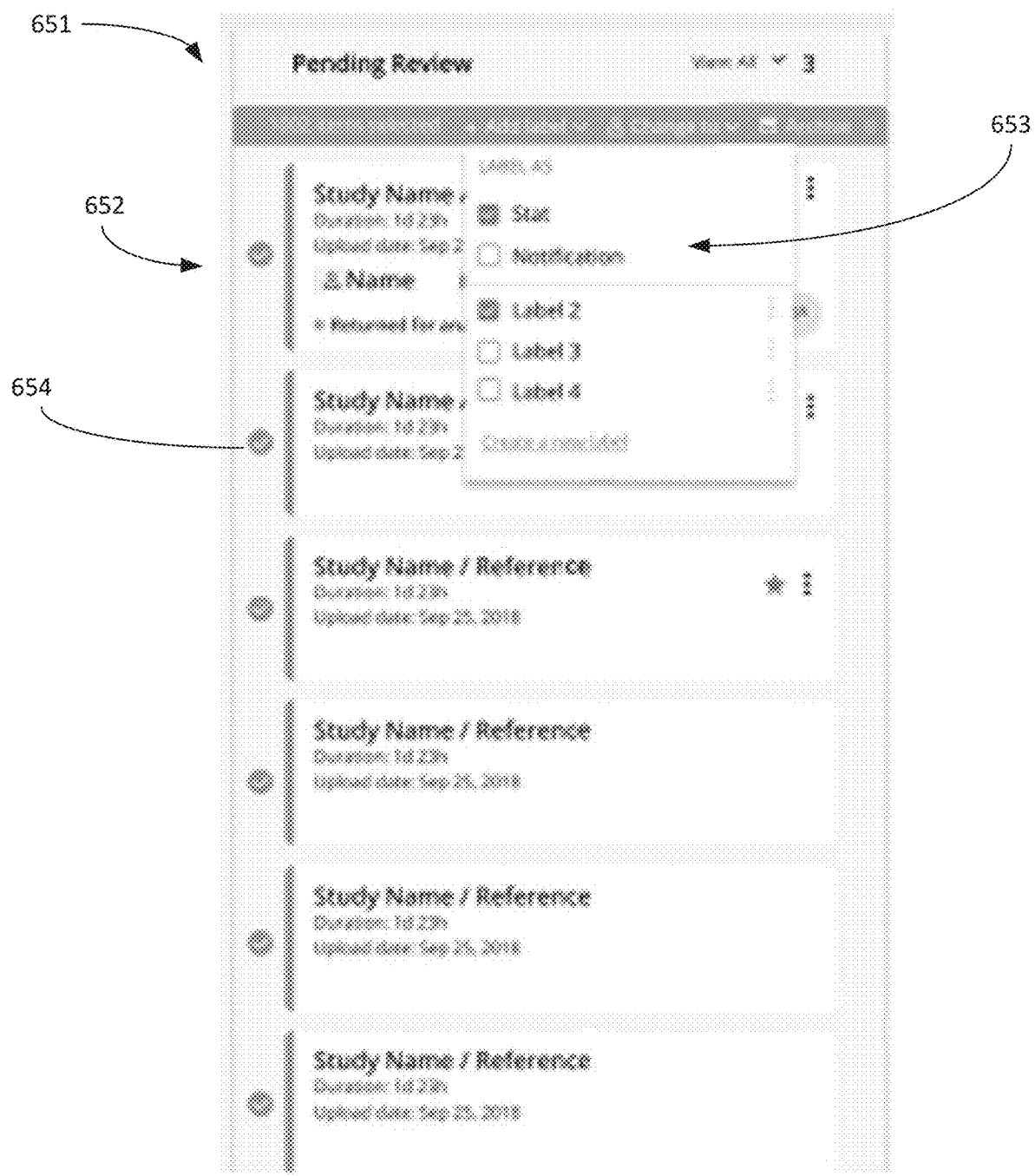

Referring now to FIG. 18F, pending review window 651 is illustrated, which is similar to pending review window 603 and may include ECG profiles 652 that are pending reviewing. As shown in FIG. 18F, two or more ECG profiles 652 may be selected at the same time by engaging selection button 654 next to the respective ECG profile. Upon selecting multiple ECG profiles 652, label window 653 may be displayed to add one or more labels and/or categories to the selected ECG profiles. For example, label window 653 may include multiple label options and a "create a new label" option which may selected to add new labels to the selected ECG profiles.

Figure 18G:
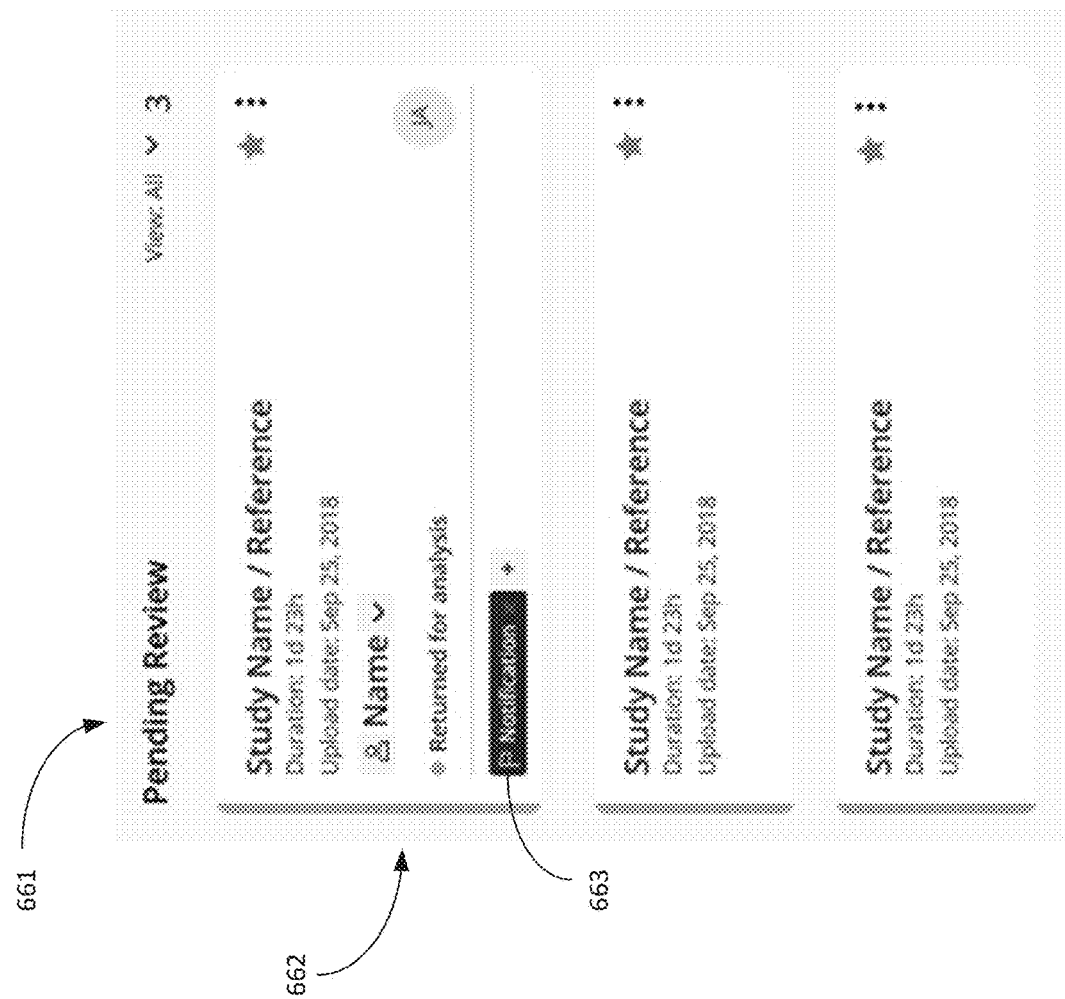
Figure 18H:
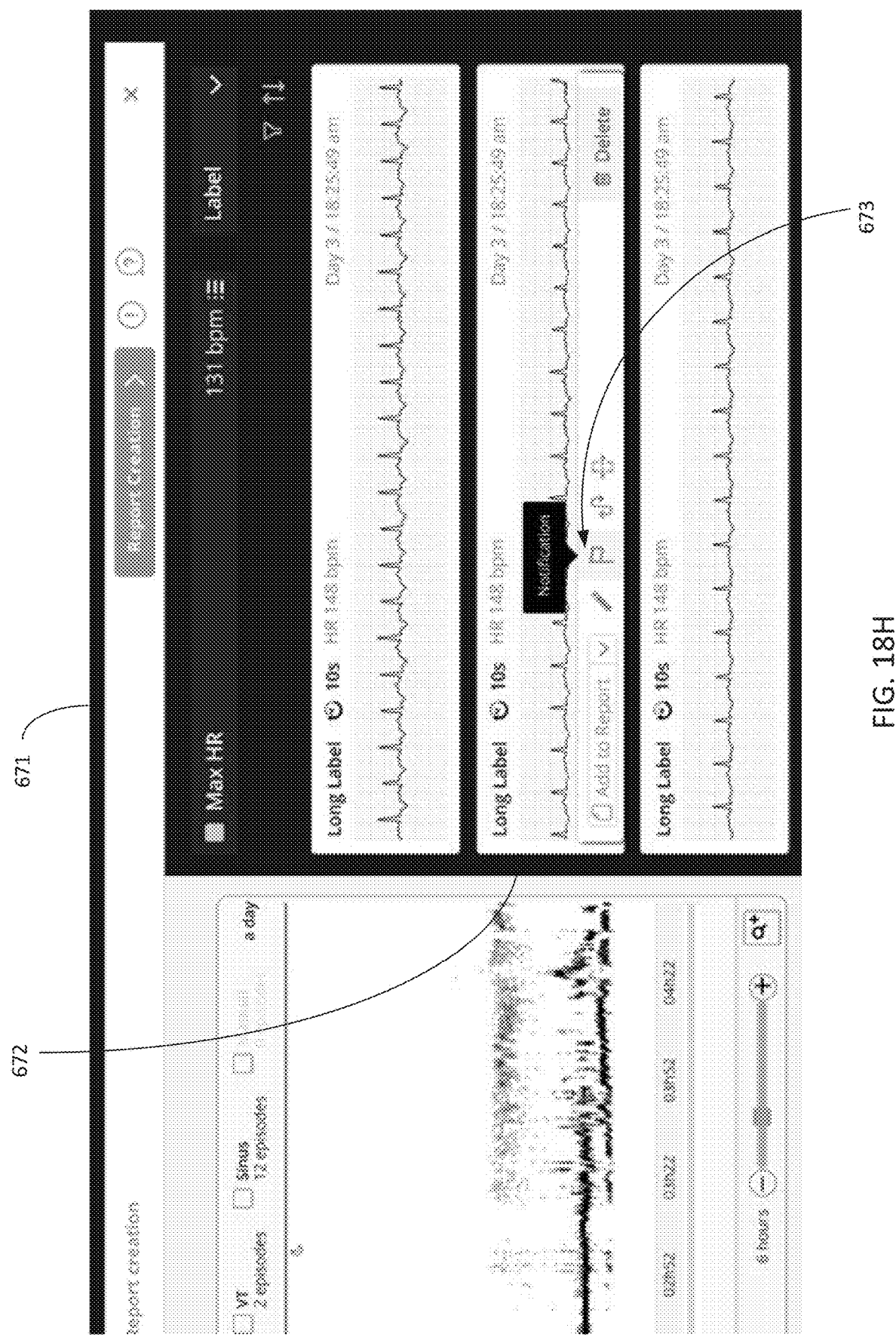

Referring now to FIG. 18G, pending review window 661 is illustrated, which is similar to pending review window 603 and may include ECG profile 662. ECG profile 662 may be similar to profile 611 as it may include a title, ECG information, and at least one label. For example label 663 may indicate that a notification has been added to the ECG data corresponding to profile 662. The label identified in label 663 may also be associated with the ECG data when the ECG data is displayed as a beat strip in a different interface. For example, referring now to FIG. 18H, interface 671 may display various beat strips such as beat strip 672. Beat strip 672 may correspond to the ECG data associated with ECG profile 662. Further beat strip 672 may include notification 673 which may be the same as label 663 and/or may include a flag icon. Notification 673 may indicate the same notification as label 663. In one example, the notification may indicate the presence of an episode in the ECG strip. A notification may be generated by a user (e.g., a physician notification) or may be automatically generated (e.g., when an anomaly, episode, condition, etc. is detected) and assigned to the ECG profile. Adding a notification to ECG data may cause that flagged ECG strip or a portion thereof to be automatically be added to a report that is ultimately generated regarding the ECG data.

Figure 19A:
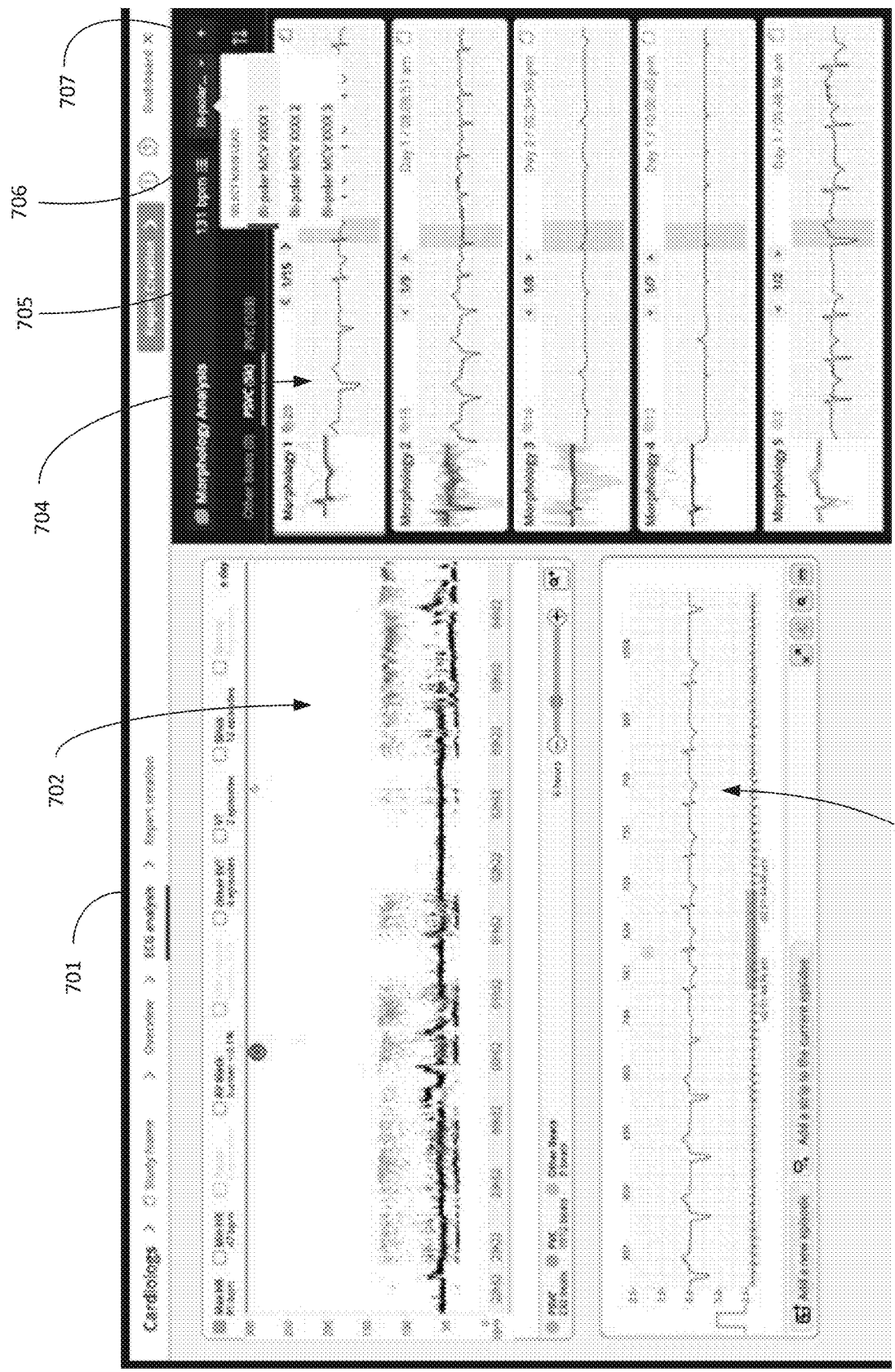
FIGS. 19A-19B illustrate user interfaces for selecting and displaying ECG data from multiple leads.

Referring now to FIG. 19A, interactive display 701 is illustrated. Interactive display 701 includes first graphic window 702, which is similar to first graphic window 124, and second graphic window 703, which is similar to second graphic window 125. Interactive display 701 may also include third graphic window 704 which may include analysis or additional information about the plurality of beats in first graphic window 702. For example, third graphic window 704 may illustrate one or more morphologies, each including a plurality of beat strips that have matched or otherwise grouped together based on certain similarities, as described above. Interactive display may include lead button 706 which opens lead window 705 when lead button 706 is engaged. Lead window 705 may include a list of available leads to select and view in second graphic window 703 and/or third graphic window 704. As shown in FIG. 19A, Bi-polar lead 1 may be selected and Bi-polar lead 2 and Bio-polar lead 3 may also available for display in second graphic window 703 and/or third graphic window 704 but may not be selected. Further add lead button 707 may be engaged to simultaneously display ECG data from a second lead.

Figure 19B:
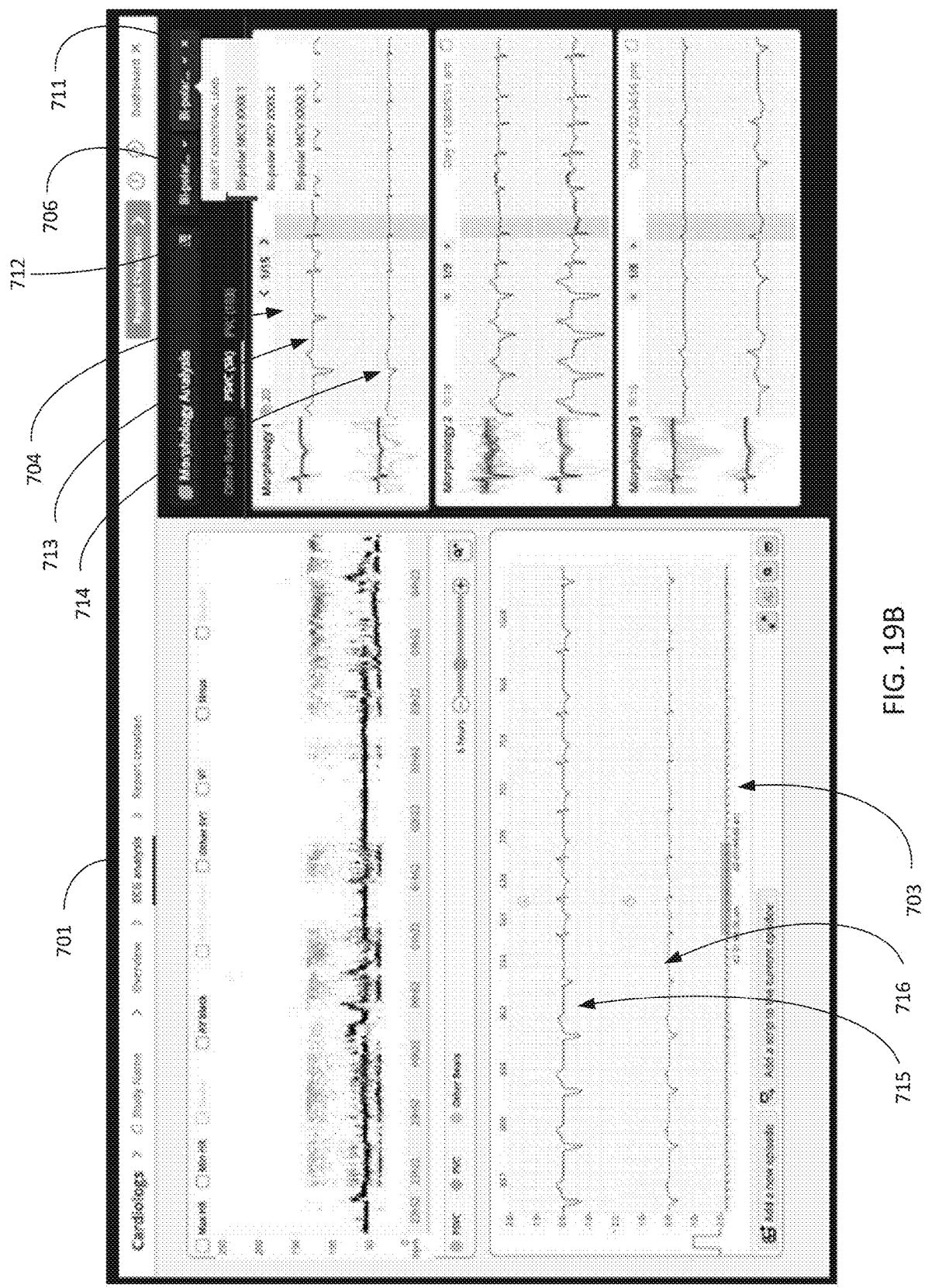

Referring now to FIG. 19B, interactive display 701 is illustrated with two leads selected for display in second graphic window 703 and/or third graphic window 704. Specifically, after lead button 707 of FIG. 19A is engaged, second lead button 711 may appear in addition to lead window 712 which may be similar to lead window 705 and may include the same list of available leads to select and display in second graphic window 703 and/or third graphic window 704. Using lead button 706 and 711, two different leads may be selected from the list of available leads for display in second graphic window 703 and/or third graphic window 704. The two different leads may correspond to the same time frame and may have the same sampling frequency. The leads may be two different leads that were placed at different positions on a patient's body and thus may detect slighty different ECG data though the heart activity they detect is the same.

As shown in FIG. 19B, second graphic window 703 and third graphic window 704 may display synced ECG data (e.g., strips) from the two different leads such that the detected data is shown at the same time along a horizontal "x" axis. Specifically ECG strip 713 and ECG strip 14 may be displayed in third graphic window 704 and ECG strip 715 and ECG strip 716 may be displayed in second graphic window 703. ECG strip 713 may correspond to ECG strip 715 and ECG strip 714 may correspond to ECG strip 716. It is understood that displaying the two different ECG strips simultaneously may facilitate a better understanding of ECG events, episodes, anomalies, irregularities, and/or conditions. For example, one lead may detect noise which may be disregarded if the noise is not detected by the other lead. In another example, an anomaly may be faint in one ECG strip but may be much more pronounced in the second ECG strip due to the position of the second lead relative to the first lead. It is further understood that using lead window 712, different leads, other than the two shown, may be selected for further comparison. It is further understood that, while two leads are shown in second graphic window 703 and third graphic window 704, more than two leads may be displayed (e.g., 3 leads, 4 leads, 5 leads, etc.).

Figure 20:
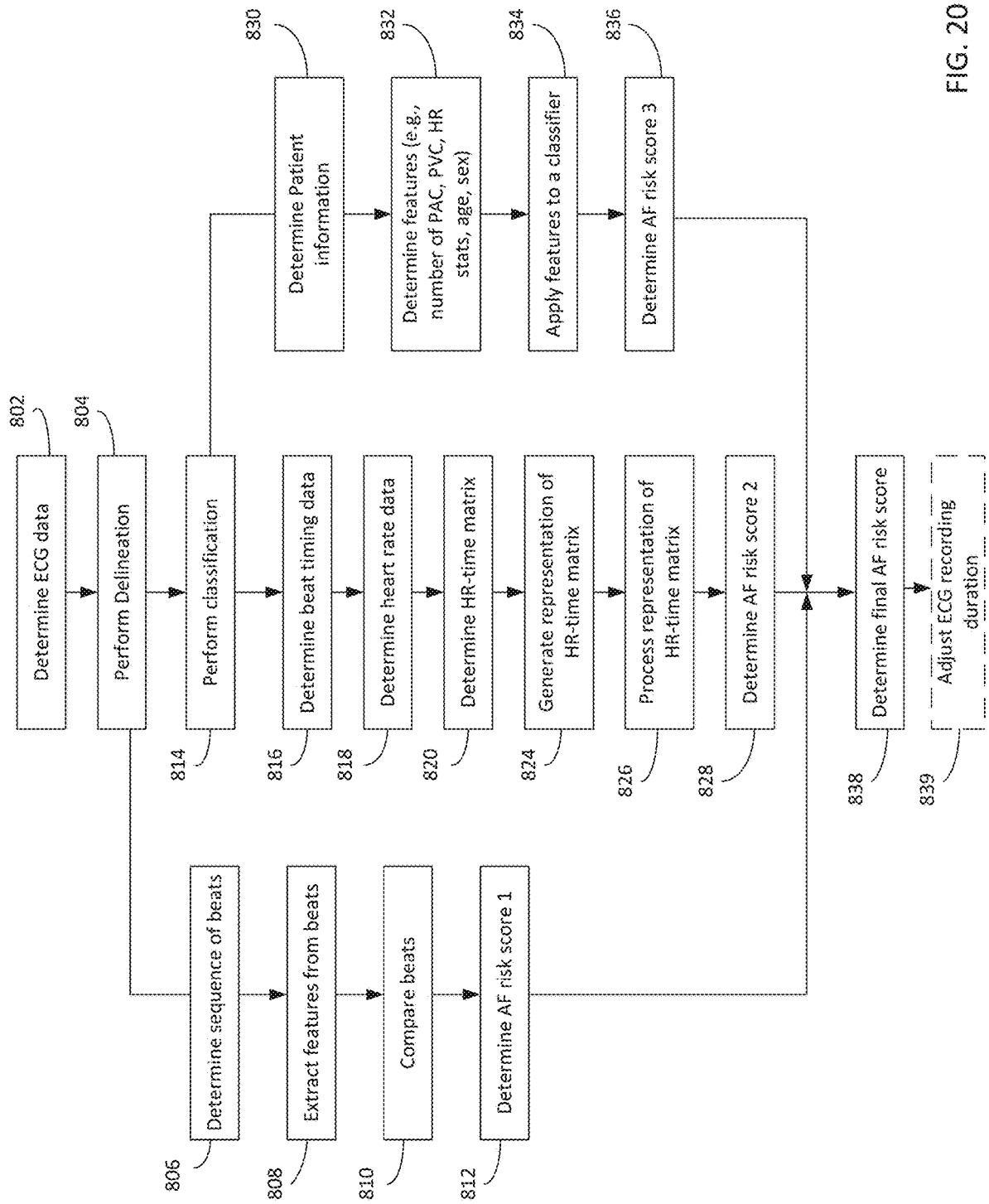
FIG. 20 illustrates an exemplary process for determining an atrial fibrillation risk score.

Referring now to FIG. 20, an exemplary process for determining an atrial fibrillation risk score is illustrated. The process illustrated in FIG. 20 may be used to determine a risk of atrial fibrillation in the near future (e.g., in the next 7 days) based on ECG data that does not involve any atrial fibrillation events. It is understood that the ECG data may be generated from fewer than 12 leads, such as 1-3 leads and/or the ECG recording device may be an ambulatory device. Some or all of the steps of the process depicted in FIG. 20 may be performed in a distributed manner across any number of devices (e.g., computing devices and/or servers). For example, the process illustrated in FIG. 20 may be performed by server 15 described above with respect to FIG. 2. Some or all of the steps of the process may be optional and may be performed in a different order.

To initiate the process set forth in FIG. 20, an ECG signal including ECG data may be determined at step 802. For example, this may involve receiving raw ECG data at the ECG platform. The raw ECG data may, optionally, be preprocessed as described above (e.g., to remove noise). The ECG data may be over a certain time period (e.g., 24 hours) and/or may be generated by a 24 hour holter. Alternatively, the ECG data may be a portion (e.g., 24 hours) of a longer recording (e.g., 7-day holter recording). It is understood that any other recording time period may be used.

Upon receiving and/or determining the ECG data, at step 804 the ECG data may be analyzed and/or processed using at least one delineation algorithm to perform delineation. For example, one or more algorithms and/or neural networks may be trained to perform delineation and process the ECG data to determine QRS onsets. After step 804, steps 806-812, 814-828 and/or 830-836 may be performed either sequentially or simultaneously. At step 806, a sequence of beats may be determined. For example, based on the QRS onsets, a sequence of beats may be identified and based on this information the ECG data may be segmented and/or the segments of the ECG data may be stacked or otherwise grouped together. At step 808, features from each beat may be extracted. For example, each beat (e.g., segment of the ECG data) may be processed by one or more neural networks (e.g., deep neural network) may extract features from each beat. The models (e.g., neural networks) may be trained to determine features that may be indicative of and/or are predictive of or otherwise inform a prediction regarding a risk of atrial fibrillation At step 810, the beats may be compared based on the features extracted from each beat. For example, beats having certain features may be identified, trends or patterns of beats having certain features may be determined, and/or beats with similar features may be grouped together. At step 812, an atrial fibrillation risk score may be generated based on the extracted features at step 808 and/or the comparison of the beats at step 810. For example, the presence of certain features identified at step 808 and/or a trend or pattern of beats having certain features identified at step 810 may be used to determine the atrial fibrillation risk score at step 812. This atrial fibrillation risk score may be indicative of a risk of an atrial fibrillation event for the patient in the near future (e.g., next 7 days).

Referring again to step 804, after delineation is performed, the ECG data and/or one or more outputs of the delineation algorithm may be analyzed and/or processed using at least one classification algorithm to perform classification at step 814. For example, the ECG data and/or one or more outputs of the delineation algorithm (e.g., QRS onsets) may be analyzed to classify the ECG data, or a portion thereof corresponding to a beat, as normal, PAC or PVC. After step 804, steps 816-828 and 830-836 may be performed either sequentially or simultaneously.

At step 816, timing data about beats detected in the ECG data may be determined. For example, a timestamp or other time data may be determined for each beat. The timestamp may be a time at which the beat occurred since the beginning of the recording. At step 818, heart rate data based on the identified beats may be determined. The heart rate data may be determined by identifying an R-R interval for each beat based on the timestamps determined for each beat. At step 820, a heat rate-time (HR-time) matrix may be determined. The HR-time matrix may be formed by the time data determined at step 816 and the heart rate data determined at step 818. For example, each row in the HR-time matrix may represent a bin of heart rate values and each column may represent a bin of timestamps, similar to the approach described above with respect to FIGS. 11 and 12.

Figure 21:
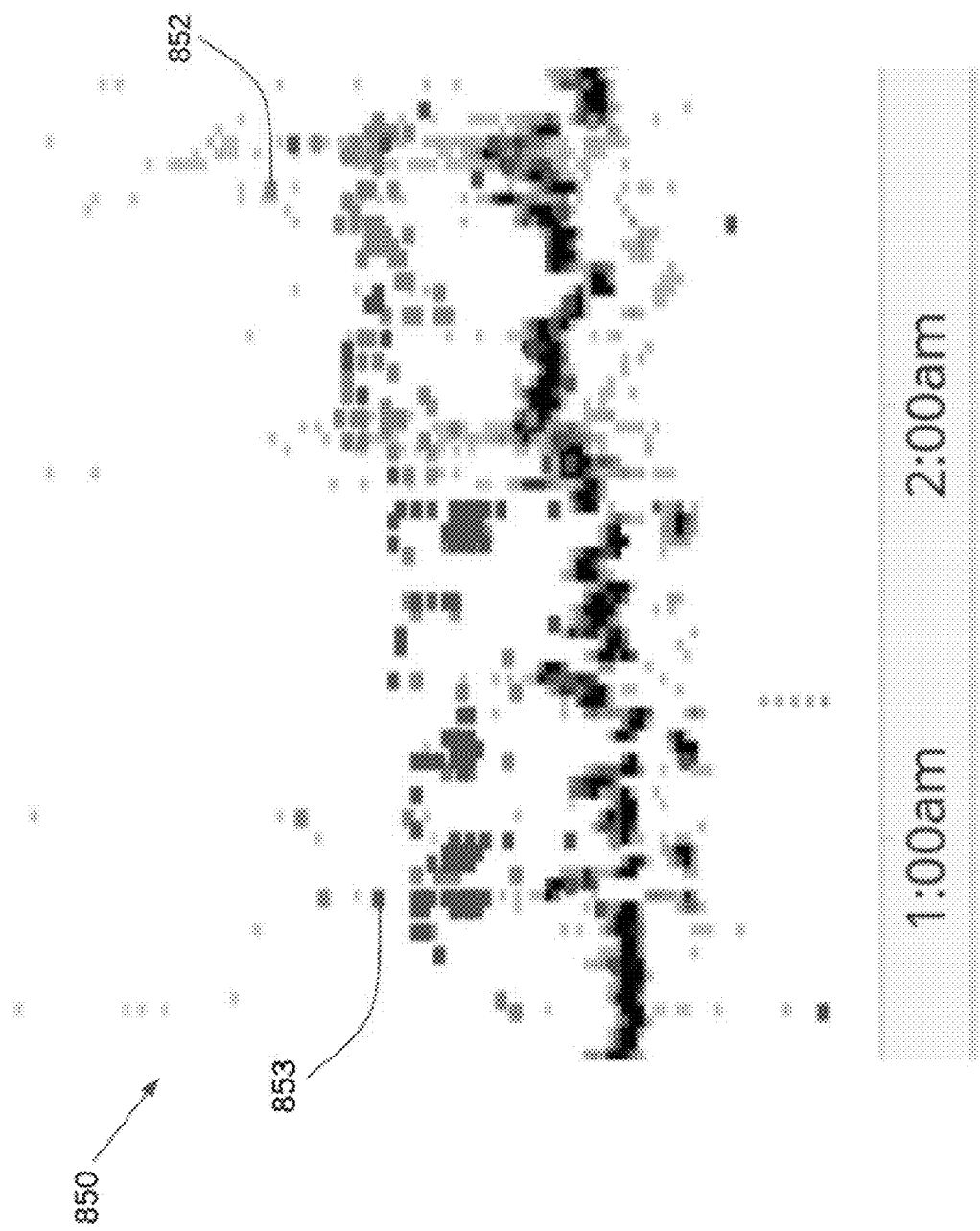
FIG. 21 illustrates an exemplary graphical representation of a heart rate-time matrix.

At step 824, a graphical representation of the HR-time matrix may be generated. The graphical representation of the HR-time matrix may be constructed using beat categories identified at step 814 (e.g., normal, PAC, and PVC). For example, a graphical representation of an HR-time matrix is illustrated in FIG. 21. As shown in FIG. 21, graphical representation 850 may include time along the x-axis and may include a plurality of heart rate points plotted with respect to time. Graphical representation 850 may include identifier 852 and identifier 853 which may identify PAC or PVC with respect to time on graphical representation 850. It is understood that similar graphical representations may be generated with only beats in certain categories (e.g., PAC, PVC, etc.).

Referring again to FIG. 20, at step 826, the graphical representation generated at step 824 may be processed by one or more neural networks trained to determine a risk or likelihood of atrial fibrillation. The one or more neural networks may be a DNN and/or CNN, for example. At step 828, a score indicative of a risk of atrial fibrillation may be generated by the one or more neural networks used to process the graphical representation. In one example, the one or more neural networks may additionally or alternatively process graphical representations using only beats classified as PAC and/or PVC.

Additionally, after step 814, patient information may be determined at step 830. For example, information about the patient corresponding to the ECG data determined at step 802 may be determined, such as age, sex, patient medical history, family medical history, etc. At step 832, features such as number of PAC, number of PVC, heart rate statistics, age may be determined. The heart rate statistics may be maximum heart rate, minimum heart rate, and/or average heart rate, for example. In one example, one or more neural networks may be used to extract and/or determine features relevant to risk of atrial fibrillation. For example, ECG datasets with known atrial fibrillation at a later time (e.g., days later) but with no atrial fibrillation in the ECG signal may be processed using one or more neural networks to determine features (e.g., number of PAC, number of PVC, HR statistics, age and/or sex) relevant to ECG data with no atrial fibrillation but associated with patient's known to have experienced atrial fibrillation at a later time (e.g, within the next 7 days).

At step 834, the features determined at step 832 may be applied to a classifier (e.g. one or more neural networks) to ultimately determine a risk score for such ECG data and patient information. For example, the classifier may determine the presence of one or more features which may be used to inform a likelihood or risk of the patient experiencing atrial fibrillation in the future (e.g., in the next 7 days). In one example the classifier may be a DNN, logistic regression, and/or a Random Forest.

At step 838, the atrial fibrillation risk score determined at step 812, step 828 and/or step 836 may be used to determine a final atrial fibrillation risk score that may be indicative of a risk or likelihood that the patient will experience one or more atrial fibrillation events in the near future (e.g., next 2-3 days, next 7 days, next month, etc.). It is understood that the ECG data determined at step 802 may not include any atrial fibrillation events but the score determined at steps 812, 828, 836 and 838 may indicate a likelihood or risk of a future atrial fibrillation event.

The atrial fibrillation risk score determined at steps 812, 828 and/or 836 may be input into a model (e.g., one or more neural network) trained to determine the final atrial fibrillation risk score. In another example, risks determined at steps 812, 828, 836 may be averaged or alternatively a weighted average or combined score may be determined. Alternatively, these risks may be combined in any other way to determine the final atrial fibrillation risk score at step 838.

At optional step 839, an ECG monitoring duration may be adjusted based on the final atrial fibrillation risk. For example, if the final atrial fibrillation risk score indicates that a patient has a high risk of developing atrial fibrillation in the near future (e.g., the final atrial fibrillation risk satisfies and/or exceeds a certain threshold value indicating a high risk of atrial fibrillation within the next 7 days), the ECG processing system may cause an ECG recorder to set, extend and/or adjust ECG monitoring to capture the predicted atrial fibrillation event (e.g., in the next 7 days). For example, the ECG processing system may cause an ambulatory recording device to record ECG data for a duration of time that will capture the predicted atrial fibrillation event.

It should be understood that any of the operations described herein above may be implemented at least in part as computer-readable instructions stored on a computer-readable memory. Upon execution of the computer-readable instructions by a processor, the computer-readable instructions may cause a node to perform the operations. It will of course be understood that the embodiments described herein are illustrative, and components may be arranged, substituted, combined, and designed in a wide variety of different configurations, all of which are contemplated and fall within the scope of this disclosure.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims.

What is claimed is:

1. A computerized-system for analyzing electrocardiogram (ECG) data of a patient, the computerized-system configured to:
   analyze the ECG data to determine a presence of atrial fibrillation in the ECG data, the ECG data sampled over a plurality of time points;

if the atrial fibrillation is determined to be present based on the analysis of the ECG data, generate information to identify the presence of the atrial fibrillation for display; and if the atrial fibrillation is determined not to be present based on the analysis of the ECG data, further analyze the ECG data, wherein the analysis comprises:

perform delineation on the ECG data using a delineation neural network to generate delineation output values indicative of a likelihood of the presence of one or more waves at each time point of the plurality of time points;

determine a plurality of beats based on the values; and perform classification on the ECG data and the plurality of beats to generate classification output values indicative of a likelihood of a presence of one or more normal beats, premature atrial complexes (PAC), or premature ventricular complexes (PVC), wherein the further analysis comprises:

apply the ECG data, delineation output values, and classification output values to a risk analyzer, the risk analyzer comprising one or more neural networks trained to determine a risk of atrial fibrillation; and determine a risk score using the risk analyzer, the risk score based on at least the ECG data, the delineation output values, and the classification output values, the risk score indicative of future atrial fibrillation for the patient, the future atrial fibrillation being at a time in the future after the plurality of time points for which the ECG data was sampled.

2. The computerized-system of claim 1, the computerized-system further configured to:

extract a plurality of first features from the plurality of beats; and determine a first risk score based on the plurality of first features, the first risk score indicative of future atrial fibrillation for the patient.

3. The computerized-system of claim 2, wherein performing delineation on the ECG data determines a plurality of QRS onset values.

4. The computerized-system of claim 2, the computerized-system further configured to:

determine a plurality of timestamps corresponding to the plurality of beats;

determine a plurality of heart rate values based on the plurality of timestamps;

determine a matrix based on the plurality of timestamps and the plurality of heart rate values;

generate a graphical representation of the matrix; and process the graphical representation of the matrix using at least one neural network to determine a second risk score indicative of future atrial fibrillation for the patient.

5. The computerized-system of claim 4, wherein the at least one neural network is at least one deep neural network (DNN).

6. The computerized-system of claim 4, the computerized-system further configured to:

determine patient information corresponding to the patient, the patient information comprising one or more of age and sex of the patient;

determine a plurality of second features of the ECG data indicative of atrial fibrillation; and apply the plurality of second features to a classifier to determine a third risk score indicative of future atrial fibrillation for the patient.

7. The computerized-system of claim 6, wherein the classifier is one or more of DNN, logistic regression and a Random Forest.

8. The computerized-system of claim 6, wherein the risk score is based on one or more of the first risk score, the second risk score and the third risk score.

9. The computerized-system of claim 6, the computerized-system further configured to:

determine an average of the first risk score, the second risk score, and the third risk score to determine the risk score.

10. The computerized-system of claim 6, the computerized-system further configured to:

apply the first risk score, the second risk score, and the third risk score to a first neural network trained to determine the risk score.

11. The computerized-system of claim 1, wherein the risk score is indicative of a likelihood of atrial fibrillation in a set period of time, and the computerized-system is further configured to:

cause an ECG recorder to capture second ECG data during the set period of time.

12. A method for analyzing electrocardiogram (ECG) data of a patient, the method comprising:

analyzing the ECG data to determine a presence of atrial fibrillation in the ECG data, the ECG data sampled over a plurality of time points;

if the atrial fibrillation is determined to be present based on the analysis of the ECG data, generating information to identify the presence of the atrial fibrillation for display; and if the atrial fibrillation is determined not to be present based on the analysis of the ECG data, further analyzing the ECG data, wherein the analysis comprises:

performing delineation on the ECG data using a delineation neural network to generate delineation output values indicative of a likelihood of the presence of one or more waves at each time point of the plurality of time points;

determining a plurality of beats based on the values; and performing classification on the ECG data and the plurality of beats to generate classification output values indicative of a likelihood of a presence of one or more normal beats, premature atrial complexes (PAC), or premature ventricular complexes (PVC), wherein the further analysis comprises:

apply the ECG data, delineation output values, and classification output values to a risk analyzer, the risk analyzer comprising one or more neural networks trained to determine a risk of atrial fibrillation; and determining a risk score using the risk analyzer, the risk score based on at least the ECG data, the delineation output values, and the classification output values, the risk score indicative of future atrial fibrillation for the patient, the future atrial fibrillation being at a time in the future after the plurality of time points for which the ECG data was sampled.

13. The method of claim 12, further comprising:

extracting a plurality of first features from the plurality of beats; and determining a first risk score based on the plurality of first features, the first risk score indicative of future atrial fibrillation for the patient.

14. The method of claim 13, wherein performing delineation on the ECG data determines a plurality of QRS onset values.

15. The method of claim 13, further comprising:
- determining a plurality of timestamps corresponding to the plurality of beats;
- determining a plurality of heart rate values based on the plurality of timestamps;
- determining a matrix based on the plurality of timestamps and the plurality of heart rate values;
- generating a graphical representation of the matrix; and
- processing the graphical representation of the matrix using at least one neural network to determine a second risk score indicative of future atrial fibrillation for the patient.

16. The method of claim 15, wherein the at least one neural network is at least one deep neural network (DNN).

17. The method of claim 15, further comprising:
- determining patient information corresponding to the patient, the patient information comprising one or more of age and sex of the patient;
- determining a plurality of second features of the ECG data indicative of atrial fibrillation; and
- applying the plurality of second features to a classifier to determine a third risk score indicative of future atrial fibrillation for the patient.

18. The method of claim 17, wherein the classifier is one or more of DNN, logistic regression and a Random Forest.

19. The method of claim 17, wherein the risk score is based on one or more of the first risk score, the second risk score and the third risk score.

20. The method of claim 17, further comprising:
- determining an average of the first risk score, the second risk score, and the third risk score to determine the risk score.

21. The method of claim 17, further comprising:
- applying the first risk score, the second risk score, and the third risk score to a first neural network trained to determine the risk score.

22. The method of claim 12, wherein the risk score is indicative of a likelihood of atrial fibrillation in a set period of time, and further comprising:
- causing an ECG recorder to capture second ECG data during the set period of time.

23. A non-transitory computer-readable memory medium configured to store instructions thereon that, when loaded by at least one processor, cause the at least one processor to:
- analyze ECG data of a patient to determine a presence of atrial fibrillation in the ECG data, the ECG data sampled over a plurality of time points;
- if the atrial fibrillation is determined to be present based on the analysis of the ECG data, generate information to identify the presence of the atrial fibrillation for display; and
- if the atrial fibrillation is determined not to be present based on the analysis of the ECG data, further analyze the ECG data, wherein the analysis comprises:
  - perform delineation on the ECG data using a delineation neural network to generate delineation output values indicative of a likelihood of the presence of one or more waves at each time point of the plurality of time points;
  - determine a plurality of beats based on the values; and
  - perform classification on the ECG data and the plurality of beats to generate classification output values indicative of a likelihood of a presence of one or more normal beats, premature atrial complexes (PAC), or premature ventricular complexes (PVC),
  wherein the further analysis comprises:
    - apply the ECG data, delineation output values, and classification output values to a risk analyzer, the risk analyzer comprising one or more neural networks trained to determine a risk of atrial fibrillation; and
    - determine a risk score using the risk analyzer, the risk score based on at least the ECG data, the delineation output values, and the classification output values, the risk score indicative of future atrial fibrillation for the patient, the future atrial fibrillation being at a time in the future after the plurality of time points for which the ECG data was sampled.

24. The non-transitory computer-readable memory medium of claim 23, further configured to cause the at least one processor to:
- extract a plurality of first features from the plurality of beats; and
- determine a first risk score based on the plurality of first features, the first risk score indicative of future atrial fibrillation for the patient.

25. The non-transitory computer-readable memory medium of claim 24, further configured to cause the at least one processor to:
- determine a plurality of timestamps corresponding to the plurality of beats;
- determine a plurality of heart rate values based on the plurality of timestamps;
- determine a matrix based on the plurality of timestamps and the plurality of heart rate values;
- generate a graphical representation of the matrix; and
- process the graphical representation of the matrix using at least one neural network to determine a second risk score indicative of future atrial fibrillation for the patient.

26. The non-transitory computer-readable memory medium of claim 25, further configured to cause the at least one processor to:
- determine patient information corresponding to the patient, the patient information comprising one or more of age and sex of the patient;
- determine a plurality of second features of the ECG data indicative of atrial fibrillation; and
- apply the plurality of second features to a classifier to determine a third risk score indicative of future atrial fibrillation for the patient.

27. The non-transitory computer-readable memory medium of claim 26, wherein the risk score is based on one or more of the first risk score, the second risk score and the third risk score.

* * * * *